US012685586B2

(12) United States Patent
Raina et al.

(10) Patent No.: US 12,685,586 B2
(45) Date of Patent: Jul. 21, 2026

(54) SYSTEMS AND DEVICES FOR TREATING LUNG TUMORS

(71) Applicant: ZIDAN MEDICAL, INC., New York, NY (US)

(72) Inventors: Shashank Raina, New York, NY (US); Shivkumar Sabesan, New York, NY (US); Mark Gelfand, New York, NY (US); Miriam Taimisto, New York, NY (US)

(73) Assignee: ZIDAN MEDICAL, INC., New York, NY (US)

( * ) Notice: Subject to any disclaimer, the term of this patent is extended or adjusted under 35 U.S.C. 154(b) by 523 days.

(21) Appl. No.: 18/023,828

(22) PCT Filed: Aug. 16, 2021

(86) PCT No.: PCT/US2021/046068
§ 371 (c)(1),
(2) Date: Feb. 28, 2023

(87) PCT Pub. No.: WO2022/046443
PCT Pub. Date: Mar. 3, 2022

(65) Prior Publication Data
US 2023/0301711 A1 Sep. 28, 2023

Related U.S. Application Data

(60) Provisional application No. 63/071,805, filed on Aug. 28, 2020.

(51) Int. Cl.
*A61B 18/14* (2006.01)
*A61B 18/00* (2006.01)

(52) U.S. Cl.
CPC ...... *A61B 18/1492* (2013.01); *A61B 2018/00029* (2013.01); *A61B 2018/00285* (2013.01);
(Continued)

(58) Field of Classification Search
CPC ...... A61B 18/1492; A61B 2018/00029; A61B 2018/00285; A61B 2018/00541;
(Continued)

(56) References Cited

U.S. PATENT DOCUMENTS

| | | | |
|---|---|---|---|
| 4,920,978 | A | 5/1990 | Colvin |
| 5,585,362 | A | 12/1996 | Wilson |

(Continued)

FOREIGN PATENT DOCUMENTS

| | | |
|---|---|---|
| CN | 201356648 Y | 12/2009 |
| CN | 102639077 A | 8/2012 |

(Continued)

OTHER PUBLICATIONS

International Search Report for PCT/US2021/046068 dated Feb. 1, 2022, 5 pages.

(Continued)

*Primary Examiner* — Mark W. Bockelman
(74) *Attorney, Agent, or Firm* — Nixon & Vanderhye, P.C.

(57) ABSTRACT

A system for treatment of a target region of lung tissue including: a flow regulator configured to be interposed between a conductive fluid source and a conductive fluid outlet at a distal region of a catheter positioned in the target region and the conductive fluid outlet is positionable at or in proximity of the target region of lung tissue, wherein the flow regulator being further configured to control a flow rate or a bolus quantity of the conductive fluid coming from the fluid source and delivered through the conductive fluid outlet to the target region; an ablation electrode mounted to the distal region of the catheter; a controller configured to control the flow regulator, and configured to control power delivered from an ablation energy source to the ablation electrode, wherein the controller is configured to: receive (Continued)

one or more of the values of the control parameter; control the delivery of power from the ablation energy source to the ablation electrode; while the power is delivered to the ablation electrode, maintain a temperature in the target region within a first temperature range by controlling the flow regulator to adjust the flow of the conductive fluid delivered to the conductive fluid outlet; determine an amount of the conductive fluid delivered to the conductive fluid output; in response to the amount of the conductive fluid reaching a threshold volume, ceasing the flow of the conductive fluid to the conductive fluid output; during the cessation of the flow of the conductive fluid to the conductive fluid output, maintain the temperature in the target region within a second temperature range by adjusting the power delivered to ablation electrode.

28 Claims, 31 Drawing Sheets

(52) U.S. Cl.
CPC ............... *A61B 2018/00541* (2013.01); *A61B 2018/00744* (2013.01)

(58) Field of Classification Search
CPC ........... A61B 2018/00744; A61B 2018/00577; A61B 2018/00642; A61B 2018/00648; A61B 2018/00678; A61B 2018/00702; A61B 2018/00708; A61B 2018/00791; A61B 2018/00863; A61B 2018/00875; A61B 2018/00898; A61B 2218/002
See application file for complete search history.

(56) References Cited

U.S. PATENT DOCUMENTS

| | | | |
|---|---|---|---|
| 5,722,403 | A | 3/1998 | McGee |
| 5,740,808 | A | 4/1998 | Panescu |
| 6,003,517 | A | 12/1999 | Sheffield |
| 6,235,022 | B1 | 5/2001 | Hallock et al. |
| 6,258,100 | B1 | 7/2001 | Alferness |
| 6,293,951 | B1 | 9/2001 | Alferness |
| 6,315,776 | B1 | 11/2001 | Edwards |
| 6,402,742 | B1 | 6/2002 | Blewett |
| 6,409,722 | B1 | 6/2002 | Hoey |
| 6,537,272 | B2 | 3/2003 | Christopherson |
| 6,702,811 | B2 | 3/2004 | Stewart |
| 6,736,810 | B2 | 5/2004 | Hoey |
| 6,770,070 | B1 | 8/2004 | Balbierz |
| 6,849,073 | B2 | 2/2005 | Hoey |
| 6,971,394 | B2 | 12/2005 | Sliwa, Jr. |
| 7,115,139 | B2 | 10/2006 | McClurken |
| 7,128,747 | B2 | 10/2006 | Ginn |
| 7,169,144 | B2 | 1/2007 | Hoey |
| 7,187,971 | B2 | 3/2007 | Sommer |
| 7,247,155 | B2 | 7/2007 | Hoey |
| 7,344,533 | B2 | 3/2008 | Pearson |
| 7,412,977 | B2 | 8/2008 | Fields |
| 7,628,789 | B2 | 12/2009 | Soltesz |
| 7,771,472 | B2 | 8/2010 | Hendricksen |
| 7,892,229 | B2 | 2/2011 | Shadduck |
| 7,913,698 | B2 | 3/2011 | Barry |
| 7,921,855 | B2 | 4/2011 | Danek |
| 7,931,647 | B2 | 4/2011 | Wizeman |
| 7,949,407 | B2 | 5/2011 | Kaplan |
| 8,088,127 | B2 | 1/2012 | Mayse |
| 8,187,268 | B2 | 5/2012 | Godara |
| 8,226,575 | B2 | 7/2012 | Levy |
| 8,262,581 | B2 | 9/2012 | Uemura |
| 8,308,722 | B2 | 11/2012 | Ormsby |
| 8,568,403 | B2 | 10/2013 | Soltesz |
| 8,709,034 | B2 | 4/2014 | Keast |
| 8,753,381 | B2 | 6/2014 | Henriksson |
| 8,858,549 | B2 | 10/2014 | Shadduck |
| 8,911,430 | B2 | 12/2014 | Hoey |
| 8,932,316 | B2 | 1/2015 | Keast |
| 9,044,254 | B2 | 6/2015 | Ladtkow |
| 9,108,052 | B2 | 8/2015 | Jarrard |
| 9,113,944 | B2 | 8/2015 | Shadduck |
| 9,161,808 | B2 | 10/2015 | Nollert |
| 9,421,070 | B2 | 8/2016 | Keast |
| 9,463,064 | B2 | 10/2016 | Subramaniam |
| 9,517,103 | B2 | 12/2016 | Panescu |
| 9,522,036 | B2 | 12/2016 | Panescu |
| 9,522,037 | B2 | 12/2016 | Panescu |
| 9,526,574 | B2 | 12/2016 | Wang |
| 9,566,115 | B2 | 2/2017 | van der Weide |
| 9,592,092 | B2 | 3/2017 | Panescu |
| 9,603,659 | B2 | 3/2017 | Subramaniam |
| 9,636,164 | B2 | 5/2017 | Panescu |
| 9,668,809 | B2 | 6/2017 | Mayse |
| 9,743,984 | B1 | 8/2017 | Curley |
| 9,770,282 | B2 | 9/2017 | Hoey |
| 9,861,440 | B2 | 1/2018 | van der Weide |
| 9,867,648 | B2 | 1/2018 | Mulcahey |
| 9,872,729 | B2 | 1/2018 | van der Weide |
| 9,884,201 | B2 | 2/2018 | Henriksson |
| 9,901,384 | B2 | 2/2018 | Clark |
| 9,943,353 | B2 | 4/2018 | Hoey |
| 9,956,032 | B1 | 5/2018 | Cosman |
| 9,993,291 | B2 | 6/2018 | Cao |
| 10,231,770 | B2 | 3/2019 | Druma |
| 10,376,299 | B2 | 8/2019 | Avitall |
| 10,842,560 | B2 | 11/2020 | Panescu |
| 2002/0115991 | A1 | 8/2002 | Edwards |
| 2002/0165448 | A1 | 11/2002 | Ben-Haim |
| 2003/0212394 | A1 | 11/2003 | Pearson |
| 2003/0228344 | A1 | 12/2003 | Fields |
| 2006/0195079 | A1 | 8/2006 | Eberl |
| 2006/0254600 | A1 | 11/2006 | Danek |
| 2007/0043350 | A1 | 2/2007 | Soltesz |
| 2007/0265687 | A1 | 11/2007 | Deem |
| 2007/0276362 | A1 | 11/2007 | Rioux |
| 2008/0051756 | A1 | 2/2008 | Makower |
| 2009/0099560 | A1 | 4/2009 | Rioux |
| 2010/0211070 | A1 | 8/2010 | Subramaniam |
| 2011/0301587 | A1 | 12/2011 | Deem |
| 2012/0053485 | A1 | 3/2012 | Bloom |
| 2012/0143099 | A1 | 6/2012 | Daniels |
| 2012/0239029 | A1 | 9/2012 | Nollert |
| 2013/0046296 | A1 | 2/2013 | Laufer |
| 2013/0310822 | A1 | 11/2013 | Mayse |
| 2013/0317339 | A1 | 11/2013 | Waldstreicher |
| 2013/0338530 | A1 | 12/2013 | Kassab |
| 2014/0018605 | A1 | 1/2014 | Soltesz |
| 2014/0046174 | A1 | 2/2014 | Ladtkow |
| 2014/0046410 | A1 | 2/2014 | Wyatt |
| 2014/0088588 | A1 | 3/2014 | Jarrard |
| 2014/0276709 | A1 | 9/2014 | Wittenberger |
| 2015/0119877 | A1 | 4/2015 | Jameson |
| 2015/0157382 | A1 | 6/2015 | Avitall |
| 2015/0265331 | A1 | 9/2015 | Fleury |
| 2015/0265342 | A1 | 9/2015 | Long |
| 2016/0051327 | A1 | 2/2016 | Brannan |
| 2016/0151103 | A1 | 6/2016 | Henne |
| 2016/0175041 | A1 | 6/2016 | Govari |
| 2016/0184013 | A1 | 6/2016 | Brannan |
| 2016/0287912 | A1 | 10/2016 | Warnking |
| 2016/0310210 | A1 | 10/2016 | Harshman |
| 2017/0079519 | A1 | 3/2017 | Sung |
| 2017/0112558 | A1 | 4/2017 | Sara |
| 2017/0128039 | A1 | 5/2017 | Waldstreicher |
| 2017/0135754 | A1 | 5/2017 | Gliner |
| 2017/0325837 | A1 | 11/2017 | Thompson |
| 2017/0325894 | A1 | 11/2017 | Krimsky |
| 2018/0161142 | A1 | 6/2018 | Finger |
| 2018/0184982 | A1 | 7/2018 | Basu |
| 2018/0263689 | A1 | 9/2018 | Govari |
| 2018/0296264 | A1 | 10/2018 | DeSimone |
| 2019/0099213 | A1 | 4/2019 | Witt |

(56)                References Cited

U.S. PATENT DOCUMENTS

| 2019/0133668 A1 | 5/2019  | Barry   |
| 2019/0254735 A1 | 8/2019  | Stewart |
| 2019/0343581 A1 | 11/2019 | Panescu |

FOREIGN PATENT DOCUMENTS

| CN | 102940524  | A  | 2/2013  |
| CN | 103037791  | A  | 4/2013  |
| CN | 103118613  | A  | 5/2013  |
| CN | 203122582  | U  | 8/2013  |
| CN | 103371865  | A  | 10/2013 |
| CN | 203341811  | U  | 12/2013 |
| CN | 103892907  | A  | 7/2014  |
| CN | 105147389  | A  | 12/2015 |
| CN | 105640642  | A  | 6/2016  |
| CN | 105943159  | A  | 9/2016  |
| CN | 106037927  | A  | 10/2016 |
| CN | 205672073  | U  | 11/2016 |
| CN | 107307901  | A  | 11/2017 |
| CN | 107456269  | A  | 12/2017 |
| CN | 109464186  | A  | 3/2019  |
| EP | 1450712    | A  | 9/2004  |
| EP | 2 563 255  |    | 3/2013  |
| EP | 3184066    | A1 | 6/2017  |
| EP | 3 763 314  |    | 1/2021  |
| WO | 2009015278 | A1 | 1/2009  |
| WO | 2010141417 | A2 | 12/2010 |
| WO | 2011/139589 |   | 11/2011 |
| WO | 2014052199 | A1 | 4/2014  |
| WO | 2014197632 | A2 | 12/2014 |
| WO | 2015006729 | A2 | 1/2015  |
| WO | 2016029022 | A1 | 2/2016  |
| WO | 2016090175 | A1 | 6/2016  |
| WO | 2016109437 | A1 | 7/2016  |
| WO | 2019051251 | A1 | 3/2019  |

OTHER PUBLICATIONS

Written Opinion of the ISA for PCT/US2021/046068 dated Feb. 1, 2022, 11 pages.

D. Scott Cohen et al., Case Reports, "Pulmonary Edema Associated With Salt Water Near-Drowning: New Insights", AM REV RESPIR DIS 1992; 146:794-796.

Lt. Commander Carl Edmonds, "A Salt Water Aspiration Syndrome" Downloaded from https://academic.oup.com/milmed/article-abstract/135/9/779/4919434 by Washington University in St. Louis user on Feb. 14, 2019, pp. 779-785.

Tatsuhiko Iishi et al., Acta Medica Okayama, "Infusion of Hypertonic Saline Into the Lung Parenchyma During Radiofrequency Ablation of the Lungs with Multitined Expandable Electrodes: Results Using A Porcine Model", vol. 63, Issue 3, Jun. 2009, 10 pages.

Tae Sung Kim et al., "Excessive Hyperthermic Necrosis of a Pulmonary Lobe After Hypertonic Saline-Enhanced Monopolar Radiofrequency Ablation", Cardiovasc Intervent Radio! (2006) 29, pp. 160-163.

Hiroshi ANAi, Effects Of Blood Flow And/Or Ventilation Restriction on Radiofrequency Coagulation Size In The Lung: An Experimental Study In Swine, Cardiovasc Intervent Radiol. (2006), 29:838-845.

Tomonobu Koizumi et al., "Clinical Experience of Bronchoscopy-Guided Radiofrequency Ablation For Peripheral-Type Lung Cancer", Case Reports in Oncological Medicine, vol. 2013, Article ID 515160, (Jan. 2013) 5 pages.

Fumiyoshi Oshima et al., Lung Radiofrequency Ablation with and without Bronchial Occlusion: Experimental Study in Porcine Lungs, Laboratory Investigations, J Vase Interv Radiol 2004; 15:1451-1456.

Receive Update
(temperature or
impedance)

Calculate pending flow setting adjustments — 610

Run pump control state machine — 611

Calculate flow start times — 612

Adjust flow rates for pending settings — 613

Finalize pending settings — 614

······· Temperature    --- Power    —— Flow    ─··─ Impedance

800

234

800

234

805

806

SYSTEMS AND DEVICES FOR TREATING LUNG TUMORS

RELATED APPLICATION

This application is the U.S. national phase of International Application PCT/US2021/046068, filed Aug. 16, 2021, which designated the U.S. and claims priority to U.S. provisional application 63/071,805, filed Aug. 28, 2020, wherein both applications are incorporated by reference.

TECHNICAL FIELD

The present disclosure is directed generally to devices and methods for ablating malignant lung tumors and more particularly to ablating lung tumors with an approach through the patient's airway.

BACKGROUND

Lung cancer remains the leading cause of cancer-related deaths in the world. In fact, lung cancer is responsible for more deaths each year in this country than breast cancer, colon cancer, and prostate cancer combined. Non-small cell lung cancer (NSCLC) is the most common type of lung cancer; it is named for the type of cell within the lung where the cancer originates. Approximately 75 to 80% of individuals with lung cancer have NSCLC. Early NSCLC refers to cancer that has not spread widely outside of its site of origin. The earlier lung cancer is detected and treated, the better the outcome. The current standard treatment for early lung cancer consists of the surgical removal of as much of the cancer as possible followed by chemotherapy and/or radiation therapy.

Surgical removal of a lung or lobe is the gold standard treatment for treating stage 1 or 2 non-small-cell-lung-cancer (NSCLC). Unfortunately, only about 15% to 30% of patients diagnosed with lung carcinoma each year are surgical candidates. Particularly, many patients with concurrent Chronic Obstructive Pulmonary Disease (COPD) are not considered suitable for surgery.

Percutaneous pulmonary radiofrequency ablation (RFA) with a needle electrode inserted through the chest wall under CT guidance has become an increasingly adopted treatment option for primary and metastatic lung tumours. The immediate technical success rate is over 95%, with a low periprocedural mortality rate and 8 to 12% major complication rate. Pneumothorax represents the most frequent complication but requires a chest tube drain in less than 10% of cases. Sustained complete tumour response has been reported in 85% to 90% of target lesions.

Bronchoscopic ablation of lung tumors is perceived by many as the next frontier in non-surgical thermal tumor ablation but has been held back by lack of specialized equipment for creation of large enough volume of destroyed tissue at the targeted site. This limitation is additionally challenged by the necessity to operate through the working channel of the bronchoscope, by the difficulty of endoscopically navigating the ablation electrodes to targeted tumors and by the specific properties of lung tissue that is amply perfused by blood flow, cooled by perfusion, evaporation and convection, and incorporates a large volume of air that increases the RF path electrical impedance and can also deform the volume of targeted tissue in phase with breathing. The latter consideration led to research preference being given to microwave energy, since microwave energy travels through air well. However, there is an advantage of simplicity and efficiency in RF heating of tissues that are appreciated in the field.

In light of the foregoing there remains a need for improvements to RF energy delivery methods and devices that prove suitability for bronchoscope-delivered ablation of lung tumors. It is further desired for the devices to be flexible and relatively soft and fit in working channels that are small in diameter, preferable less than 2 mm, in order to reach tumors that are closer to the periphery of the lung.

SUMMARY

This disclosure is related to methods, devices, and systems for transbronchial ablation of a lung tumor. Aspects of the disclosure include:

Devices and systems suitable for delivering conductive fluid (e.g. HTS) into the airway through the endobronchial ablation catheter to reduce tissue impedance and increase the effective RF energy delivery electrode size.

Occluding the airway leading to the targeted tumor;

Surrounding or penetrating a tumor, peripheral or central, with ablation electrodes;

Ablating the tumor with RF ablation energy using monopolar, multiple monopolar, bipolar, multi-polar and multiphasic RF configurations;

Ablating the tumor with RF ablation energy and irrigating the RF electrodes, with normal or hypertonic saline, or other biocompatible conductive solutions (e.g. calcium chloride, magnesium chloride, sodium carbonate, sodium chloride, sodium citrate, sodium hydroxide, or sodium nitrate), and controlling the RF ablation energy with feedback from temperature sensors, irrigation saline concentration, temperature or flow rate or impedance;

Collapsing, compressing, air-volume reducing or partially collapsing a portion of a lung comprising a tumor to ablate the tumor;

Placing ablation catheters over guide wires and exchanging bronchoscope;

Placement of electrodes in airways using over the wire exchange of a bronchoscope and electrode catheter;

Placement of needle electrodes in tumors using spring-loaded or push-pull catheter handle designs;

Exchanging a guided biopsy tool with a non-guided or guided ablation tool upon a positive on-site biopsy result and maneuvering to the same biopsied location under fluoroscopy or ultrasound guidance;

Decreasing blood flow to the targeted region of lung by decreasing oxygen in said region and causing local hypoxic vasoconstriction prior to or during delivery of ablation energy.

Endobronchial navigation using CT image data to create a navigation plan to facilitate advancing an ablation catheter through a bronchoscope and a branch of a bronchus of a patient towards the nodule. Electromagnetic tracking may also be utilized in conjunction with the CT data to facilitate guiding the ablation catheter through the branch of the bronchus to the nodule. The ablation catheter may be positioned within one of the airways of the branched luminal networks adjacent to or within the nodule or point of interest. Once in position, fluoroscopy may be used to visualize the ablation catheter as it is further maneuvered towards the nodule or point of interest. Other imaging techniques, such as MRI, ultrasound, etc., may be used in conjunction with, or in lieu of, fluoroscopy or CT in combination with navigational bronchoscopy. Optionally, the endobronchial ablation catheter may be fitted with sensors (e.g. 3D electromagnetic coils, Fiber Bragg Grating shape sensors, etc.) compatible with the navigational bronchoscopy system available on site.

One or more aspects of the invention are disclosed here below.

A first aspect relates to a system for treatment of a target region of lung tissue, the system comprising: at least one a flow regulator configured to be interposed between a conductive fluid source and a conductive fluid outlet positionable at or in proximity of the target region of lung tissue, the flow regulator being further configured for controlling a flow rate or a bolus quantity of conductive fluid coming from the fluid source and delivered to the conductive fluid outlet; a controller communicatively connectable with said flow regulator and with at least one sensor, with the at least one sensor being configured for detecting values taken by at least one control parameter representative of a physical property, wherein the physical property is one of temperature (T), pressure (p), electric impedance (Z), or electric conductivity (C) of material present at or in proximity of the target region of lung tissue; wherein the controller is configured for:

receiving from said sensor signals representative of detected values of the control parameter;

controlling the flow regulator based on one or more detected values of the control parameter, wherein controlling the flow regulator comprises executing a control cycle including:

controlling the flow regulator in a high delivery mode, wherein in the high delivery mode:

the flow rate of conductive fluid delivered to the conductive fluid outlet is equal or above a set high flow rate, or the bolus quantity of conductive fluid delivered to the conductive fluid outlet is equal above a set high bolus quantity, controlling the flow regulator in a low delivery mode, wherein in the low delivery mode:

the flow rate of conductive fluid delivered to the conductive fluid outlet is equal or below a set low flow rate smaller than the set high flow rate, or the bolus quantity of conductive fluid delivered to the conductive fluid outlet is equal or below a set low bolus quantity smaller than the set high bolus quantity.

A $2^{nd}$ aspect according to the first aspect wherein in the low delivery mode: the flow rate of conductive fluid delivered to the conductive fluid outlet is equal or below a set low flow rate smaller than 50% of the set high flow rate, or the bolus quantity of conductive fluid delivered to the conductive fluid outlet is equal or below a set low bolus quantity smaller than 50% of the set high bolus quantity.

A $3^{rd}$ aspect according to the first aspect or $2^{nd}$ aspect, wherein in the low delivery mode the set low flow rate is between 0 and 5 ml/min or wherein the set low bolus quantity is between 0 and 10 ml.

A $4^{th}$ aspect according to the first or $2^{nd}$ or $3^{rd}$ wherein in the high delivery mode the set high flow rate is between 2 and 16 ml/min or the set high bolus quantity is between 0.3 and 60 ml.

A $5^{th}$ aspect according to any one of the first to $4^{th}$ aspects, wherein controlling the flow regulator comprises repeatedly executing said control cycle.

A $6^{th}$ aspect according to any one of the first to $5^{th}$ aspects, comprising at least one ablation element positionable at the target region of the lung tissue and connectable to an ablation source.

A $7^{th}$ aspect according to the $6^{th}$ aspect, comprising at least one flexible shaft configured to advance through an airway passage of a lung and having an active portion positionable at the target region of the lung tissue and including the at least one ablation element.

An $8^{th}$ aspect according to any one of the preceding first to $7^{th}$ aspects, comprising the at least one sensor, the sensor being configured to be positionable at the target region of the lung tissue.

A $9^{th}$ aspect according to the $7^{th}$ aspect in combination with any one of aspects 1-6 and 8, wherein the at least one sensor is carried by the active portion of said flexible shaft.

A $10^{th}$ aspect according to the $7^{th}$ aspect in combination with any one of aspects 1-6 and 8, wherein the at least one sensor is configured to be positioned in correspondence of a volume surrounding the active portion of said flexible shaft.

An $11^{th}$ aspect according to aspect 9 or 10, wherein the at least one sensor is configured for sensing values taken by the at least one control parameter, and wherein the physical property is one of temperature, pressure, electric impedance, or electric conductivity of material present in a volume surrounding the active portion.

A $12^{th}$ aspect according to any one of the preceding aspects comprising the conductive fluid outlet which is configured to be placed in fluid communication with the conductive fluid source.

A $13^{th}$ aspect according to aspect 7 and 12, wherein the conductive fluid outlet is carried by the flexible shaft active portion.

A $14^{th}$ aspect according to aspect 7 and 12, wherein the conductive fluid outlet is configured to be positioned in correspondence of said volume surrounding the active portion.

A $15^{th}$ aspect according to any one of the preceding aspects 6-14, wherein the controller is connectable with said ablation source and configured for controlling the ablation energy source to deliver ablation energy to the at least one ablation element.

A $16^{th}$ aspect according to the $15^{th}$ aspect, further wherein the controller is configured for executing said steps of: receiving from said sensor signals representative of sensed values of the control parameter, and controlling the flow regulator based on one or more sensed values of the control parameter and executing, optionally repeatedly executing, said control cycle, while the controller commands the ablation energy source to deliver ablation energy to the at least one ablation element.

A $17^{th}$ aspect according to any one of the preceding aspects 7-16, comprising an electrical connector carried by the flexible shaft and adapted to electrically connect the at least one ablation element to the ablation source.

An $18^{th}$ aspect according to any one of the preceding aspects, wherein the control cycle includes: verifying if one or more sensed values of the control parameter fall below a set low threshold (T_Low), and wherein said controlling the flow regulator to low delivery mode is executed if the one or more sensed values of the control parameter fall below the set low threshold (T_Low).

A $19^{th}$ aspect according to any one of the preceding aspects, wherein the control cycle includes: verifying if one or more sensed values of the control parameter exceed a set high threshold (T_High, Z_High), and wherein said controlling the flow regulator to high delivery mode is executed if the one or more sensed values of the control parameter exceed the set high threshold (T_High, Z_High).

A $20^{th}$ aspect according to any one of the preceding aspects, wherein the control cycle includes: periodically verifying if one or more sensed values of the control parameter fall below a set low threshold (T_Low), switching the flow regulator from high delivery mode to low delivery mode when the one or more sensed values of the control parameter fall below the set low threshold (T_Low); optionally, wherein said step of periodically verifying is executed at least 10 times per second.

A $21^{st}$ aspect according to any one of the preceding aspects, wherein the control cycle includes: periodically verifying if one or more sensed values of the control parameter exceed a set high threshold (T_High, Z_High), switching the flow regulator from low delivery mode to high delivery mode when the one or more sensed values of the control parameter exceed the set high threshold (T_High, Z_High); optionally, wherein said step of periodically verifying is executed at least 10 times per second.

A $22^{nd}$ aspect according to any one of the preceding aspects wherein the controller is configured for repeating the control cycle a plurality of times during a same treatment session.

A $23^{rd}$ aspect according to aspect 22, wherein the controller is configured to control the flow regulator in high delivery mode or in low delivery mode for a respective time interval, and wherein a duration of said respective time intervals is either predetermined or determined by detection of a triggering event.

A $24^{th}$ aspect according to aspect 23, wherein the controller is configured to determine duration of said time intervals by detection of a triggering event, wherein detection of the triggering event comprises one or more of:

detection that one or more values of the sensed parameter exceeds a set very high threshold (T_Overheat),
  detection that one or more values of the sensed parameter exceeds said set high threshold (T_High, Z_High),
  detection that one or more values of the sensed parameter falls below a set low threshold (T_Low).

A $25^{th}$ aspect according to aspect 22 or 23 or 24, wherein the controller is configured to execute the same treatment session which includes a plurality of time intervals where the flow regulator is adjusted to low delivery mode intercalated by time intervals where the flow regulator is adjusted to high delivery mode, thereby reducing the overall amount of conductive fluid delivered over said treatment session while maintaining under control the detected values of the parameter.

A $26^{th}$ aspect according to any one of the preceding aspects, wherein the step of controlling the flow regulator to low delivery mode comprises: adjusting the flow regulator to maintain the flow rate of conductive fluid to the conductive fluid outlet equal or below said set low flow rate during a low delivery time interval (Flow Low Time), in particular comprised between 1 to 10 seconds; or adjusting the flow regulator to deliver to the conductive fluid outlet the bolus quantity of conductive fluid equal or below said set low bolus quantity within a low delivery time interval (Flow Low Time), in particular comprised between 1 to 10 seconds.

A $27^{th}$ aspect according to aspect 26, wherein the cycle comprises a sub-routine optionally executed after expiration of said low delivery time interval, said sub-routine including:

a further step of verifying if one or more values of the sensed parameter falls below or above the set low threshold (T_Low),
  in case one or more values of the parameter sensed in the further step of verifying falls below the set low threshold (T_Low), assigning a decreased value to the set low flow rate or to the set low bolus quantity, and
  repeating controlling the flow regulator to low delivery mode using the decreased value of the set low flow rate or the decreased value of set low bolus quantity.

A $28^{th}$ aspect according to any one of the preceding aspects, wherein the step of controlling the flow regulator to high delivery mode comprises:

adjusting the flow regulator to maintain the flow rate of conductive fluid to the conductive fluid outlet equal or above said set high flow rate during a high delivery time interval (Flow High Time), in particular comprised between 1 to 30 seconds; or
  adjusting the flow regulator to deliver to the conductive fluid outlet the bolus quantity of conductive fluid equal or above said set high bolus quantity within a high delivery time interval (Flow High Time), in particular comprised between 1 to 30 seconds.

A $29^{th}$ aspect according to aspect 28, wherein the cycle comprises a sub-routine optionally executed after expiration of said high delivery time interval, said sub-routine including:

a further step of verifying if one or more values of the sensed parameter falls below or above the set low threshold (T_Low),
  in case one or more values of the parameter sensed in the further step of verifying remains above the set low threshold (T_Low), assigning an increased value to the set high flow rate or to the set high bolus quantity, and
  repeating controlling the flow regulator to high delivery mode using the increased value of the set high flow rate or the increased value of set high bolus quantity.

A $30^{th}$ aspect according to aspect 29, wherein the cycle provides for repeating the sub-routine of aspect 29 until when the further step of verifying if one or more values of the sensed falls below the set low-threshold (T_Low) is positively passed.

A $31^{st}$ aspect according to aspect 16 and 30, wherein the controller is configured to interrupt or reduce delivery of ablation energy to the at least one ablation element if it has determined that, after a predetermined number of repetitions of the subroutine of aspect 29, the step of verifying if one or more values of the sensed fall below the set low threshold (T_Low) is not positively passed.

A $32^{nd}$ aspect according to any one of the preceding aspects wherein the cycle comprises:

determining occurrence of a safety relevant event if the one or more parameter values are above a set over-high threshold (T_Over High; Z_Over High), which is greater than said high threshold (T_High; Z_High);
  if a safety relevant condition is determined, then:
    temporarily adjust down power supplied to the ablation energy source and/or
    control the flow regulator to a very high delivery mode, wherein in the very high delivery mode the flow rate of conductive fluid delivered to the conductive fluid outlet is equal or above a set very high flow rate greater than the set high flow rate, or the bolus quantity of conductive fluid delivered to the conductive fluid outlet is equal or above a very set high bolus quantity greater than the high bolus quantity.

A $33^{rd}$ aspect according to any one of the preceding aspects 6 to 32, wherein the controller is configured for maintaining power supplied by the ablation energy source in a range comprised between 20 and 200 W over a major portion of the treatment session, optionally over the entire treatment session.

A 34$^{th}$ aspect according to any one of preceding aspects 6-33, wherein the controller is configured to increase power supplied by the ablation energy source from an initial value to a regimen value, during an initial portion of the treatment session optionally lasting between 10% and 30% of the entire treatment session.

A 35$^{th}$ aspect according aspect 34, wherein the controller is configured to maintain power supplied by the ablation energy source at the regimen value during a major portion of the treatment session following said initial portion of the treatment session.

A 36$^{th}$ aspect according to aspect 35, wherein the initial value is comprised between 20 W and 80 W and wherein the regimen value is comprised between 40 W and 200 W, further wherein the initial value smaller than 80% of the regimen value, optionally smaller than 50% of the regimen value.

A 37$^{th}$ aspect according to any one of the preceding aspects 22-36 wherein the treatment session has a total treatment duration comprised between 30 seconds and 30 min.

A 38$^{th}$ aspect according to any one of preceding aspects 6-37, wherein the controller is configured to automatically stop delivery of power from the ablation energy source and automatically command the flow regulator to stop delivery of conductive fluid when the treatment duration has expired.

A 39$^{th}$ aspect according to any one of the preceding aspects 22-38, wherein the controller is configured to control the flow regulator to impose that: a maximum volume of conductive fluid delivered during the treatment session is comprised between 0.3 ml and 60 ml, and/or an average flow rate of conductive fluid maintained during the treatment session is of 0.1 to 15 ml/min, in particular wherein the controller is configured to automatically stop delivery of power from the ablation energy source and/or automatically command the flow regulator to stop delivery of conductive fluid when said maximum of conductive fluid delivered has been reached.

A 40$^{th}$ aspect according to any one of the preceding aspects 1-39 in combination with one of aspects 18-21, wherein the set high threshold (T_High) is greater than the set low threshold (T_Low).

A 41$^{st}$ aspect according to aspect 40 in combination with aspect 24, wherein the set very high threshold (T_Overheat) is greater than the set high threshold (T_High).

A 42$^{st}$ aspect according to any one of the preceding aspects, wherein the physical property is the temperature of material present at the target region, in particular when this aspect also depends upon aspect 11 the physical property is the temperature of material present in the volume surrounding the active portion.

A 43$^{rd}$ aspect according to aspects 40 and 42, wherein said set low threshold (T_Low) is 60 to 95° C.

A 44$^{th}$ aspect according to aspect 40 in combination with one of aspects 42 or 43, wherein said set high threshold (T_High) is from above 75° C. to 105° C.

A 45$^{th}$ aspect according to aspect 41 in combination with one of aspects 42 or 43 or 44, wherein said set very high threshold (T_Overheat) is between 85 to 115° C.

A 46$^{th}$ aspect according to any one of the preceding aspects 1-45, wherein the ablation energy source is a radiofrequency generator and wherein the controller is configured to control the radiofrequency generator to deliver RF, having a power in a range of 1 to 200 W, in particular comprised between 20 and 200 W, for a duration of 30 seconds to 30 minutes.

A 47$^{th}$ aspect according to any one of the preceding aspects 1 to 46, wherein the flow regulator comprises: a pump, optionally a syringe pump or a peristaltic pump or an infusion pump, or a valve.

A 48$^{th}$ aspect according to any one of the preceding aspects 7-47, comprising: a conductive fluid source configured to deliver a hypertonic saline solution; a fluid port connectable to the conductive fluid source and in fluid communication with the conductive fluid outlet, optionally, wherein the hypertonic saline solution includes a reverse phase transition polymer and water, which may transition to higher viscosity when transitioned from below body temperature to body temperature.

A 49$^{th}$ aspect according to aspect 48, wherein the hypertonic saline solution comprises one or more physiologically acceptable solutes and has a theoretical Osmolarity between 0.8 and 15 Osm/L, calculated according to the formula $$\text{Osmolarity} = \sum_{Each\,solute} (\text{molarity} \times n)$$

in which n is the number of particles that dissociate from each solute molecule; optionally wherein the hypertonic saline solution is a solution according to any one of aspects from 123 to 146.

A 50$^{th}$ aspect according to aspect 48 or 49, wherein the hypertonic saline solution comprises sodium chloride (NaCl) at a concentration of between 3% to 30% (w/v).

A 51$^{st}$ aspect according to any one of the preceding aspects 7-50, wherein the flexible shaft is the flexible shaft of an ablation catheter.

A 52$^{nd}$ aspect according to aspect 51, wherein the ablation catheter has a/the fluid port that is at a proximal end of the flexible shaft and is in fluid communication with the conductive fluid outlet which is located at the active portion of the flexible shaft.

A 53$^{rd}$ aspect according to any one of the preceding aspects 7-52, wherein the active portion is a distal end portion of the flexible shaft.

A 54$^{th}$ aspect according to any one of the preceding aspects 7-53 comprising at least one space occluder operative at or proximate to the flexible shaft active portion, in particular at or proximate to the flexible shaft distal end portion.

A 55$^{th}$ aspect according to aspect 54, wherein the space occluder is one of a tapered shaft section, a deployable balloon, a deployable valve, a deployable stent.

A 56$^{th}$ aspect according to aspect 54 or 55, wherein the occluder comprises a deployable occlusion balloon having a first cross section width of 1 to 30 mm, a length in a range of 5 to 30 mm, and wherein the occlusion balloon is configured to expand to occlude a portion of the airway.

A 57$^{th}$ aspect according to aspect 56, wherein the first cross section width is at a proximal region of the deployable occlusion balloon, a second cross section width in a range of 1 to 30 mm is at a distal region of the balloon, and a cross section width between the first and second cross section width is less than both the first and second cross section width.

A 58$^{th}$ aspect according to aspect 56, wherein the first cross section width is at a proximal region of the deployable occlusion balloon, and a second cross section width in a range of 1 to 20 mm and less than the first cross section width is at a distal region of the balloon.

A $59^{th}$ aspect according to any one of the preceding aspects 7-58, comprising a tubular sheath or bronchoscope receiving said flexible shaft, wherein at least the active portion, in particular the distal end portion, of the flexible shaft is configured to emerge from the tubular sheath or bronchoscope.

A $60^{th}$ aspect according to aspect 59, in combination with any one of aspects 54 to 58, wherein the space occluder is carried by the tubular sheath or bronchoscope.

A $61^{st}$ aspect according to any one of aspects 54 to 58, wherein the at least one space occluder is directly carried by the flexible shaft or by another shaft.

A $62^{nd}$ aspect according to any one of aspects 54 to 61, further comprising an inflating lumen extending through the flexible shaft and having a proximal end connectable to a source of a fluid, optionally a source of liquid or a source of gas, and a distal end in fluid communication with inside of the balloon.

A $63^{rd}$ aspect according to any one of the preceding aspects 7 to 62, wherein the flexible shaft comprises depth markers at least on 5 cm of the proximal region and 5 cm of the distal region.

A $64^{th}$ aspect according to any one of the preceding aspects 7 to 62, comprising at least one suction opening at the flexible shaft distal end portion configured to be placed in fluid communication with a vacuum source to aspirate air from a lung volume surrounding the distal end portion of the shaft.

A $65^{th}$ aspect according to aspect 64, in combination with any one of aspects 54 to 63, wherein the at least one suction opening is positioned distal with respect to the space occluder.

A $66^{th}$ aspect according to aspect 64, in combination with any one of aspects 54 to 63, comprising an additional space occluder operative at or proximate to the shaft distal end portion, in particular wherein the additional space occluder is one of a deployable balloon, a deployable valve, a deployable stent, and wherein the at least one suction opening is positioned between the space occluder and the additional space occluder.

A $67^{th}$ aspect according to aspect 65 or 66, wherein the at least one conductive fluid outlet is positioned distal with respect to the space occluder or between the space occluder and the additional space occluder.

A $68^{th}$ aspect according to any one of aspects 54 to 67, wherein the at least one sensor is positioned distal to the space occluder or between the space occluder and the additional space occluder.

A $69^{th}$ aspect according to aspect 67, wherein the at least one sensor is carried by the flexible shaft distal end portion and wherein the physical property is of one of temperature, pressure, electric impedance, or electric conductivity of material surrounding the distal end portion of the flexible shaft.

A $70^{th}$ aspect according to aspect 68 or 69, wherein the at least one sensor comprises a first sensor positioned proximal to the ablation element and a second sensor positioned distal to the ablation element.

A $71^{st}$ aspect according to any one of the preceding aspects 7 to 70, wherein the at least one ablation element comprises an ablation element having a rounded distal tip positioned at a distal tip of the flexible shaft.

A $72^{nd}$ aspect according to aspect 64, in combination with any of aspects 54 to 63 and 65 to 71, comprising: a common lumen extending through the flexible shaft and having a proximal end, selectively connectable to at least one of the source of the conductive liquid and the vacuum source, and a distal end, forming a common opening defining said at least one outlet and said at least one suction opening; or a dedicated irrigation lumen and a dedicated air suction lumen, with the irrigation lumen connected to the at least one outlet and extending through the catheter flexible shaft, the irrigation lumen having an inlet port configured to be connected to the source of conductive fluid, and with the air suction lumen connected to the at least one air suction opening and extending through the catheter flexible shaft, the air suction lumen having a suction port configured to be connected to the source of vacuum.

A $73^{rd}$ aspect according to any one of the preceding aspects 7-72, wherein the flexible shaft has an outer diameter less than or equal to 2 mm.

A $74^{th}$ aspect according to any one of the preceding aspects 7-73, wherein at least a portion of the flexible shaft is capable of turning such that a bend in the shaft has a radius of curvature of at least as 7 mm.

A $75^{th}$ aspect according to any one of the preceding aspects 7-74, wherein the flexible shaft has a length of at least 50 cm.

A $76^{th}$ aspect according to any one of the preceding aspects 7-75, wherein the elongated shaft has a guidewire lumen in the distal end portion configured to receive a guidewire.

A $77^{th}$ aspect according to aspects 72 and 76, wherein the suction lumen and guidewire lumen are formed by a common lumen.

A $78^{th}$ aspect according to any one of the preceding aspects 6-77, wherein the ablation element comprises at least one electrode characterized by one or more of the following features: total surface area not greater than 120 mm$^2$; diameter in a range of 0.5 to 2 mm; length in a range of 3 to 20 mm.

A $79^{th}$ aspect according to any one of the preceding aspects 6-78, wherein the at least one ablation element includes at least two electrodes, and wherein a separation between electrodes is between five to fifteen mm.

An $80^{th}$ aspect according to any one of the preceding aspects including an interface component connectable with said at least one sensor and at least communicatively connectable with the controller to transfer to the controller the detected values of said at least one control parameter detected by the sensor.

An $81^{st}$ aspect according to any one of the preceding aspects, wherein the controller is configured for:

processing said sensed values, and based on one or more of said sensed values, generating at least one output signal which comprises one or more of:

a user identifiable output, optionally the user identifiable output comprising an audible signal, a visual signal or a vibratory signal signaling to the user to deploy at least one space occluder operative at or proximate to the shaft distal end portion, a status output, indicative of the degree of air volume reduction of a lung portion located at a/the catheter distal end portion, an output command automatically deploying at least one space occluder operative at or proximate to a/the shaft distal end portion, a temperature output providing an indication of the temperature of material surrounding a/the distal end portion of a/the flexible shaft, an electric property output providing an indication of the impedance or conductivity of material surrounding a/the distal end portion of the shaft, a pressure output providing an indication of the pressure of material surrounding a/the distal end portion of a/the flexible shaft.

An $82^{nd}$ aspect according to any one of the preceding aspects, wherein the controller is configured to:

receive signals from the at least one sensor, said sensor being a temperature sensor configured to:

monitor temperature at said target region, and control the conductivity or the composition of the conductive fluid delivered through said at least one outlet based on the monitored temperature to maintain the temperature values detected by the temperature sensor within a determined temperature range or above a certain temperature threshold.

An 83rd The system of any one of the preceding aspects, wherein controller configured to:

receive signals from the at least one sensor, said sensor being a temperature sensor, in particular when this aspect depends upon aspect 7 said sensor being configured for detecting values of temperature of material surrounding the distal end portion of the flexible shaft, monitor temperature at the target region, and adjust the ablation energy power output by the energy source to maintain the temperature values detected by the temperature sensor within a determined temperature range or above a certain temperature threshold.

An $84^{th}$ aspect according to aspect 82 or 83, wherein the determined temperature range is between 60 and 115° C. and the certain temperature threshold is at least 80° C.

An $85^{th}$ aspect according to any one of the preceding aspects 1-84, further comprising a navigation sensor, such as a three-dimensional navigation sensor, or a shape sensor, such as a Fiber Bragg Grating sensor, on at least the distal end region, in particular wherein the navigation sensor is one or more of an electromagnetic sensor, a 3D electromagnetic sensor, shape sensor, FBG sensor, a 3D ultrasound sensor, and an impedance tracking for 3D navigation.

An $86^{th}$ aspect according to any one of the preceding aspects 7-85, further comprising a perforation element at a distal tip of the flexible shaft configured to advance through a tumor, wherein the perforation element is selected from a list comprising a needle, a deployable needle, and an RF perforation electrode.

An $87^{th}$ aspect according to any one of the preceding aspects 6-87 in combination with aspect 54, wherein a distance between the space occluder and the ablation element is in a range of 1 mm to 40 mm.

An $88^{th}$ aspect relates to an ablation catheter comprising:

a flexible shaft configured to advance through airway passages of a lung;

at least one ablation element, positioned at a distal end portion of the flexible shaft and electrically connectable to an ablation energy source;

a fluid port connectable to a conductive fluid source; and at least one outlet for conductive fluid, the outlet being located at said distal end portion and being in fluid communication with the fluid port.

An $89^{th}$ aspect according to aspect 88 further comprising at least one space occluder operative at or proximate to the shaft distal end portion, in particular wherein the space occluder is one of a tapered shaft section, a deployable balloon, a deployable valve, or a deployable stent.

A $90^{th}$ aspect according to aspect 89, wherein the occluder comprises a deployable occlusion balloon having a first cross section width of 1 to 30 mm, a length in a range of 5 to 30 mm, and wherein the occlusion balloon is configured to expand to occlude a portion of the airway.

A $91^{st}$ aspect according to aspect 90, wherein the first cross section width is at a proximal region of the deployable occlusion balloon, a second cross section width in a range of 1 to 30 mm is at a distal region of the balloon, and a cross section width between the first and second cross section width is less than both the first and second cross section width.

A $92^{nd}$ aspect according to aspect 90, wherein the first cross section width is at a proximal region of the deployable occlusion balloon, and a second cross section width in a range of 1 to 20 mm and less than the first cross section width is at a distal region of the balloon.

A $93^{rd}$ aspect according to aspect 88 to 92, comprising a tubular sheath or bronchoscope receiving said shaft, wherein at least the distal end portion of the flexible shaft is configured to emerge from the tubular sheath or bronchoscope.

A $94^{th}$ aspect according to aspect 93 in combination with aspect 90, wherein the space occluder is carried by the tubular sheath or bronchoscope or wherein the at least one space occluder is directly carried by the shaft or by a different shaft.

A $95^{th}$ aspect according to any of aspects 88 to 94 in combination with aspect 90, further comprising an inflating lumen extending through the flexible shaft and having a proximal end connectable to a source of a fluid, optionally a source of liquid or a source of gas, and a distal end in fluid communication with inside of the balloon.

A $96^{th}$ aspect according to any of aspects 88 to 95, wherein the flexible shaft comprises depth markers at least on 5 cm of the proximal region and 5 cm of the distal region.

A $97^{th}$ aspect according to any of aspects 88 to 96, comprising at least one suction opening at the shaft distal end portion configured to be placed in fluid communication with a vacuum source to aspirate air from a lung volume surrounding the distal end portion of the shaft.

A $98^{th}$ aspect according to aspect 97 in combination with aspect 90, wherein the at least one suction opening is positioned distal with respect to the space occluder.

A $99^{th}$ aspect according to aspect 98 comprising an additional space occluder operative at or proximate to the shaft distal end portion, in particular wherein the additional space occluder is one of a deployable balloon, a deployable valve, a deployable stent, a tapered shaft section, and wherein the at least one suction opening is positioned between the space occluder and the additional space occluder.

A $100^{th}$ aspect according to any of aspects 88 to 99, wherein the at least one conductive fluid outlet is positioned distal with respect to the space occluder or between the space occluder and the additional space occluder.

A $101^{st}$ aspect according to any of aspects 88 to 100 further comprising at least one sensor positioned distal to the space occluder or between the space occluder and the additional space occluder.

A $102^{nd}$ aspect according to aspect 101 wherein the at least one sensor is carried by the distal end portion of the flexible shaft and wherein the physical property is of one of temperature, pressure, electric impedance, or electric conductivity of material surrounding the distal end portion of the flexible shaft.

A $103^{rd}$ aspect according to any of aspects 101 or 102 wherein the at least one sensor comprises a first sensor positioned proximal to the ablation element and a second sensor positioned distal to the ablation element.

A $104^{th}$ aspect according to any of aspects 88 to 102 wherein the at least one ablation element comprises an ablation element having a rounded distal tip positioned at a distal tip of the flexible shaft.

A 105$^{th}$ aspect according to aspect 97, in combination with any of aspects 88 to 103, comprising:

a common lumen extending through the flexible shaft and having a proximal end, selectively connectable to at least one of the source of the conductive liquid and the vacuum source, and a distal end, forming a common opening defining said at least one outlet and said at least one suction opening; or a dedicated irrigation lumen and a dedicated air suction lumen, with the irrigation lumen connected to the at least one outlet and extending through the catheter shaft, the irrigation lumen having an inlet port configured to be connected to the source of conductive fluid, and with the air suction lumen connected to the at least one air suction opening and extending through the catheter shaft, the air suction lumen having a suction port configured to be connected to the source of vacuum.

A 106$^{th}$ aspect according to any of aspects 88 to 105, wherein the flexible shaft has an outer diameter less than 2 mm.

A 107$^{th}$ aspect according to any of aspects 88 to 106, wherein at least a portion of the flexible shaft is capable of turning such that a bend in the shaft has a radius of curvature of at least 7 mm.

A 108$^{th}$ aspect according to any of aspects 88 to 107, wherein the flexible shaft has a length of at least 50 cm.

A 109$^{th}$ aspect according to any of aspects 88 to 108, wherein the elongated shaft has a guidewire lumen in the distal end portion configured to receive a guidewire.

A 110$^{th}$ aspect according to any of aspects 105 and 109, wherein the suction lumen and guidewire lumen are formed by a common lumen.

A 111$^{th}$ aspect according to any of aspects 88 to 110, wherein the ablation element comprises at least one electrode characterized by one or more of the following features:

total surface area not greater than 120 mm$^2$;

diameter in a range of 0.5 to 2 mm;

length in a range of 3 to 20 mm.

A 112$^{th}$ aspect according to any of aspects 88 to 111, wherein the at least one ablation element includes at least two electrodes, and wherein a separation between electrodes is between five to fifteen mm.

A 113$^{th}$ aspect according to any of aspects 88 to 112, in combination with aspect 101, including an interface component connectable with said at least one sensor and at least communicatively connectable with a controller to transfer to the controller values of said at least one control parameter detected by the sensor.

A 114$^{th}$ aspect according to any of aspects 88 to 113 in combination with aspect 101, comprising a controller configured for:

processing said sensed values, and based on one or more of said sensed values, generating at least one output signal which comprises one or more of:

a user identifiable output, optionally the user identifiable output comprising an audible signal, a visual signal or a vibratory signal signaling to the user to deploy at least one space occluder operative at or proximate to the shaft distal end portion, a status output, indicative of the degree of air volume reduction of a lung portion located at the distal end portion of the flexible shaft.

an output command automatically deploying at least one space occluder operative at or proximate to the distal end portion of the flexible shaft, a temperature output providing an indication of the temperature of material surrounding the distal end portion of the flexible shaft, an electric property output providing an indication of the impedance or conductivity of material surrounding the distal end portion of the flexible shaft, a pressure output providing an indication of the pressure of material surrounding the distal end portion of the flexible shaft.

A 115$^{th}$ aspect according to any one of aspects 88 to 114, in combination with aspect 101, comprising a controller configured to: receive signals from the at least one sensor, said sensor being a temperature sensor configured to monitor temperature at said target region; and control the conductivity or the composition of the conductive fluid delivered through said at least one outlet based on the monitored temperature to maintain the temperature values detected by the temperature sensor within a determined temperature range or above a certain temperature threshold.

A 116$^{th}$ aspect according to any one of the preceding aspects 88 to 115, wherein the controller is configured to: receive signals from the at least one sensor, said sensor being a temperature sensor, in particular when this aspect depends upon aspect 7 said sensor being configured for detecting values of temperature of material surrounding the distal end portion of the flexible shaft; monitor temperature at the target region; and adjust the ablation energy power output by the energy source to maintain the temperature values detected by the temperature sensor within a determined temperature range or above a certain temperature threshold.

A 117$^{th}$ aspect according to any of aspects 115 or 116, wherein the determined temperature range is between 60 and 115° C. and the certain temperature threshold is at least 80° C.

A 118$^{th}$ aspect according to any one of the preceding aspects 88 to 117, further comprising a navigation sensor, such as a three-dimensional navigation sensor, or a shape sensor, such as a Fiber Bragg Grating sensor, on at least the distal end region, in particular wherein the navigation sensor is one or more of an electromagnetic sensor, a 3D electromagnetic sensor, shape sensor, FBG sensor, a 3D ultrasound sensor, and an impedance tracking for 3D navigation.

A 119$^{th}$ aspect according to any of aspects 88 to 118, further comprising a perforation element at a distal tip of the flexible shaft configured to advance through a tumor, wherein the perforation element is selected from a list comprising a needle, a deployable needle, and an RF perforation electrode.

A 120$^{th}$ aspect according to any of aspects 89 to 119, wherein a distance between the space occluder and the ablation element is in a range of 1 mm to 40 mm.

A 121$^{st}$ aspect according to any of aspects 88 to 120, comprising a tapered distal end, a lumen passing through the shaft from the proximal region to the distal region, wherein the lumen exits the distal region at the narrowest part of the tapered distal end.

A 122$^{nd}$ aspect relates to a system comprising the catheter of aspect 121 and a tumor perforating wire adapted to be advanced through the lumen passing through the shaft from the proximal region to the distal region and beyond the distal region, the tumor perforating wire comprising a sharp distal tip, optionally a depth marker on a proximal region and optionally a radiopaque marker on a distal region.

A 123$^{rd}$ aspect relates to a solution for treatment of lung cancer, in particular non-small cell lung cancer (NSCLC), in a lung airway target region wherein:

the solution comprises one or more physiologically acceptable solutes and has a theoretical Osmolarity between 0.8 and 15 Osm/L, calculated according to the formula and/or $$Osmolarity = \sum_{Each\ solute} (molarity \times n)$$

in which n is the number of particles that dissociate from each solute molecule, sodium chloride (NaCl) at a concentration of between 3% to 30% (w/v), said solution reaches a temperature in the range of 60 to 115° C. in the target region of the lung airway, said solution is locally delivered to the target region via the airway, said solution is delivered at a non-constant flow rate to the target region, and said solution is delivered to the target region for a total treatment time comprised between 30 seconds and 30 minutes.

A 124$^{th}$ aspect according to aspect 123, wherein said solution is a hypertonic saline solution.

A 125$^{th}$ aspect according to any one of aspects from 123 or 124, wherein said solution has a conductivity, at sea level and 20° C., of at least 30 mS/cm preferably comprised between 70 mS/cm and 225 mS/cm.

A 126$^{th}$ aspect according to any one of the aspects from 123 to 125, wherein the total volume of solution delivered during said total treatment time is comprised between 0.3 ml and 60 ml.

A 127$^{th}$ aspect according to any one of aspects from 123 to 126, wherein delivering the said solution at a non-constant flow rate to the target region comprises alternating intervals in a low delivery mode and intervals in a high delivery mode, wherein during the low delivery mode interval, flow rate is maintained between 0 and 10 ml/min or a bolus quantity is delivered between 0 and 10 ml, and wherein in the high delivery mode interval, flow rate is maintained between 2 and 16 ml/min or a bolus quantity is delivered between 0.3 and 60 ml.

A 128$^{th}$ aspect according to any one of aspects from 123 to 127, wherein delivering the said solution at a non-constant flow rate to the target region comprises maintaining an average flow rate of conductive fluid during said treatment time comprised between 0.1 and 15 ml/min.

A 129$^{th}$ aspect according to any one of aspects from 123 to 128, wherein the hypertonic saline solution is locally delivered to the target region via the airway while delivering RF ablation energy, having a power in a range of 1 to 200 W, in particular comprised between 20 and 200 W.

A 130$^{th}$ according to any one of aspects from 123 to 129, wherein the saline solution includes a reverse phase transition polymer and water, which transitions from a lower viscosity to a higher viscosity when transitioned from below body temperature to body temperature.

A 131$^{st}$ aspect according to any one of aspects from 123 to 130, wherein the said solution composition is delivered to the target region, with the target region of lung sequestered by inflating a first occluding balloon in the natural airway leading to the target region, wherein the balloon is proximal to the target region of lung.

A 132$^{nd}$ aspect according to any one of aspects from 123 to 131, wherein the said solution is delivered to the target region, with the target region of lung sequestered by inflating, a second occluding balloon in the said natural airway distal to the first occluding balloon and distal to the target region.

A 133$^{rd}$ aspect according to any one of aspects from 131 or 132, wherein the said solution is delivered to the target region, while the one or both balloons occlude the natural airway and form a portion of the airway in which the said solution is injected and suppress flow of the liquid outside of that portion of the airway.

A 134$^{th}$ aspect according to any one of aspects from 123 to 133, wherein said solution has a theoretical Osmolarity between 0.8 and 15 Osm/L, preferably between 5 and 9 Osm/L.

A 135$^{th}$ aspect according to any one of aspects 123, or from 125 to 134, wherein said one or more solutes are selected among physiologically acceptable salts and inorganic hydroxides, preferably selected from the group of any of the following aqueous solutions or combinations thereof: calcium chloride, magnesium chloride, sodium carbonate, sodium chloride, sodium citrate, sodium hydroxide, or sodium nitrate.

A 136$^{th}$ aspect according to any one of aspects from 123 to 134, wherein the solution is a hypertonic saline solution which comprises sodium chloride (NaCl) at a concentration of 3% to 30% (w/v) and water.

A 137$^{th}$ aspect according to aspect 136, wherein the solution is a hypertonic saline solution which comprises a sodium chloride (NaCl) at a concentration of between 5% to 25% (w/v).

A 138$^{th}$ aspect according to any one of aspects from 136 or 137, wherein the solution comprises components different from water and sodium chloride at a weight/volume concentration below 1%.

A 139$^{th}$ aspect according to any one of aspects from 123 to 138, wherein the target region is formed by cancer tissue and has a volume of between 0.1 to 30 cm$^3$, in particular from 0.5 to 15 cm$^3$.

A 140$^{th}$ aspect according to any one of aspects from 123 to 139, wherein said solution is used during a procedure with a total treatment time which is function of the volume of the target region.

A 141$^{st}$ aspect according to any one of aspects from 123 to 141, wherein said solution is used during a procedure with a total treatment time of less than 7 minutes and wherein said solution is used for treating a target region of approximately less than 2 cm diameter.

A 142th aspect according to any one of aspects from 123 to 140, wherein said solution is used during a procedure with a total treatment time of less than 10 minutes and wherein said solution is used for treating a target region of approximately 2 cm diameter.

A 143th aspect according to any one of aspects from 123 to 140, wherein said solution is used during a procedure with a total treatment time of less than 15 minutes and wherein said solution is used for treating a target region of at least 2 cm diameter.

A 144th aspect according to any one of aspects from 123 to 140, wherein said solution is used during a procedure with a total treatment time of less than 30 minutes and wherein said solution is used for treating a target region greater than 3 cm diameter.

A 145$^{th}$ aspect according to any one of aspects from 123 to 144, wherein said solution directly contacts the target region.

A 146th aspect according to any one of aspects from 123 to 145, wherein the solution is delivered to the airway target region using the system of any one of the preceding aspects 1 to 87 or using the catheter of any one of the preceding aspects 88 to 122.

A 147$^{th}$ aspect relates to a system for treatment of a target region of lung tissue, the system comprising: a flow regulator configured to be interposed between a conductive fluid source and a conductive fluid outlet positionable at or in proximity of the target region of lung tissue, the flow regulator being further configured to control a flow rate or a bolus quantity of the conductive fluid coming from the fluid source and delivered to the conductive fluid outlet; a controller configured to control the flow regulator and configured to receive values detected by a sensor, wherein the sensor detects values of a control parameter representative of a physical property which is at least one of: temperature (T), pressure (p), electric impedance (Z), and electric conductivity (C) of material present at or in proximity of the target region of lung tissue; wherein the controller is configured to: receive one or more of the values of the control parameter; control the flow regulator based on the one or more of the values of the control parameter, wherein the control the flow regulator comprises executing a control cycle including: controlling the flow regulator in a high delivery mode in which the flow rate of the conductive fluid delivered to the conductive-fluid outlet is no less than a set high flow rate, or the bolus quantity of conductive fluid delivered to the conductive fluid outlet is no less than a set high bolus quantity, and controlling the flow regulator in a low delivery mode in which the flow rate of the conductive fluid delivered to the conductive fluid outlet is no greater than a set low flow rate smaller than the set high flow rate, or the bolus quantity of the conductive fluid delivered to the conductive fluid outlet is no greater than a set low bolus quantity smaller than the set high bolus quantity.

A 168$^{th}$ aspect relates to a method of treating a target region of lung tissue comprising: delivering ablative energy to the target region; delivering conductive fluid to the target region during the delivery of the ablative energy; sensing values of a control parameter that is at least one of a temperature (T), a pressure (P), an electric impedance (Z), and an electric conductivity (C) proximate to the target region, and controlling the delivery of the conductive fluid by: (i) controlling a flow rate or a bolus of the conductive fluid based on the sensed values of the control parameter; (ii) while operating in a high delivery mode, controlling the flow rate to be above a set high flow rate, or controlling the bolus to be above a set high bolus quantity, and (iii) while operating in a low delivery mode, controlling the flow rate to be below a set low flow rate or controlling the bolus to be below a set low bolus quantity, wherein the set low flow rate is lower than the set high flow rate, or the set low bolus quantity is less than the set high bolus quantity.

BRIEF DESCRIPTION OF THE DRAWINGS

FIGS. 14A, 14B, 14C and 14D are schematic illustrations of various embodiments of obturators of ablation catheters.

DETAILED DESCRIPTION

The present disclosure is directed generally to devices and methods for ablating malignant lung tumors and more particularly to ablating lung tumors with an approach through the patient's airway. An approach through the patient's airway may also be referred to as a transbronchial or endobronchial approach and comprises delivering medical devices through passageways by which air passes through the nose or mouth to the alveoli of the lungs. The term airway refers to any of the anatomical lumens of the respiratory system through which air passes including the trachea, bronchi, and bronchioles.

Figure 1:
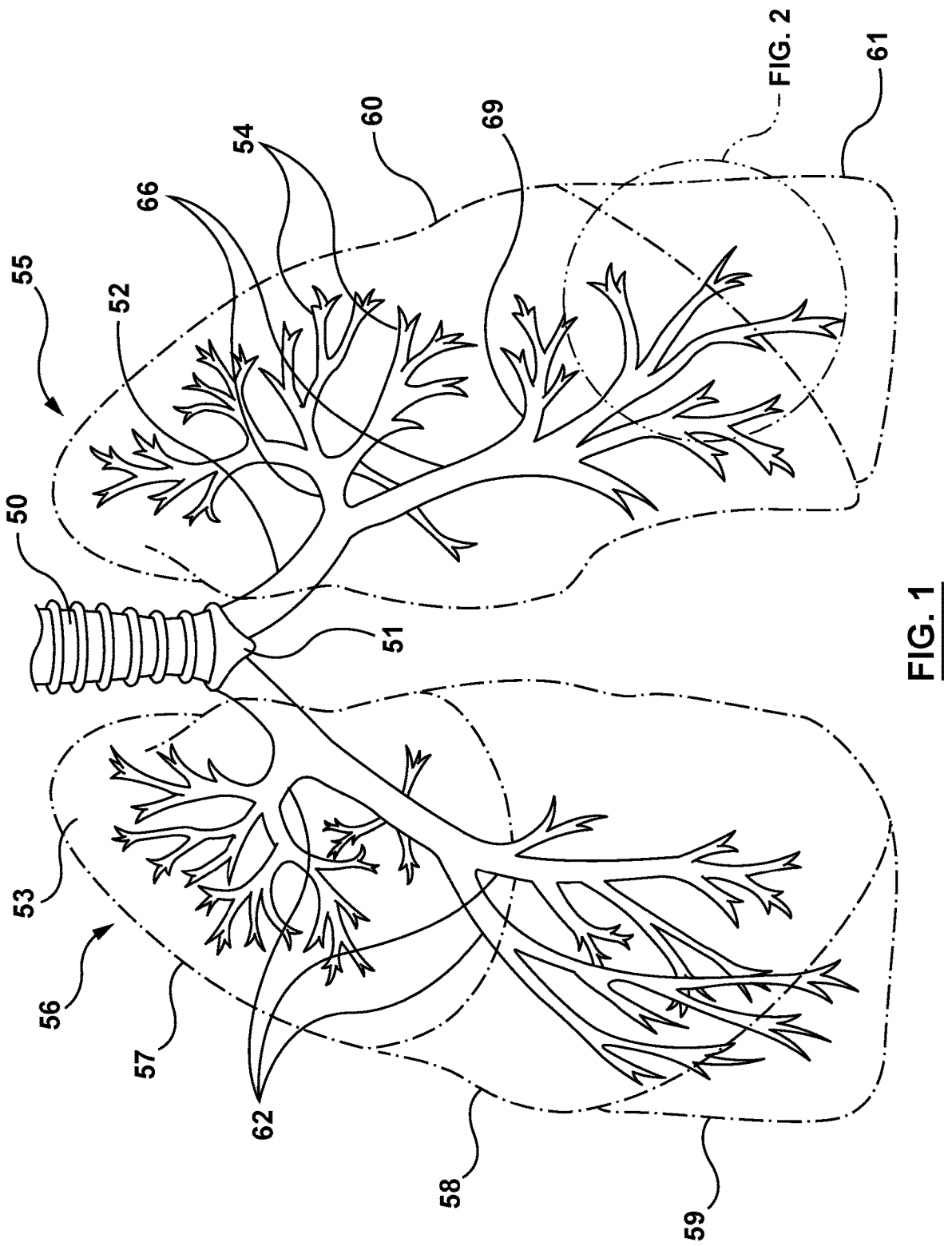
FIG. 1 is a schematic illustration of part of a human respiratory system.
Figure 2:
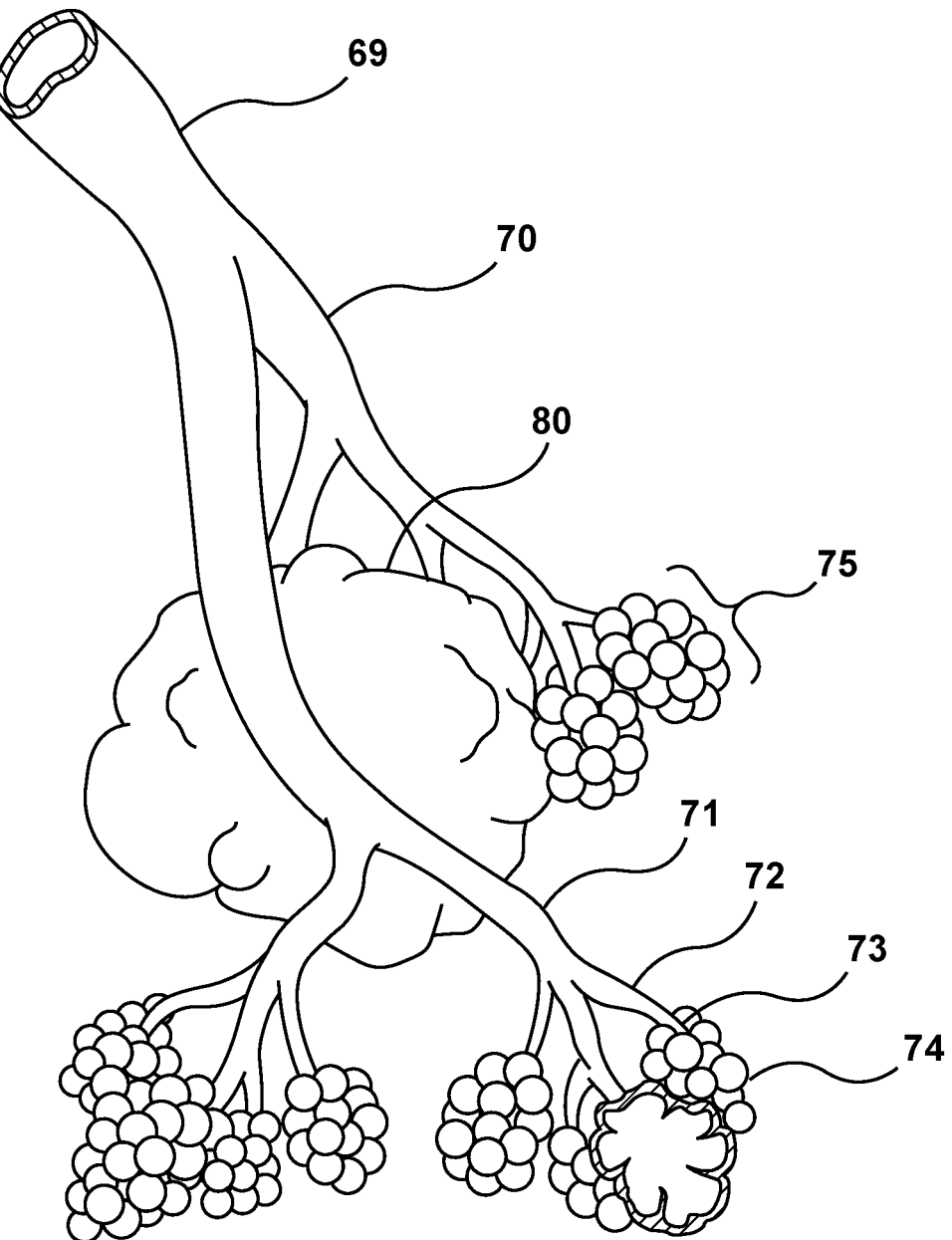
FIG. 2 is a closer view of a section of FIG. 1.

FIG. 1 is a schematic illustration of part of a patient's respiratory system including the trachea 50, carina of trachea 51, left main bronchus 52, right main bronchus 53, bronchioles 54, alveoli (not shown, residing in bunches at the end of bronchioles), left lung 55, right lung 56. The right main bronchus subdivides into three secondary bronchi 62 (also known as lobar bronchi), which deliver oxygen to the three lobes of the right lung—the superior lobe 57, middle lobe 58, and inferior lobe 59. The left main bronchus divides into two secondary 66 or lobar bronchi to deliver air to the two lobes of the left lung—the superior 60 and the inferior 61 lobes. The secondary bronchi divide further into tertiary bronchi 69, (also known as segmental bronchi), each of which supplies a bronchopulmonary segment. A bronchopulmonary segment is a division of a lung separated from the rest of the lung by a septum of connective tissue (not shown). As shown in FIG. 2 the tertiary bronchi 69 divide into many primary bronchioles 70, which divide into terminal bronchioles 71, each of which then gives rise to several respiratory bronchioles 72, which go on to divide into two to eleven alveolar ducts 73. There are five or six alveolar sacs 75 associated with each alveolar duct. Alveolar sacs are made up of several alveoli 74. The alveolus 74 is the basic anatomical unit of gas exchange in the lung. FIG. 2 also shows a peripherally located tumor 80 positioned in a space external to and amongst the bronchioles. A targeted tumor 80 may reside peripherally, centrally, or within a lymph node or airway wall of a lung or mediastinum.

There are two major types of lung cancer, non-small cell lung cancer (NSCLC) and small cell lung cancer (SCLC). Non-small cell lung cancer accounts for about 85 percent of lung cancers and includes: Adenocarcinoma, the most common form of lung cancer in the United States among both men and women, are formed from glandular structures in epithelial tissue and usually forms in peripheral areas of the lung; Squamous cell carcinoma, which accounts for 25 percent of all lung cancers and is more typically centrally located; Large cell carcinoma, which accounts for about 10 percent of NSCLC tumors. The focus of this disclosure is on treating NSCLC, which may occur peripherally among bronchioles, centrally among bronchi, or in lymph nodes. However, the devices, systems and methods disclosed herein may also be used for ablating or treating other diseases of the lung as well.

An aspect of the disclosure provides a method for treating a lung tumor of a patient. A pathway to a point of interest in a lung of a patient is generated. It is anticipated that in the majority of patients with a solitary nodule an airway can be identified on CT leading to the target suitable for positioning of an ablation energy delivery element proximate, for example within 1 cm, of the target. Using a pre-acquired CT as a map a flexible instrument can be threaded through the airways by a bronchoscopist using known and existing tools. In one embodiment, an extended working channel is advanced through the airway into the lung and along the pathway to the point of interest. The extended working channel is positioned in a substantially fixed orientation at the point of interest. Anchoring mechanisms may be used to secure stability of the channel. A catheter may be advanced though the extended working channel to the targeted region of the lung. A working channel may be for example a lumen through a delivery sheath or through a bronchoscope, both of which may be steerable or incorporate a guidewire lumen. Optionally, a delivery sheath may be an endobronchial ultrasound delivery sheath that generates and ultrasound image of tissue around the distal end of the sheath. A portion of the lung containing the targeted region may be occluded and at least having its corresponding air volume reduced, for example by occluding an airway feeding the portion (e.g., using at least an occluding element such as a balloon on the catheter or delivery sheath) and applying negative pressure to the lung portion or other means for collapsing a portion of lung disclosed herein. To confirm air volume reduction in the portion of lung, electrodes on the catheter may be used to measure tissue impedance or phase. A complete collapse of the targeted lung portion is not necessary. Experimental observations show that an air volume reduction in the targeted lung portion, which produces a 5 to 20% decrease in the respective bipolar impedance, is sufficient for the purpose of facilitating effective ablation energy delivery. The lung tissue is treated with the ablation catheter at the targeted region of the lung by injecting hypertonic saline, or other types of biocompatible conductive salts or solutions (e.g. calcium chloride, magnesium chloride, sodium carbonate, sodium chloride, sodium citrate, sodium hydroxide, or sodium nitrate, etc.), through the catheter in to the targeted portion of lung and applying RF energy from one or more electrodes on the catheter. Optionally, more than one ablation catheter may be delivered to the targeted region of lung and an RF circuit may be made between electrode(s) on a first catheter to electrode(s) on a second catheter. In the presented embodiments of this disclosure RF electrodes are used to deliver ablation energy.

An extended working channel may be positioned within a patient, optionally through a bronchoscope or as part of a bronchoscope. A locatable guide may be positioned within the extended working channel for positioning the extended working channel to the point of interest. Biopsy tools may be advanced to the point of interest. Prior to advancing the biopsy tool through the extended working channel, the locatable guide may be removed from the extended working channel. Alternatively, navigation-guided extended working channels may be used in conjunction with 3-D navigation systems, such those offered by Veran Medical or superDimension™ (Medtronic), or robotically delivered bronchoscopic working channels may be used, such as those offered by Intuitive Surgical or Auris Health. For example, the navigated instrument (e.g. the catheter of this disclosure) may be fitted with shape sensors, such as Fiber Bragg Grating (FBG) sensors. The use of such shape sensors inside ablation catheters is described in "FBG Sensor for Contact Level Monitoring and Prediction of Perforation in Cardiac Ablation" by Ho et al. Sensors 2012, 12, 1002-1013, incorporated herein by reference. The lung tissue may be biopsied. If the biopsy is confirmed positive, then the lung tissue may be ablated. The biopsy tool is retracted and replaced with an ablation catheter or tool comprising at least one energy delivery element. This method may facilitate positioning of the energy delivery elements of the ablation catheter or tool at the same place where the biopsy is taken. Prior to treating the lung tissue, the placement of the ablation catheter at the point of interest may be confirmed, for example visually using a bronchoscope and identifying the point of interest with respect to elements of the airway. The lung tissue or tumor may be penetrated at the point of interest. Effective treatment of the lung tissue may be confirmed, for example by obtaining a post ablation biopsy or assessing the impedance or phase of the treated tissue using electrodes or sensors on the ablation catheter.

With the current resolution of CT scanners, at least seven or eight, likely more, generations of airways can be imaged and evaluated. There are reasons to believe that the imaging resolution will rapidly improve further. If the trachea is the beginning point and if a pulmonary parenchymal nodule is the targeted end-point, then appropriate software can interrogate the three-dimensional image data set and provide a pathway or several pathways through the adjacent airways to the target. The bronchoscopist can follow this pathway during a real or navigational bronchoscopy procedure and the correct airway pathway to the nodule can be quickly cannulated using a wire, a bronchoscope and a thin wall polymer tube or channel or sensed/navigational bronchoscopy instruments.

Once the access channel is in place, then multiple probes can be placed either to biopsy, or to ablate the identified tumor. Ultrathin bronchoscopes can be used in a similar manner. In conjunction with navigational bronchoscopy tools, using these sorts of approaches, majority of peripheral lung lesions can be destroyed.

Currently available fiberoptic bronchoscopes (FOBs) have an illumination fiberoptic bundle and imaging fiberoptics or a camera. Except for the very few "ultrathin" bronchoscopes, there is also a channel for suction of secretions and blood, for the passage of topical medication and fluid for washing, and for the passage of various instruments for diagnostic retrieval of tissues or for therapeutic procedures. A typical diagnostic bronchoscope has an outer diameter of 5.0 to 5.5 mm and an operating channel of 2.0 to 2.2 mm. This caliber channel admits most cytology brushes, bronchial biopsy forceps, and transbronchial aspiration needles with sheathed outer diameters between 1.8 and 2.0 mm Smaller bronchoscopes, in the range of 3.0 to 4.0 mm at the outer diameter and correspondingly smaller channels, are usually given a "P" designation (for pediatrics), but they can be used in the adult airways. Newer generations of slim video and fiberoptic bronchoscopes have a 2.0 mm operating channel with a 4.0 mm outer diameter. The one disadvantage of these bronchoscopes is the sacrifice of a smaller image area because of fewer optical bundles. The ultrathin bronchoscopes generally have outer diameters smaller than 3 mm. For example, Olympus models BF-XP40 and BF-XP160F (Olympus America, Center Valley, PA) have outer diameters of 2.8 mm and operating channels of 1.2 mm Special instruments (e.g., reusable cytology brush and forceps) of the proper calibre are available for tissue sampling. Current generations of video bronchoscopes are all built with a 60 cm working length. These bronchoscopes are suitable for accessing distal airways to place the guide wire over which a delivery channel or an energy delivery catheter can be exchanged.

Navigation bronchoscopy (NB) consists of two primary phases: planning and navigation. In the planning phase previously acquired CT scans are utilized to mark and plan pathways to targets within the lung. In the navigation phase, these previously planned targets and pathways are displayed and can be utilized for navigation and access deep within the lung. Upon arriving at the target NB enables multiple applications all within the same procedure. CT scans of the patient's chest are loaded into proprietary software that reconstructs the patient's airways in multiple 3D images. The physician utilizes these images to mark target locations and plan pathways to these target locations within the lungs. Using the planned pathway created in the planning phase and real-time guidance, the physician navigates a sensed probe and extended working channel to the desired target location(s). Once at the desired location, the physician locks the extended working channel in place and the sensed probe is removed. The extended working channel provides access to the target nodule for bronchoscopic tools or catheters.

Reducing Air Volume in a Portion of Targeted Lung Tissue

The lungs are divided into five lobes as shown in FIG. 1, including the right upper lobe 57, right middle lobe 58, right lower lobe 59, left upper lobe 60, and left lower lobe 61. The lobes are in turn divided into segments. Each lobe or segment is generally autonomous and receives its own bronchus and pulmonary artery branch. If an airway supplying a lobe or a segment is occluded with a one-way valve or occluded with an obturator and the air is sucked out it will collapse or reduce in volume leading to local tissue compression under the pressure exerted by the rest of the lung. Unlike most tissues in the body susceptible to tumors, lung tissue is intrinsically highly compliant, compressible and ultimately collapsible. Atelectasis refers to a complete or partial collapse of a lung, lobe or portion of a lung. When an airway is blocked, there is no, or reduced, negative pressure delivered to that target portion of the lung. Therefore, the neighboring portions or segments compress it and remove the entrapped air. Alternatively, or additionally, vacuum suction may be applied through a lumen in the blocking device (e.g. balloon). The vacuum can be used to further remove the air out of the targeted lung portion. As a result, further or more efficient collapsing may be achieved. For the purposes of this disclosure the phrase "collapsing a portion of lung" refers to compressing or reducing the corresponding air volume or shrinking the portion of lung and complete collapse is not necessarily the intention. Without more air, the sac shrinks. It is understood that in some cases collateral ventilation may re-inflate the collapsed segment but it is expected that tissue shrinking from building up heat and continuous suction can overcome, at least partially, the re-inflation of the target area. Balloons may be used to seal the entry to a target airway when inflated. A lumen through the balloon may be used to provide the additional vacuum suction.

Lung compliance is an important characteristic of the lung. Different pathologies affect compliance. Particularly relevant to cancer ablation are the observations that: fibrosis is associated with a decrease in pulmonary compliance; emphysema/COPD may be associated with an increase in pulmonary compliance due to the loss of alveolar and elastic tissue; and pulmonary surfactant increases compliance by decreasing the surface tension of water. The internal surface of the alveolus is covered with a thin coat of fluid. The water in this fluid has a high surface tension and provides a force that could collapse the alveolus. The presence of surfactant in this fluid breaks up the surface tension of water, making it less likely that the alveolus can collapse inward. If the alveolus were to collapse, a substantial force would be required to open it, meaning that compliance would decrease drastically. Atelectasis, clinically defined as collapse of the lung area visible on X-ray, is generally not desired. However, localized lung collapse can be beneficial in the treatment of emphysema and, as the authors propose, targeted lung cancer ablation. Advantages to collapsing or air volume reducing the targeted lung portion that contains a targeted tumor during tumor ablation may include the following: electrodes positioned in airways surrounding the tumor may be drawn closer to the tumor, thereby improving concentration of ablative energy or increasing efficacy of ablating the tumor; air will be removed from the collapsed, or shrunk lung tissue supplied by the airway making the delivery of ablative energy and the thermal propagation more efficient; collapse of the segment may lead to hypoxia that provoke regional hypoxic pulmonary vasoconstriction and ischemia of the lung segment which reduces metabolic cooling and improves efficient utilization of the thermal energy; the spread of irrigation fluid, such as hypertonic saline, may be confined to the targeted area, thereby providing virtual-electrode ablation outcomes mostly to the target region. However, complete lung, lung lobe or lung segment collapse is not necessary for the intent of this invention. Bronchial air volume reduction via vacuum application to the catheter is, typically, sufficient in improving the electrical contact between the RF electrode and the bronchial wall. This, in turn, increases the safety and reduces the ineffectiveness of energy delivery which may be caused by evaporation of irrigation fluid (caused by overheating) or by its inadvertent spread to neighboring tissues; and electrode contact with tissue may be more consistent or have greater surface area of contact. Furthermore, ablative energy such as radiofrequency electrical energy may be delivered by a computer-controlled ablation console and collapsing the lung portion may improve temperature-controlled ablation performance by increasing contact stability and pressure between the tissue and electrode(s). For example, in a collapsed or shrunk airway, temperature sensor(s) positioned in or on the electrode(s) may provide more accurate temperature feedback to the computer-controlled ablation console used to control the energy delivery parameters such as RF power, RF power ramp up slope, or duration, while increased contact stability and pressure may allow increased stability of thermal and electrical conduction allowing the temperature sensor(s) to have a more accurate representation of temperature of the tissue around the electrode. Consequently, the ablative energy delivered to the targeted lung tissue and tumor may be optimized and the temperature of the targeted tissue may be heated to an intended temperature set point in an effective and safe manner.

Air volume reduction in one lobe or a segment or other section of a lung defined by morphology of airways and air supply by airways can be impeded by collateral interlobular ventilation that is common in patients with incomplete interlobar fissures and partially damaged and destroyed lung. Alternative methods of segmental or lobar collapse can be employed by heating lung tissue or injecting chemicals, foam or hot steam into the targeted segment or the targeted lobe. For example, injection of hot steam into a contained space like lobe or segment results in collapsing the space. The nature of the lung is such that when a segment is collapsed, pressurized adjacent segments compress it and fill the volume vacated by the collapsed space. Techniques for collapsing or partially collapsing portion of the lung that has collateral air pathways using a bronchoscope and broncho-scope delivered tools are described for example in U.S. Pat. No. 7,412,977 B2. Partial lung collapse, particularly of an upper lobe, was previously proposed to imitate results of lung reduction surgery in advanced emphysema but has not been suggested to enhance thermal ablation (e.g. RF) of tumors. Techniques proposed included: occluders and valves, steam (e.g., thermal), foam, and glue injection into airways. Mechanical compression of a lung portion using springs or wire coils was proposed also. All these methods can be envisioned as being modified and adopted for cancer therapy in any lobe or segment where the tumor was located on CT and identified as malignant. As mentioned above, partial lung or lung region collapse is not required to implement successfully the present invention. The goal is to reduce bronchial air volume so to enhance electrode-tissue contact.

Ultimately an entire lung can be temporarily collapsed using a technique of independent lung ventilation. Lungs are intubated and ventilated by separate endotracheal tubes with obturators of the two main bronchi. A patient that is healthy enough to tolerate it can breathe using mechanical ventilation of only one lung while the contralateral lung is being collapsed and operated on. Electrodes can be positioned prior to deflating and collapsing the lung. In this case collateral ventilation will not have much effect on the ability of the operator to collapse the lung.

Reducing the air volume of a portion of targeted lung may provide other advantages that facilitate tumor ablation by enhancing RF ablation lesion dimensions. Air in the lung's airway is a very poor thermal conductor and electrical conductor. Collapsing the airways (e.g., by occluding air-flow or with other methods described herein) deflates them, which enhances the permeability of RF through the previously aerated tissue. We therefore propose reducing the air volume in a target lung portion as a means to facilitate improved energy delivery through electrodes combined with a device such as an endobronchial catheter. A balloon (e.g., filled with liquid or air), another space occluder, a deployable valve, injected steam, a fan, glue injection, or stent could be used to occlude the airway to reduce the air volume of a specific lung portion encompassing or next to the targeted tumor. The balloon, for example, may be used to occlude a portion of the airway and as the airway is blocked, the blood absorbs the gas inside the alveoli thus reducing the air volume. Alternatively, the entrapped air may be sucked out using vacuum pressure through a lumen in the catheter. The suction may be applied for 30 s to 10 min, depending on the level of shrinkage or collapse desired. If the airway is deprived of air the alveoli shrink. In some cases, blood, fluids and mucus may fill, at least partially, the previously aerated space, allowing the space to conduct RF energy and heat more effectively.

In addition, collapse of the segment leads to hypoxia that leads to regional hypoxic vasoconstriction of the lung. Reduced blood flow to the targeted region of the lung results in less blood velocity and metabolic cooling and more efficient utilization of the thermal energy.

A procedural method of ablating a lung tumor comprising collapsing a targeted portion of the lung with a catheter configured to occlude an airway and ablate tissue may comprise the following steps: identifying the location of a targeted tumor in a lung (e.g., using medical imaging technology such as CT); Generating a 3D navigation map by registering the medical images with navigation technology; delivering a bronchoscope through the patient's airway placing the distal end in a vicinity of the targeted lung portion optionally using 3D navigation or electromagnetic navigation assistance; taking a biopsy to confirm tumor position; lubricate the bronchoscope, occlusion-ablation catheter and endotracheal tube lumen; placing the occlusion-ablation catheter through the bronchoscope working channel; steering the catheter's distal region to the targeted site navigating (e.g. by standard, virtual or navigation bronchoscopy) the ablation electrode as close to the tumor as possible optionally comprising delivering the catheter over a guidewire; optionally confirming electrode position or contact using impedance measured from the electrode, imaging or EM navigation; optionally positioning the occlusion balloon in the airway proximal to the ablation site; inflating the occlusion balloon while visualizing with the broncho- scope's lens; optionally allowing air volume reduction in the targeted portion of lung as air is absorbed or apply other bronchial air volume reduction steps as disclosed herein (e.g., apply suction to remove air from the targeted lung portion); optionally monitoring electrical impedance of tissue (e.g., between the RF electrode(s) and a grounding pad, or between bipolar RF electrodes) wherein a stable, consistent impedance indicates the bronchial air volume has been reduced, thus making greater tissue contact with the electrode(s) (e.g., in a study conducted by the authors impedance dropped about 24% to 38% when the bronchial air volume was reduced); irrigating the electrode(s) or infusing conductive fluid into the targeted lung portion; delivering computer-controlled ablation energy through the electrode(s) to the targeted tissue; optionally removing fluid remaining in the lung portion through the catheter, or through a bronchoscope; deflating the occlusion balloon and removing the catheter from the patient; visualizing the treated airway for signs of hemorrhage or blistering, which may be treated if required. Optionally, subsequent ablations may be made at vacuum suction was more successful in reducing the bronchial air volume. As a result, the zone of white opacity 800 is spread, encompassing a larger zone around the catheter RF electrode 234. This observation also correlated well with the change measured in catheter bipolar impedance. At baseline, prior to suction, the bipolar impedance read 670Ω. After vacuum application, the bipolar impedance dropped to 400Ω, which represents a 40% drop from the baseline. A bipolar-impedance drop from baseline in the range of 5 to 50% is typically sufficient in supporting improved electrical contact between the bronchial wall and the RF electrode 234. To further improve the quality of the electrical contact between the RF electrode and the targeted bronchial wall, small amounts of hypertonic saline are released prior to RF delivery. For example, in the cases illustrated in FIGS. 18A and 18B, the release of 23.4% hypertonic saline at a rate of 5 ml/min for a duration of 5 s decreased the catheter bipolar impedance down to 140Ω and 130Ω, respectively. Preferably, without limitations to the scope of this invention, prior to delivery of RF energy, the bipolar impedance should be decreased to less than 300Ω. As shown in Table 1, the larger bronchial air volume reduction (FIG. 18B), which resulted in improved RF electrode contact, produced a larger ablation volume (listed in Table 1 as Width_1, Width_2, and Length). The increased ablation volume was not a sole consequence of the larger bronchial air volume reduction. Increased hypertonic saline flow rates, likely the result of local blood and air flow conditions, created a larger virtual RF electrode. The larger virtual RF electrode, as expected, contributed to forming a larger ablation zone.

TABLE 1

Figure 18B:
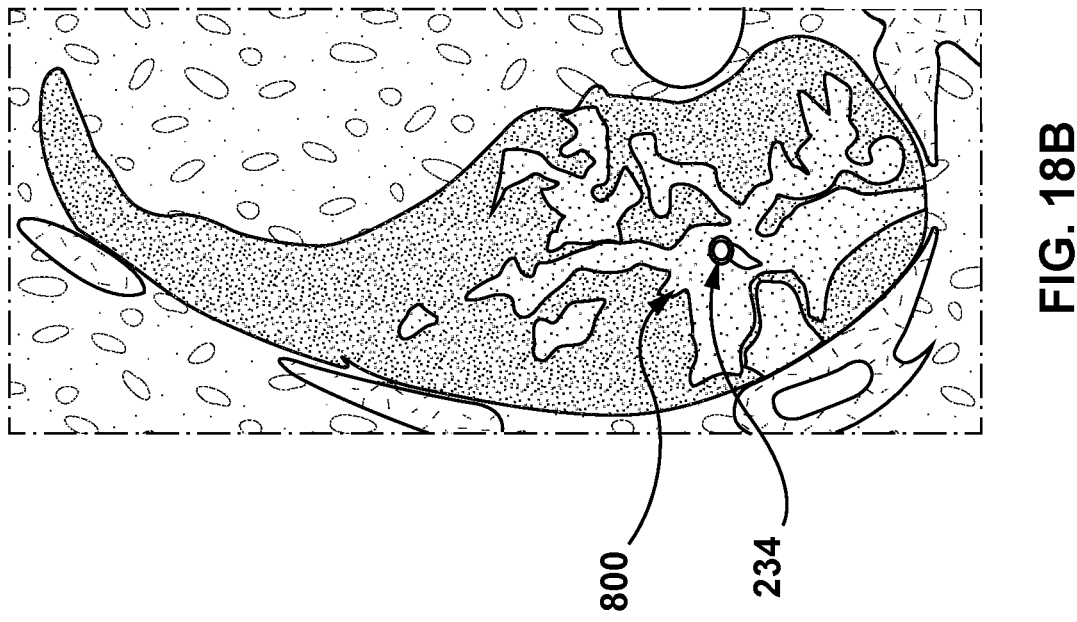
FIG. 18B is an illustration of a CT image of a catheter placement with higher-level of air volume reduction, as evidenced by the larger white opacity area, in the targeted airway.
Figure 18A:
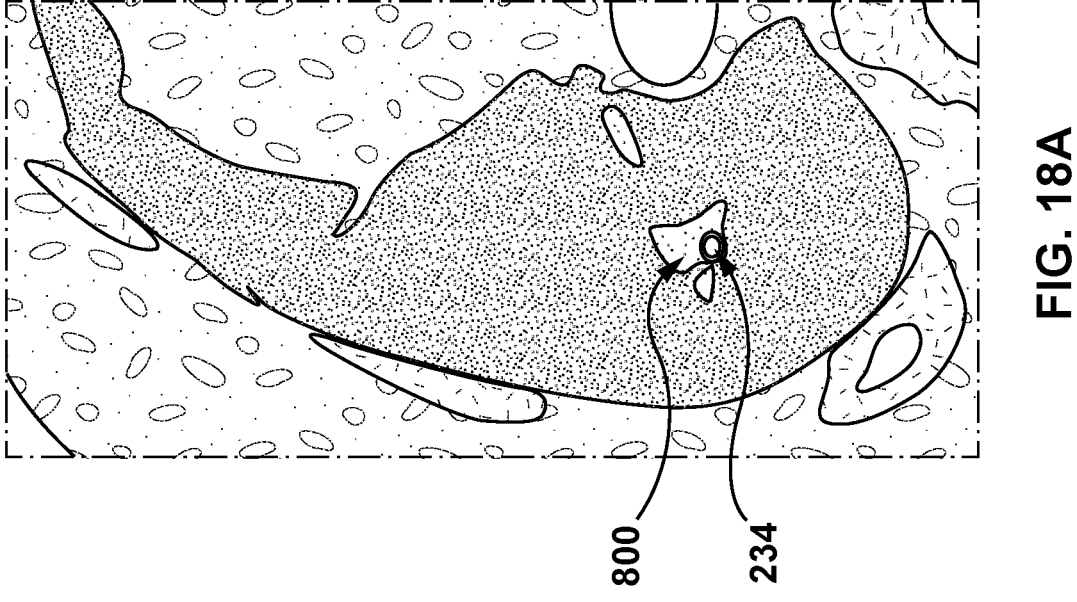
FIG. 18A is an illustration of a CT image of a catheter placement with low-level of air volume reduction, as evidenced by the small area of white opacity, in the targeted airway.

| | Power [W] | Impedance [Ω] | Temperature [C.] | HS average flow rate (ml/min) | RF duration (min) | Width 1 [mm] | Width 2 [mm] | Length [mm] |
|---|---|---|---|---|---|---|---|---|
| FIG. 18A | 67 | 92 | 84 | 0.5 | 6 | 24 | 23 | 15 |
| FIG. 18B | 67 | 79 | 90 | 2.5 | 6 | 44 | 31 | 39 | different locations by moving the ablation electrode to the subsequent location. If previously collapsed, it may be necessary to let the lung portion inflate before moving the ablation electrode if it is difficult to relocate the electrode while the lung portion is collapsed. In some situations, it may be possible to keep the lung portion deflated and optionally infused with conductive fluid while relocating the electrode(s). Optionally, fiduciary markers may be placed in or around the tumor to later locate the tumor using CT to determine if it was successfully ablated or to apply a subsequent ablation.

FIGS. 18A and 18B are illustrations of CT images of a lung during animal studies and show examples of situations where there were varying degrees of bronchial air volume reduction. In FIG. 18A, vacuum suction was less efficient in relatively reducing the bronchial air volume. As a consequence, the zone of white opacity 800 (which indicates a volume of lung tissue affected by the removal of bronchial air) is limited in size, concentrated only in the space surrounding the RF electrode 234. This observation correlated very well with the relative drop in the catheter bipolar impedance (measured between proximal electrode 237 and RF electrode 234—see FIG. 4A). At baseline, prior to application of catheter vacuum suction, the bipolar impedance was 590Ω. After vacuum suction application, the bipolar impedance did not change, remaining at 590Ω. Conversely, FIG. 18B shows a situation where catheter Delivery of Conductive Fluid into the Targeted Lung Portion Conductive fluid may be delivered (e.g., via a lumen of an ablation catheter) to the airway in the targeted portion of lung to enhance RF ablation. The delivery of conductive fluid may be a volume infusion of hypertonic saline (e.g., hypertonic saline having concentrations in a range of 5% to 30%) to enhance endobronchial lung tumor ablation by ablating a larger volume of tissue (e.g., ablations greater than or equal to 1.5 cm in diameter). Other conductive fluids may be used. For example, several biocompatible aqueous conductive solutions (e.g., conductive solutions that are not per se lethal or toxic to the living body) such as calcium chloride, magnesium chloride, or sodium hydroxide may be used. Such solutions, in by-volume concentrations of 10% or higher, have an electrical resistivity in the range of 2-35 Ω·cm, preferably in the range of 4-14 Ω·cm (70-225 mS/cm if expressed as conductivity), low enough to support effective conduction of radiofrequency current. Osmolarity is an important characteristic of such aqueous solutions, which can be computed as:

$$\text{Osmolarity} = \sum_{Each\,solute} (\text{molarity} \times n)$$

where n is the number of particles that dissociate from each solute molecule. For example, the osmolarity of various solutions can be determined as follows:

1) for a solution of 23.4% by volume of Na Cl (molecular weight of 58.44 g/mol) molarity is: 23.4 g/100 ml/58.44 g/mol=0.4 mol/100 ml=4 mol/L Given that NaCL dissociates in $Na^+$ and $Cl^-$, it results that n=2. Hence, osmolarity equals Osm=4 mol/l*2=8 Osm/L 2) for a solution 10% by volume of $CaCl_2$ (molecular weight of 110.98 g/mol) molarity is: 10 g/100 ml/110.98 g/mol=0.09 mol/100 ml=0.9 mol/L Given that $CaCl_2$ dissociates in $Ca_2^+$ and $2Cl^-$, it results that n=3. Hence, osolarity equals Osm=0.9 mol/l*3=2.7 Osm/L Higher-osmolarity solutions may be preferred. In the calculation of the theoretical osmolarity of the saline solution the osmotic coefficient $\varphi$ is =1

Figure 4A:
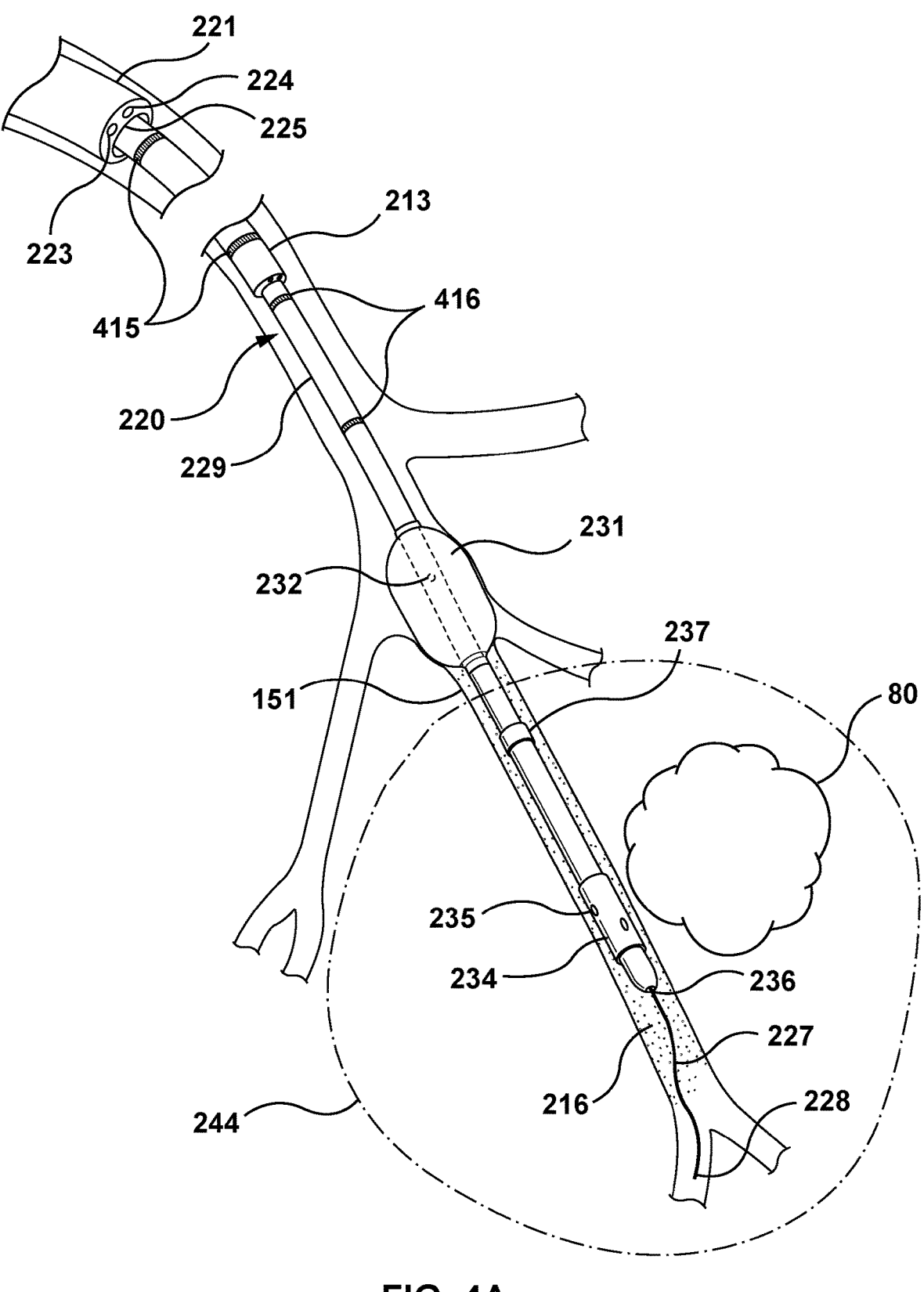
FIG. 4A is a schematic illustration of the device of FIG. 3 in situ.

Optionally, a conductive fluid may have a high viscosity or may be injected in a low viscosity state to a target region and transition to a higher viscosity state in the targeted region of the body. For example, ionic salts such as NaCl or others, such as those listed above, may be mixed with a reverse phase transition polymer and water, which may transition to higher viscosity when transitioned from below body temperature to body temperature. The polymer with appropriate characteristics may be one such as a block-co-polymer PLGA-PEG-PLGA consisting of polyethylene glycol, which is covalently esterified by an FDA-approved poly lactic-co-glycolic acid on both ends. Other examples of polymers may be based on polyethylene glycol, albumin, silk, wool, chitosan, alginate, pectin, DNA, cellulose, poly-sialic acids, dendritic polylysine, poly (lactic-co-glycolic) acid (PLGA), gellan, polysaccharides and poly-aspartic acid, and combinations thereof. The mixture may be designed to preserve the high electrical conductivity of the hypertonic saline base, while adding the higher viscosity properties of the polymer. This way, better control can be asserted over the spread of the conductive fluid. The polymer may be biodegradable, biocompatible or bioabsorbable. The ionic component may include for example, M.sup.+ X.sup.− or M.sup.2+Y.sup.2−, where M belongs to alkaline or alkaline earth metal such as Li, Na, K, Rb, Cs and X represents halogens, acetate and other equivalent counter balance to M.sup.+, and Y can be X.sub.2 or mixed halogens, acetates, carbonate, sulfate, phosphate and other equivalent counter balance to M.sup.2+, as well as formic acid, glycolic acid, lactic acid, propionic acid, caproic acid, oxalic acid, malic acid, citric acid, benzoic acid, uric acid and their corresponding conjugate bases. A conductive fluid may further comprise ingredients such as pharmaceutical agents (e.g., anticancer or antibiotic) to aid tissue healing or further treatment of cancerous cells, or radiopaque contrast. The volume infused may be sufficient to infuse beyond the targeted airway and in to the alveoli and lung parenchyma. This is achieved by conducting the delivered ablation energy (e.g., RF or microwave) to more tissue than the surface of the electrode contacts, thus, in effect, increasing the effective electrode size (i.e. creating a virtual electrode) and creating more stable and consistent electrical contact with the tissue. A conductive fluid, such as hypertonic saline, or others listed above, may also make ablation energy delivery more efficient, as less power is lost in saline and more delivered to the tissue. Less power is lost into hypertonic saline compared to physiological saline because hypertonic saline has a significantly increased electrical conductivity, and therefore lower contact impedance. With less power being lost into hypertonic saline, the boiling point is less likely to be reached. Therefore, ablations produced with hypertonic saline in a lung portion with reduced bronchial air volume tend to not show char formation and yet produce larger lesions. Injection of conductive fluid may be done with methods and devices as described herein for injection and optional concomitant retraction of fluid and optionally with collapsing of the targeted lung portion around the electrode(s). An example of a device 220 configured to occlude the targeted portion of lung to collapse the lung portion and ablate with an irrigated electrode is shown in FIG. 4A and comprises at least one electrode 234 with at least one irrigation port 235. As shown in Table 1, the greater hypertonic saline flow rate during the 6 minute RF delivery described in FIG. 18B resulted in a larger ablation volume. As presented in FIG. 17 and related text, the flow of hypertonic saline during RF delivery is controlled by the algorithm aspect of this disclosure. While the algorithm intends to optimize the overall amount of hypertonic saline, a minimum amount is required in order to produce ablation volumes of sizes suitable to treat lung cancer. For example, without limitation to the scope of this disclosure, the low flow rate of 0.5 ml/min from the case described in FIG. 18A resulted in a smaller ablation volume. It is preferred to achieve, during RF delivery, flow rates in excess of 0.2 to 0.5 ml/min Hypertonic saline flow rate above a maximum (e.g., a maximum of about 15 ml/min) may not result in larger ablation volumes, as the saline will reach a point when it ineffectively dissipates the RF energy. Hence, the algorithm of FIG. 17A will optimize the hypertonic saline flow rate to keep its overall volume below a maximum, yet larger than the minimum described above. Hypertonic saline flow rates in the range of 0.2 to 5 ml/min, preferably in the range of 1.5 to 2.5 ml/min, are expected to be effective in producing sufficiently large ablation volumes. An average flow rate of conductive fluid maintained during the treatment session may be in a range of 0.1 to 15 ml/min.

Animal experiments have shown a combination of infusing hypertonic saline into an airway and delivering thermal energy to the airway by way of radiofrequency has an impressive effect of killing tissue as seen on CT scans taken 2 weeks following the procedure. Some previous studies have shown that hypertonic saline could significantly attenuate tumor cell adhesion to endothelium by inhibiting adhesion molecule and laminin expression. (Shields C J1, Winter D C, Wang J H, Andrews E, Laug W E, Redmond H P. Department of Academic Surgery, Cork University Hospital and National University of Ireland, Wilton. Hypertonic saline impedes tumor cell-endothelial cell interaction by reducing adhesion molecule and laminin expression. Surgery. 2004 July; 136(1):76-83.) This may halt the metastatic behavior of tumor cells shed at surgery. Other researches have reported similar studies of using saline to trigger cell apoptosis. The researchers had a study of using salt to kill cancer cells. They have created a technique which can cause cancer cells to self-destruct by injecting them with salt. (Busschaert, N., Park, S., Baek, K., Choi, Y., Park, J., Howe, E., Hiscock, J., Karagiannidis, L., Marques, I., Felix, V., et al (2017). A synthetic ion transporter that disrupts autophagy and induces apoptosis by perturbing cellular chloride concentrations. Nature Chemistry, 9(7), 667-675.) (Ko, S., Kim, S, Share, A., Lynch, V., Park, J., Namkung, W., Van Rossom, W., Busschaert, N., Gale, P., et al (2014). Synthetic ion transporters can induce apoptosis by facilitating chloride anion transport into cells. Nature Chemistry, 6(10), 885-892.) Unfortunately, when a cell becomes cancerous, it changes the way it transports ions across its cell membrane in a way that blocks apoptosis. However, it should be expected that increasing temperature can increase diffusivity of hypertonic saline (HTS) and thus the ability to transport HTS into the cells, and it could be a highly potential direction that the infusing of heated HTS or other salines may have beneficial effect of killing tumor cells. As discussed above, other biocompatible, conductive, aqueous solutions may be employed. A higher osmolarity will support better diffusivity of ions across cellular membranes.

Hot hypertonic saline (HTS), or any other hot solution from those discussed above, has better performances in the osmosis or diffusion to transport HTS with respect to cells, and can increase promotion of cell dehydration. The increased extra-cellular salinity results in loss of water content from within neighboring cells. As a consequence, the hot HTS bolsters the cell desiccation effects produced by the delivery of RF energy. Comparatively, a study done with a standard, off-the-shelf ablation catheter (ThermoCool) powered at 50 W and irrigated with room-temperature saline, at high irrigation rates (30 ml/min), resulted in much less cell death. The HTS with a concentration above 5%, for example 10%, can be infused to the target space and then, as RF currents travel through it into tissue, reaches up to certain temperatures, for example in a range of 60° C. to 115° C., by the electrodes located on the distal area of the catheter. Alternatively, the sequestered portion of the lung can be irrigated with heated HTS from the irrigation port on the catheter directly. The sequestered portion can be exposed to heat and HTS for a duration of at least 2 minutes, or for a duration in a range of 30 seconds to 30 minutes accordingly, after which the HTS and the local area can be cooled down by shutting down the electrodes, irrigating or replacing with room temperature saline, or evacuated from the irrigation port directly. The procedure can be repeated until desired ablation results are achieved. It should be expected that increasing temperature can increase diffusivity of HTS and thus the ability to transport HTS into the cells, and it could be a highly potential direction that the infusing of heated HTS or other salines may have beneficial effect of killing tumor cells.

Figure 19A:
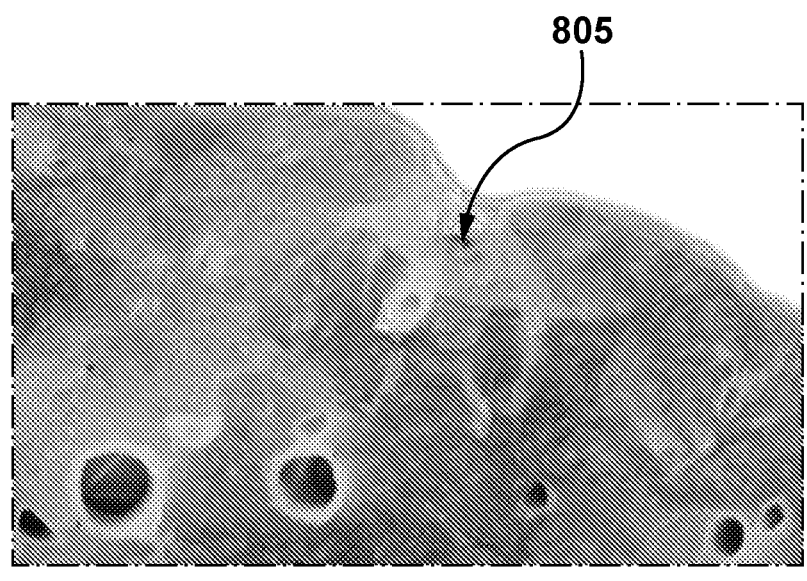
FIG. 19A is a gross pathology view of a cross-section through the lower left lobe showing a very small zone of necrotic tissue at 1 month after infusion of hypertonic saline. No RF energy was applied.
Figure 19B:
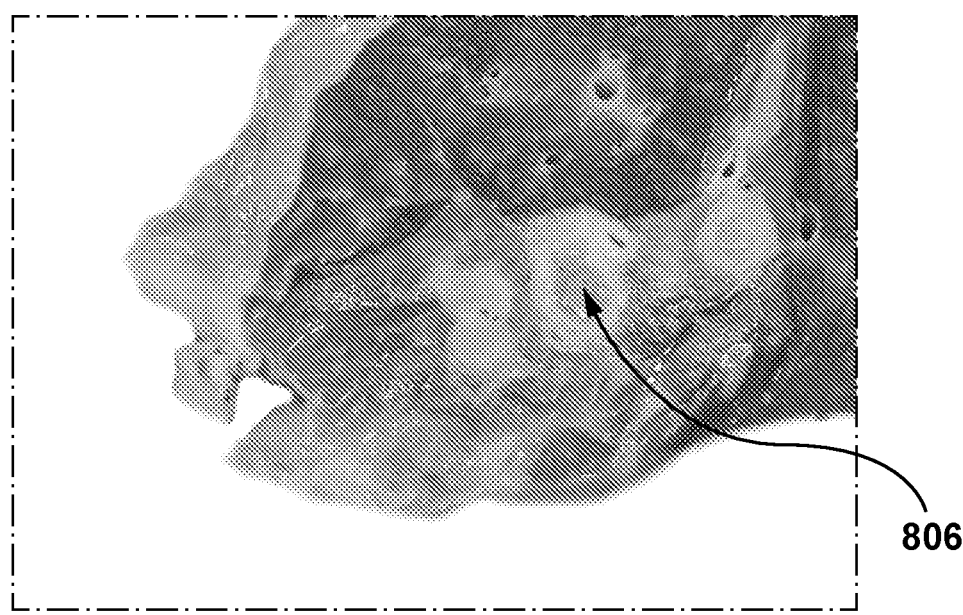
FIG. 19B is gross pathology view of a cross-section through the lower right lobe showing a larger zone of necrotic tissue at 1 month after treatment, which consisted of combined infusion of hypertonic saline and 90 s RF delivery.

FIGS. 19A and 19B are images of dissected lung tissue from animal studies and show examples of necrosis development in lung tissue as a result of hypertonic saline infusion and RF energy application. FIG. 19A shows a case of 23.4% hypertonic saline infusion at a rate of 3 ml/min for 10 min. No RF energy was applied. Hypertonic saline was delivered into the lower left lung of an animal. The animal was survived for 1 month. Histopathology was performed subsequently. The gross pathology view shown in FIG. 19A reveals a necrotic spot 805 of about 0.5 mm in size. The necrotic spot 805 was likely somewhat larger acutely, after infusion, but it was then gradually reabsorbed by the animal's body over the course of one month. There were no concerning safety issues noted in this animal Blood electrolytes, such a Na level, were unchanged with respect to pre-procedure baseline. Blood pressure and other vitals were all normal. No bacterial colonies were observed at high-magnification histopathology. Yet, the presence of the small necrotic spot is indicative of the potential therapeutic effects of hypertonic saline. When combined with delivery of RF energy, the therapeutic effect of hypertonic saline increases. For example, as shown in FIG. 19B, the combined effect of RF energy and hypertonic saline resulted in a necrotic zone 806 of about 5 mm, about ten times the size of that in FIG. 19A. The same amount of 23.4% hypertonic saline was delivered to the lower right lung in the case of FIG. 19B as in that of FIG. 19A. The same flow rate of 3 ml/min for 10 min was used. In addition, 10 W of RF power were applied for 90 seconds during the period of saline delivery. The same animal was treated as in the case of FIG. 19A. Hence, the combined effect of RF energy and infusion of hypertonic saline can result in an increased zone of necrosis and thus an increased therapeutic outcome when ablating tissue in the lung such as tumors.

The composition of the conductive fluid, e.g., HTS, may be adjustable such that electrical or thermal conductivity or viscosity of the HTS may be adjusted. For example, a conductive fluid source may comprise multiple sources that may be combined to adjust properties of the conductive fluid that is injected into the target region of the lung. A software driven controller may be programmed to mix a predetermined or automatically determined ratio of the multiple sources before or during injection of the combined fluids into a natural airway of the lung at the target region to be ablated. For example, separate pumps may be activated at a controlled rate and duration to selectively take a desired amount of each of the multiple sources. The multiple fluids may be pumped to a mixing chamber prior to delivering the combined fluid through the device to the target region, or they may be concurrently or sequentially delivered directly to the target region. Automatic determination of a ratio of multiple sources may be calculated by the controller using input from sensors, for example located on the distal region of the device.

Alternatively, multiple sources of fluids having different properties, such as saline with different salinity, may be provided and a controller may select which source to draw from for irrigation without mixing the solutions. The controller may select a source of fluid based on time within an ablation procedure or total cumulative volume of a fluid delivered to a patient or feedback from sensors such as impedance or temperature. In one example, a first source may contain hypertonic saline (e.g., saline with a salinity above 10%, above 15%, above 20%, about 23.4%) and a second source may contain saline with a lower salinity (e.g., 0.9%). The first source may be drawn from to irrigate the target lung space during an initial period of an ablation procedure and the second source may be drawn from to irrigate during a second period of the ablation procedure. The rationale is that hypertonic saline may be irrigated to get the ablation started and to prime the environment in the target lung space for electrical conductivity, however due to its high salinity it may cause edema in the lung. Too much edema is undesirable. After a first period of irrigated ablation (e.g., up to 2 minutes, up to 2.5 minutes, up to 25% of a total ablation duration) the tissue environment should be prepared enough that a lower salinity saline could be able to do the job of temperature regulation without having the drawback of causing a lot of edema. Optionally, the controller may detect if the conductivity is reduced by the lower salinity saline to a predefined level, for example via impedance measurement, and switch back to the higher salinity saline.

Optionally, the controller may adjust ablation energy delivery parameters (e.g., flow rate of conductive fluid, ablation energy power, set temperature, ramp rate, duration) based on varying properties of the conductive fluid such as conductivity, viscosity, temperature, or pressure. For example, adjusting at least one of the flow rate or the conductivity of the conductive fluid may include adjusting at least one of the flow rate or the conductivity to maintain the values detected by a temperature sensor within a determined temperature range, optionally wherein the determined temperature range is between 60 and 115° C., or above a certain temperature threshold, optionally wherein the preferred temperature threshold is 75-105° C., for example between 85-99° C. In another example, a system is configured to adjust the conductivity of the conductive fluid in the range between 10 mS/cm and 450 mS/cm at a reference fluid temperature of 25° C.

For example, as shown in Table 1, a 6 min delivery of RF power, at an average of 67 W, resulted in an average tissue temperature of 90° C. and an ablation volume of 4.4 cm×3.1 cm×3.9 cm, approximately 27 cm$^3$. Furthermore, hypertonic saline, or any other aqueous solutions from those discussed above (e.g. calcium chloride, magnesium chloride, sodium hydroxide, etc.), is known to be toxic to cancer cells and can alternatively or additionally chemically ablate tumor cells. The permeated saline in lung parenchyma may replace the alveolar air and spread to the surrounding alveoli through Kohn's pores and Lambert's ducts. Perfused hypertonic saline could be doped with nonionic iodinated contrast agent to render it visible on computed tomography (CT). Other conductive irrigation fluids could be imagined such as aluminum sulfate. Creating a flow of the conductive fluid with the use of suction during ablation to continuously replenish irrigation sitting in the ablation zone could further facilitate tumor ablation by removing heat generated in the fluid.

Different liquids can be mixed under computer control to create controllable, programmable and predictable concentration of conductive ions. Alternatively, a non-flowing conductive fluid pooled in the targeted lung tissue could facilitate production of a lesion sufficient to ablate a targeted lung tumor. A desired ablation volume, which may be for example a function of tumor size, distance between the targeted tumor and RF electrodes, or proximity to vulnerable non-target structures, may determine if infusion of a conductive fluid is flowing or stagnant, wherein stagnant infusion may be used for smaller ablations and flowing infusion may be used for larger ablations and optionally a greater flow rate or cooling of injected liquid may be used for even larger ablations.

Conductive fluid can be infused before the start of ablation to prepare the lung for ablation and allow for the fluid to flow into the tissue. Delivering conductive fluid such as hypertonic saline may allow the ablation energy console to operate at a wider range of power levels as necessary to achieve therapeutic goals.

Figure 13:
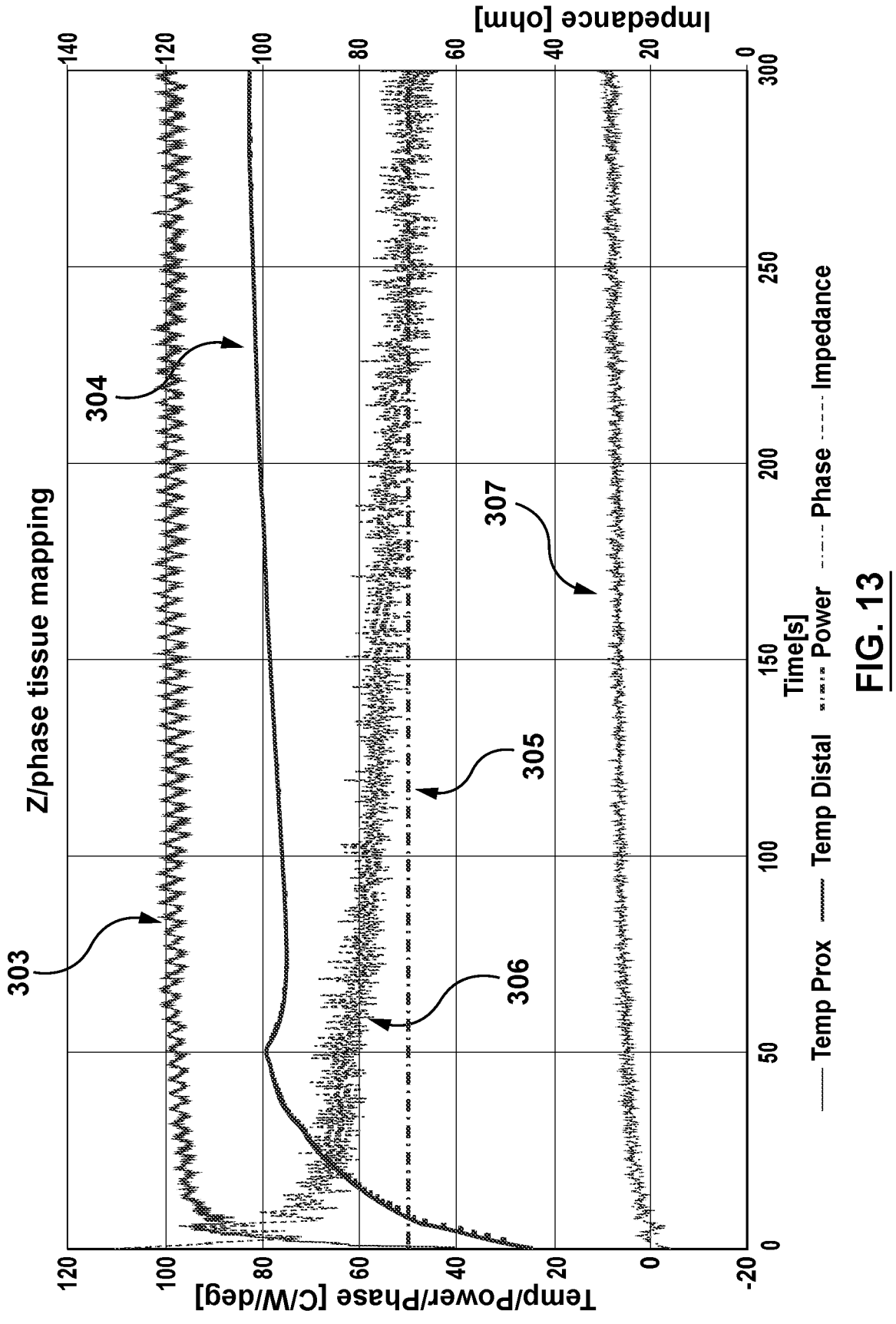
FIG. 13 is a graph of electrode temperatures, power, phase and impedance during RF delivery with hypertonic saline irrigation.

FIG. 13 illustrates an example of proximal electrode temperature 303, irrigated distal electrode temperature 304, power 305, impedance 306 and phase 307 ranges achieved by infusing hypertonic saline at a rate of 1 ml/min. The temperature may be regulated within a range above 60° C. but below 115° C. (e.g., below 105° C., below 100° C.), although it may fluctuate outside such range for limited periods of time (e.g., less than 1 second, less than 2 seconds, less than 3 seconds).

Optionally, a conductive fluid may be injected through a needle catheter positioned in an airway into the parenchyma or tumor, which may deliver the conductive fluid to the target site more effectively or more selectively. The needle may further comprise an RF electrode with an associated temperature and impedance sensor that may be used to deliver RF energy directly to the parenchyma near the tumor or inside the tumor.

Optionally, the conductive fluid such as hypertonic saline solution infusion may be titrated to adjust the size of ablation. As discussed above, hypertonic saline flow rates between 0.2 to 5 ml/min are expected to contribute to the formation of sufficiently large ablation volume, while keeping the patient's electrolytes, blood pressure and fluid loading within normal and safe ranges. Titration may be done by adjusting the saline concentration, the volume of hypertonic saline infused, or by adjusting the position of the occluding structure to block off a different size of lung portion. A higher saline concentration is more electrically conductive and may generate a larger lesion. A greater volume of infused saline may spread to a greater volume of tissue creating a larger lesion. A larger portion of lung that is occluded may accept a larger amount of infused hypertonic saline, which may result in a larger lesion. RF delivery parameters may be adjusted in accordance with hypertonic saline titration. For example, salinity of irrigation fluid may be increased in response to undesired fluctuations in impedance values.

Embodiment #1 (Ablation Electrode(s) on a Single Shaft for Placement in an Airway)

Figure 3:
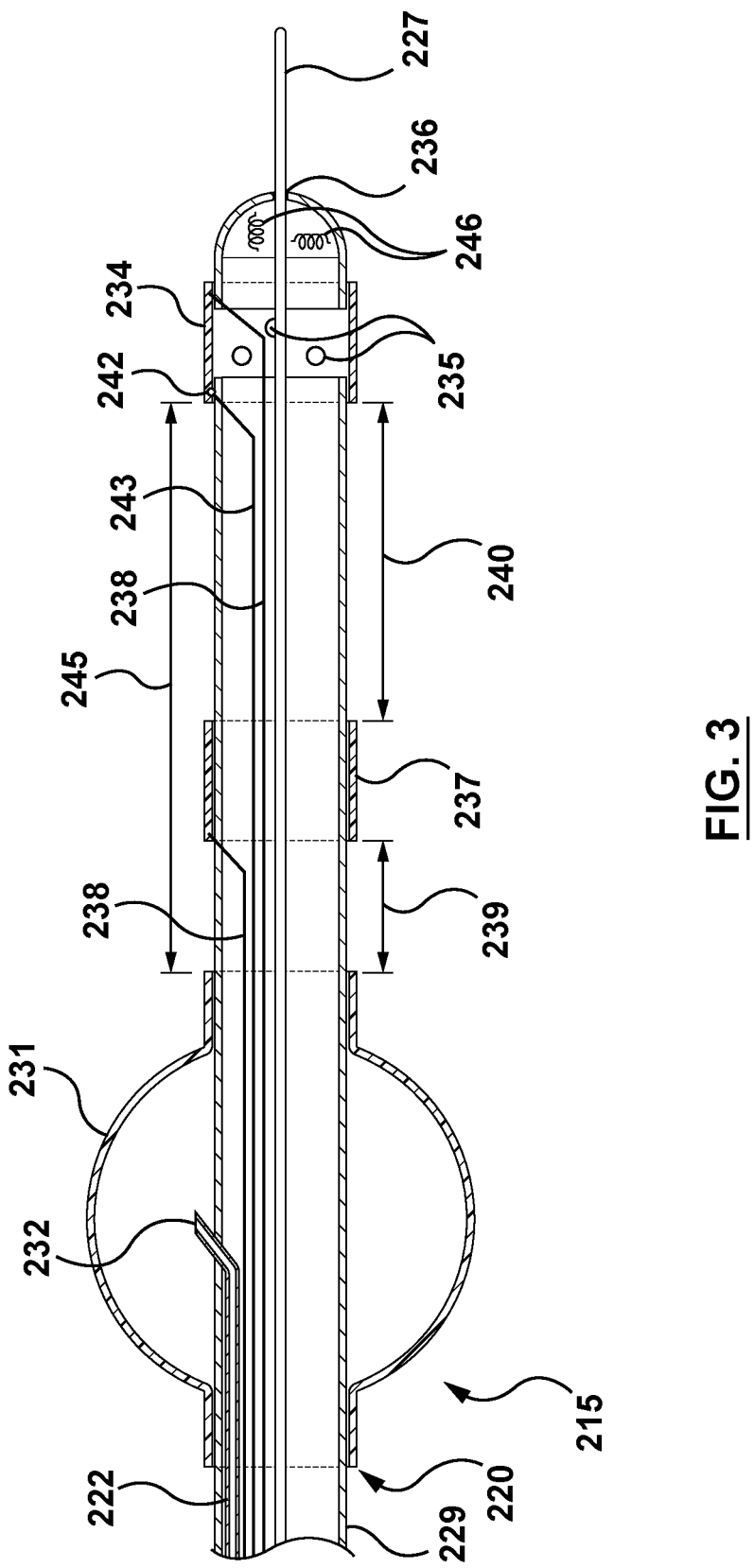
FIG. 3 is a schematic illustration of a distal region of an ablation device, constructed with one occluding balloon proximal to the electrodes.

An example of a device 220 configured to be delivered through a working channel, occlude a targeted portion of lung, reduce air volume in the targeted portion of lung, deliver conductive solution into the targeted portion of lung, monitor tissue properties, and ablate a tumor is shown in FIG. 3. The device of FIG. 3 is shown in situ in FIG. 4A.

The device 220 has an elongated shaft 229 having a proximal region intended to remain outside the patient's body and a distal region 215 intended to be delivered through a working channel to a target region of a lung proximal to a targeted lung tumor. The distal region 215 is configured to be delivered through a working channel (e.g., working channel 225 of a bronchoscope 221 or a lumen of a sheath 213 that may be delivered through the working channel of a bronchoscope). For example, a common bronchoscope working channel may have an inner diameter of 2.8 mm and a length of 60 cm. A delivery sheath 213 adapted for delivery through a 2.8 mm bronchoscope working channel may have an outer diameter less than 2.8 mm, preferably about 1.95 mm+/−0.05 mm, an inner diameter approximately 0.45 mm less than the outer diameter, preferably about 1.5 mm+/−0.05 mm, and a length greater than the brochoscope's length (e.g., greater than 60 cm, preferably about 105 cm). Other dimensions may be applicable for similar catheters adapted to fit through different sized bronchoscope working channels. In its delivery state a device 220 may have a maximum diameter smaller than the inner diameter of the sheath 213 through which it is delivered, for example less than or equal to 2 mm (e.g., less than or equal to 1.5 mm, preferably 1.4 mm+/−0.05 mm). The device 220 may have a length greater than the length of the delivery sheath, for example greater than or equal to 50 cm (e.g., greater than or equal to 60 cm, greater than or equal to 105 cm, preferably about 127 cm). The Shaft 229 of the device 220 may be made for example from an elongate tube of Pebax 720 having an outer diameter of about 1.35 mm. The shaft may be a flexible shaft capable of traversing a bend such that a bend in the shaft has a radius of curvature of as little as 7 mm. The shaft may contain a wire braid to provide flexible, pushable, kink resistant, and torquable functions.

Optionally, the device 220 may have a guidewire lumen 236 (e.g., a polyimide tube with an inner diameter of 0.015" running through a lumen in the shaft 229) so the device may be delivered over a guidewire 227 or so a component such as a stiffening wire or tumor perforating wire or fiberoptic wire or other device can be delivered through the lumen.

Figure 4B:
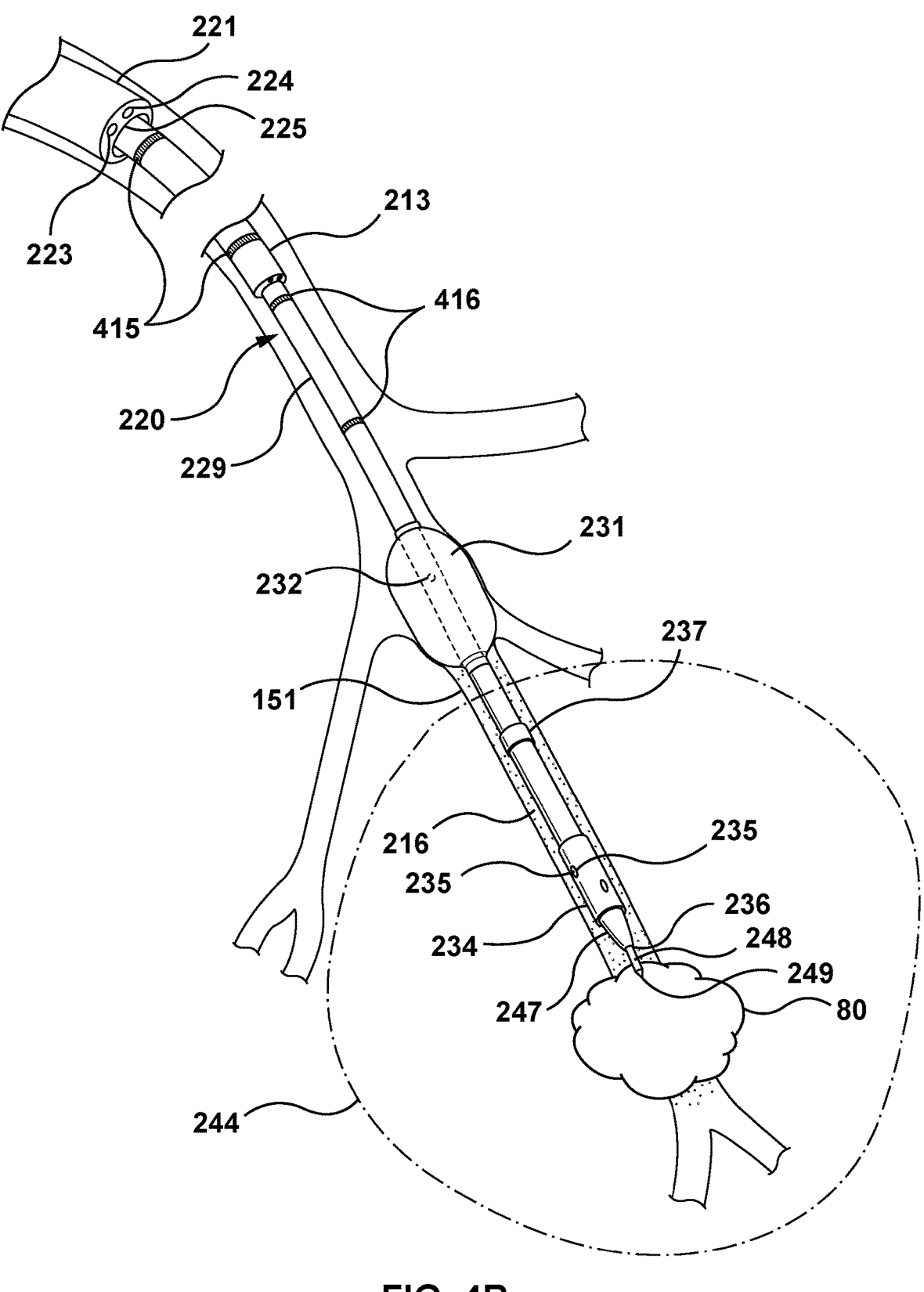
FIG. 4B is a schematic illustration of an alternative embodiment having a tumor perforating wire and hole dilator.

Alternatively, as shown in FIG. 4B, a tumor-perforating-wire 248 having a sharp distal tip 249 may be advanced through a guidewire lumen 236 to protrude from the distal end of the catheter 220 to facilitate puncture through tissue such as a tumor 80 that is blocking or encroaching into an airway. The device 220 shown in FIG. 4B is the same as the device of FIG. 4A except that it has a tapered distal end 247 with a lumen 236 exiting the point of the tapered distal end 247. The tapered distal end 247 may be used as a dilator that can enter a hole in tissue created by the tumor-perforating-wire 248 and expand the hole so the ablation electrode 234 can be advanced into or through the hole. Optionally, the tumor-perforating-wire 248 may have a depth marker on its proximal region to indicate when the sharp distal tip 249 is near the distal end of the catheter 247. Optionally, the tumor-perforating-wire 248 is made from a material that is radiopaque or has a radiopaque marker near its sharp distal tip 249. In a method of use the catheter 220 may be advanced through a patient's airways without a tumor-perforating-wire 248, which allows the catheter 220 to be more flexible facilitating passage over tight bends. Optionally, a guidewire may be used to facilitate delivery of the catheter. If the targeted tumor is at least partly in the airway blocking the catheter from further advancement the tumor-perforating-wire 248 may be advanced through the lumen 236 until the sharp distal tip 247 is near the opening, optionally as indicated by the depth marker. The sharp distal tip 247 is then advanced into or through the tumor, optionally under fluoroscopic guidance or other medical imaging or robotic guidance to monitor advancement and avoid a risk of puncturing the pleura or other non-target tissue. Optionally, the tumor-perforating-wire 248 may be configured to only advance a predetermined distance (e.g., up to about 3 cm, up to about 2 cm, up to about 1 cm, up to about 5 mm) from the distal end of the catheter 220. The catheter 220 may be advanced such that the tapered tip 247 dilates the hole in the tumor made by the tumor-perforating-wire 248 and the ablation electrode 234 enters the tumor 80. The tumor-perforating-wire 248 may be removed prior to delivering ablation energy.

Alternatively, a shaft-stiffening wire may be advanced through a lumen in the shaft, for example a guidewire lumen 236, to increase stiffness of the catheter during positioning. The catheter shaft may be quite flexible so it can pass over an airway bend with a radius of curvature as little as 7 mm but may require more stiffness at times when advancing to avoid kinking.

Optionally, the sheath 213 may have depth markers 415 positioned along its length or portion of its length (e.g., at least on the proximal 5 cm and distal 5 cm of the sheath length) and spaced at regular intervals (e.g., spaced at 1 cm center to center with a width of about 1 mm). Optionally, the shaft 229 of the embodiment shown in FIG. 4A or the shaft 429, 529 of other embodiments shown in FIG. 5A or 5B, may have depth markers 416 positioned along its length or portion of its length (e.g., at least on the proximal 5 cm and distal 5 cm of the shaft length) and spaced at regular intervals (e.g., spaced at 1 cm center to center with a width of about 1 mm). The depth markers may be added to the sheath or shaft using methods known in the art such as pad printing or laser etching. In use, a physician may position a working channel (e.g., bronchoscope working channel) in a patient's lung and use the depth markers on the sheath or shaft relative to the working channel to determine placement of the ablation electrode or obturator relative to the working channel.

The device 220 is configured to temporarily at least partially occlude an airway that feeds the targeted lung portion. As shown in FIGS. 3 and 4A the device 220 has an occlusion element such as an inflatable balloon or obturator 231. The elongated shaft 229 comprises a lumen 222 (e.g., a polyimide tube with an inner diameter of 0.015" running through a lumen in the shaft 229) with a port 232 positioned in the obturator 231 for inflating and deflating the obturator. The obturator 231 may be a balloon (e.g., compliant balloon) sized to occlude the airway or a range of airway diameters (e.g., diameters in a range of 3 mm to 10 mm). The obturator 231 may be inflated by injecting fluid (e.g., gas such as air, or liquid such as water or saline, or contrast solution) through the lumen 222 and into the obturator 231. Optionally, fluid may be injected manually with a syringe connected to a proximal region of the device 220 and fluid pressure may be contained by closing lock stop valve. The obturator may be deflated for removal by opening the lock stop valve and pulling the inflation fluid from the balloon using the syringe. Alternatively, a system for operating the device may comprise a pump to inject or remove fluid to inflate or deflate the balloon. Optionally, a second port in fluid communication with a second lumen may be positioned in the obturator to allow inflation fluid to be removed from the obturator as it is being injected so as to maintain inflation pressure but allow fluid to be circulated in the obturator, which may help to keep the temperature of the obturator cooler than ablation temperature and avoid a risk of thermally damaging the obturator.

Figure 4C:
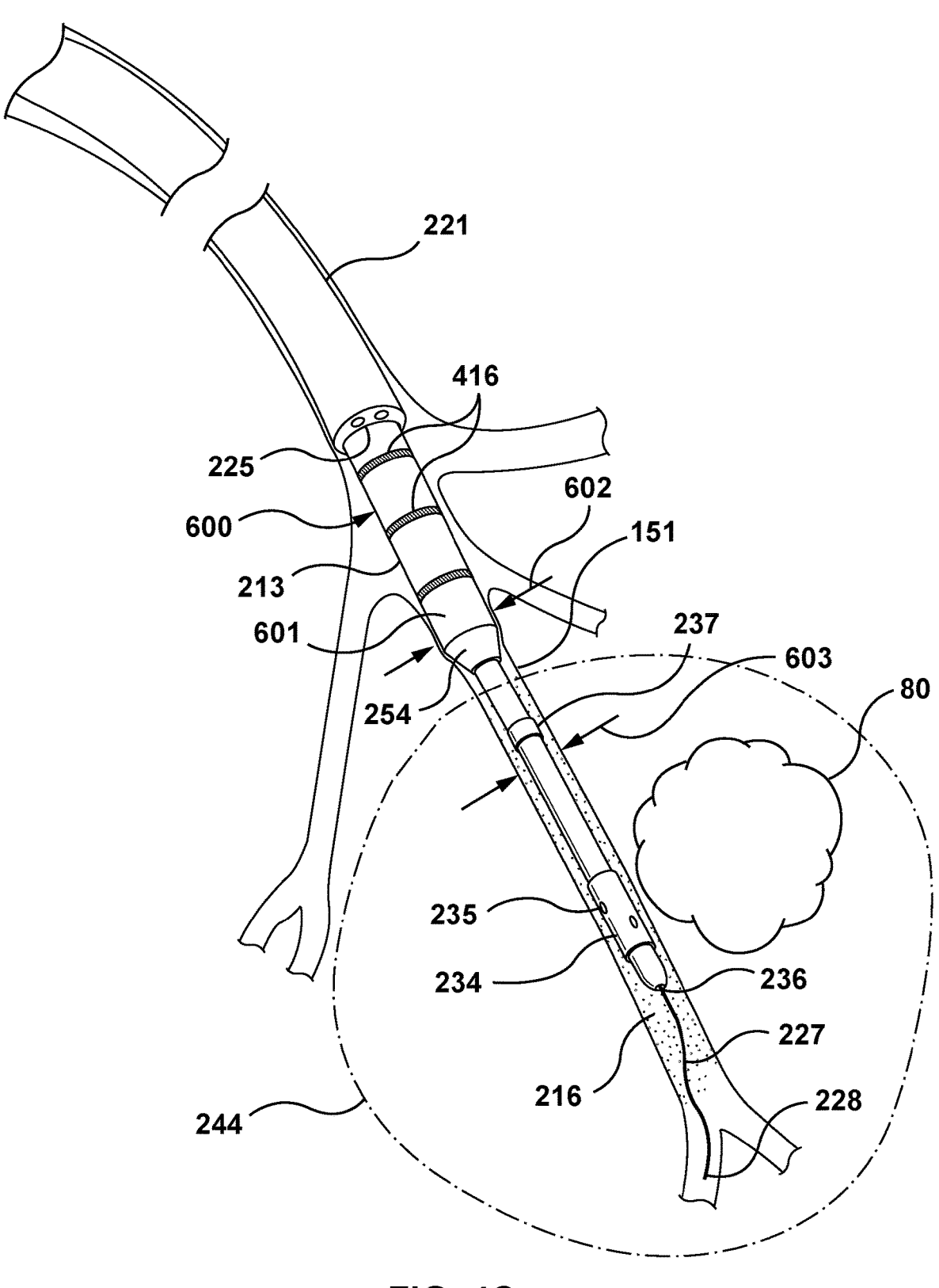
FIG. 4C is a schematic illustration of an alternative embodiment having a tapered shaft section.
Figure 5A:
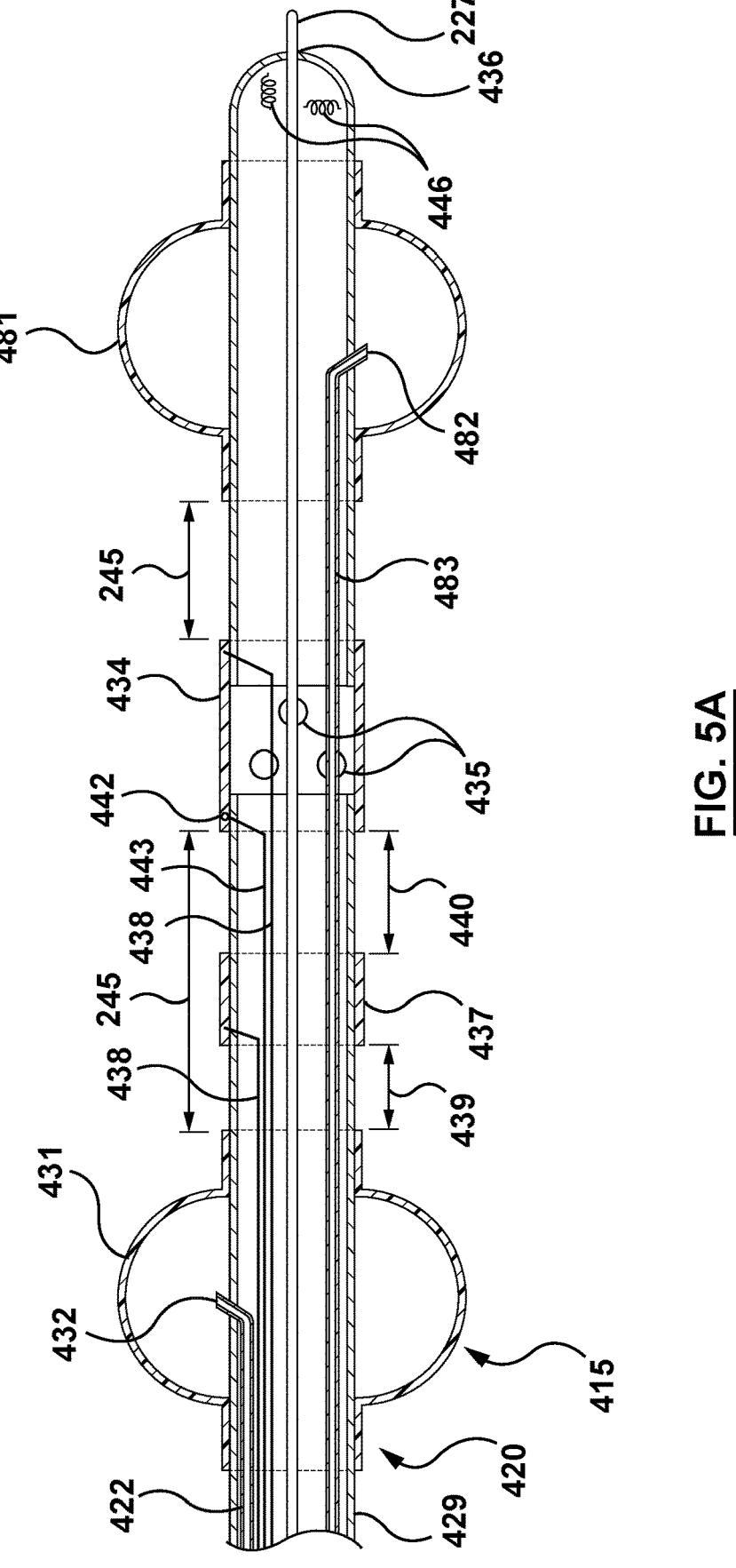
FIG. 5A is a schematic illustration of a distal region of an ablation device, constructed with two occluding balloons on the same shaft, one of which is proximal to the electrodes and the other is distal to the electrodes.
Figure 5B:
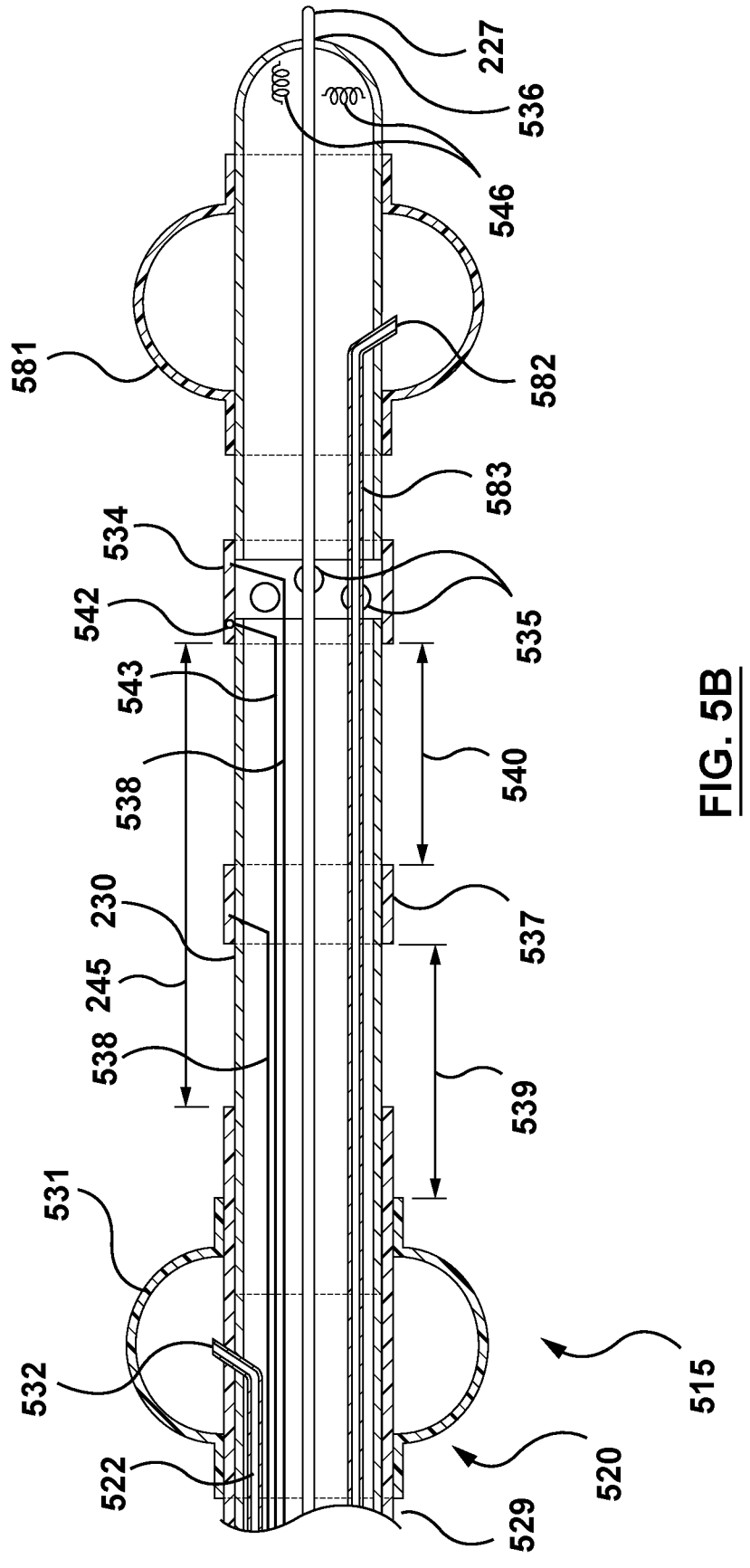
FIG. 5B is a schematic illustration of a distal region of an ablation device, constructed with two occluding balloons, one of which is proximal to the electrodes and located on a first shaft, and the other is distal to the electrodes and located on a second shaft which is extended from the first shaft.
Figure 7:
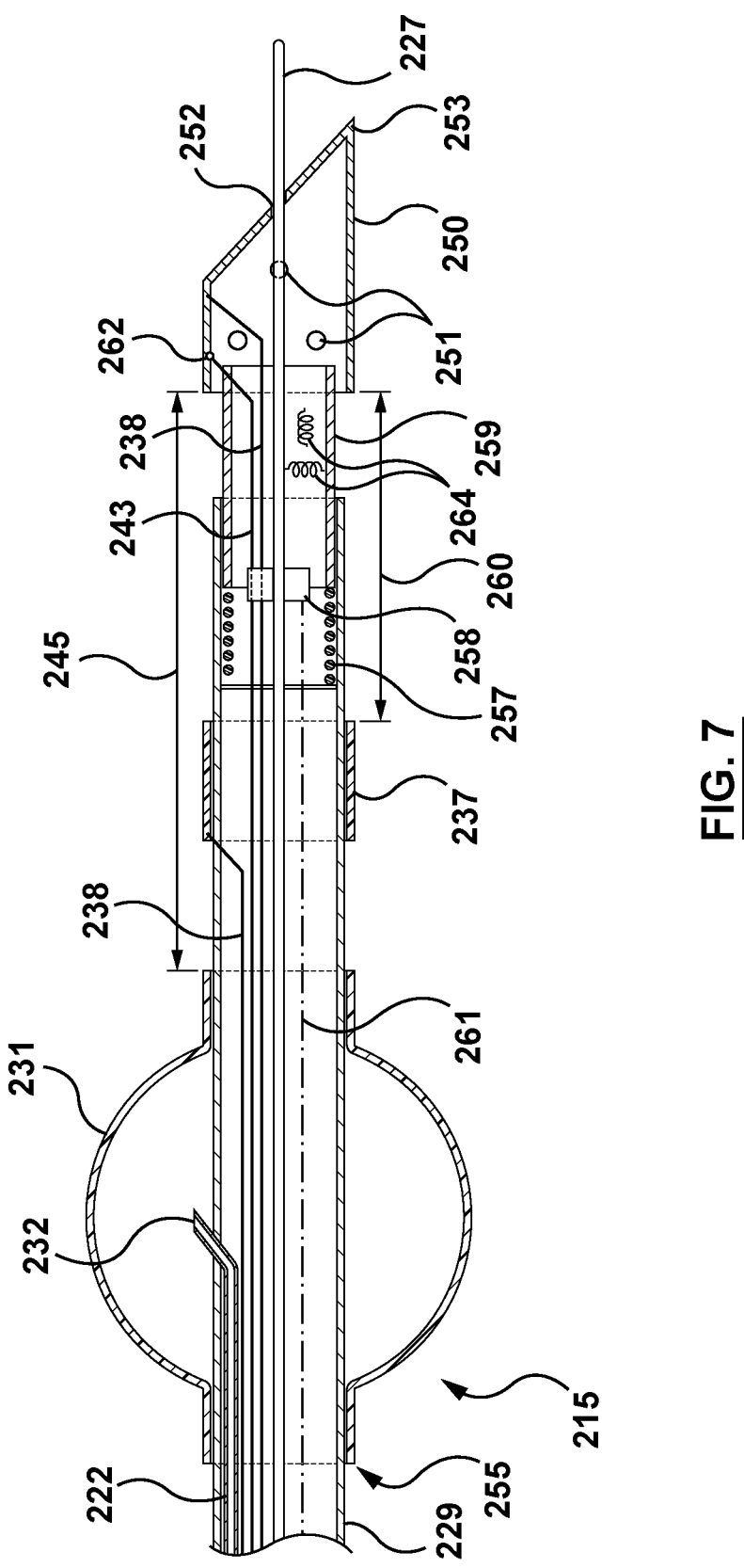
FIG. 7 is a schematic illustration of a distal region of an ablation device having a needle electrode.

The obturator 231 shown in FIGS. 3 and 4 or similar obturators 431, 481 shown in FIG. 5A, 531, 581 shown in FIG. 5B, 231 shown in FIG. 7 may be compliant, semi-compliant, or non-compliant inflatable balloons, preferably compliant balloons made from a material capable of avoiding damage at temperatures up to at least 120° C. for at least 30 minutes and withstand inflation with 1 cc of air for at least 30 minutes. A suitable example of a compliant balloon material is silicone, which may safely endure temperature in an operational range of body temperature up to about 140° C. For example, balloon material may be 40 A silicone with a wall thickness of 0.0015"+/−0.001" formed at 0.1" diameter for reliable low-pressure inflation to 12 mm in width. Balloon obturators may be attached to the shaft 229 in a stretched configuration (e.g., stretched 2 times the relaxed length) and bonded at both ends with adhesive such as cyanoacrylate. Optional heat shrink collars (e.g., PET) may be added over the bonded ends of the balloon for added strength. Inflatable balloon obturators of any embodiments disclosed herein may be somewhat spherical like the balloon 402 shown in FIG. 14A, for example having a length 400 in a range of 5 mm to 30 mm (e.g., 12 mm) and a diameter 401 of similar dimension in a range of 1 mm to 30 mm (e.g., 12 mm) in an inflated ex-vivo state. Alternatively, inflatable balloons may be elongated or sausage-shaped like the balloon 403 shown in FIG. 14B for example, having a length 404 in a range of 5 mm to 30 mm (e.g., in a range of 10 to 20 mm) and a diameter 405 of smaller dimension in a range of 1 mm to 30 mm (e.g., in a range of 4 mm to 20 mm, about 12 mm) in an inflated ex-vivo state. The elongated balloon 403 may provide a better fluid seal of the airway and may maintain position better during use compared to a spherical-shaped balloon 402. However, as balloon length increases so does friction between the balloon and sheath increase making it more difficult to deliver through the sheath or increasing a risk of damaging the balloon during delivery. Therefore, it may be preferred that the balloon is no longer than 30 mm (e.g., no longer than 25 mm, no longer than 20 mm).

Figure 14C:
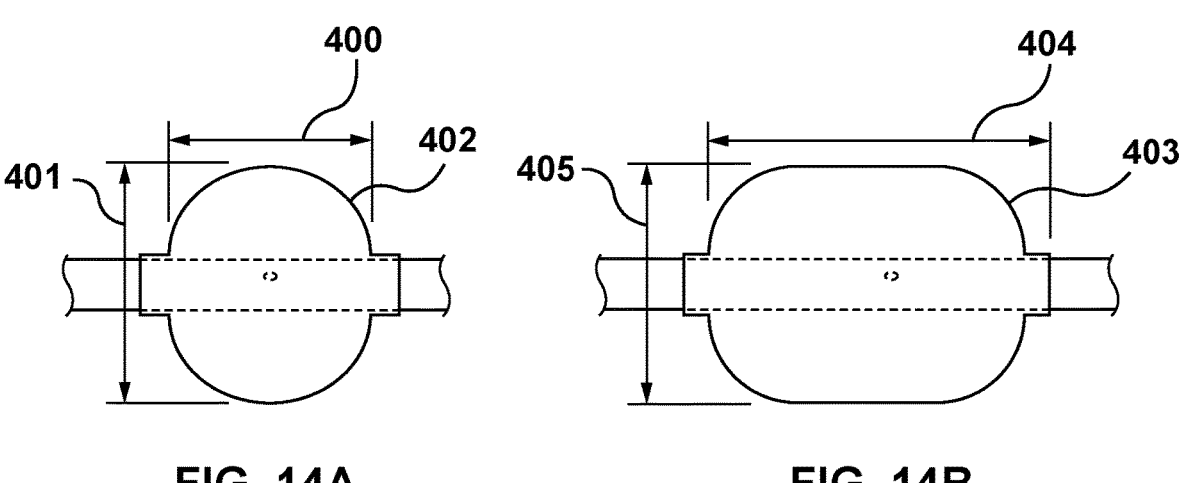
Figure 14C:
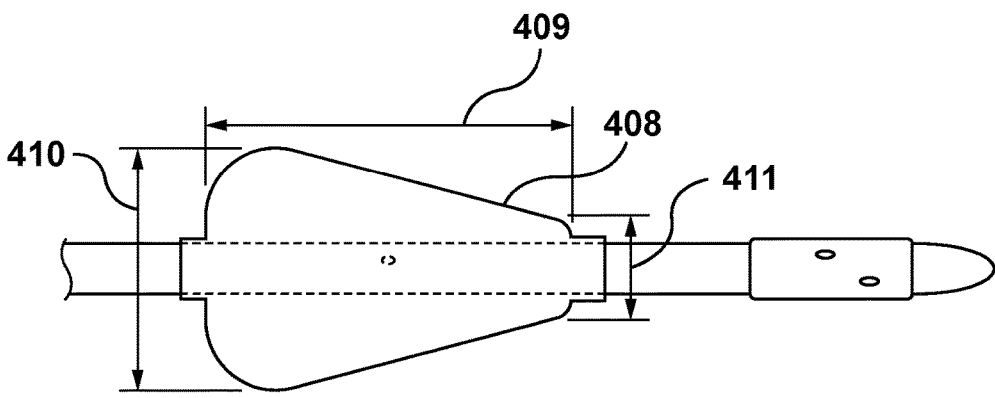

Alternatively, inflatable balloon obturators of any embodiments disclosed herein may be somewhat tapered like the balloon 408 shown in FIG. 14C, for example having a length 409 in a range of 5 mm to 30 mm and a first diameter 410 in a range of 1 mm to 30 mm (e.g., 12 mm) tapering down to a second diameter 411 in a range of 0 mm to 20 mm (e.g., about 2 mm) in an inflated ex-vivo state wherein the first diameter (i.e., the larger end of the tapered balloon 408) is further away from the ablation electrode than the second diameter. This tapered balloon shape may improve the ability of the airway and lung tissue to collapse toward the ablation electrode when vacuum is applied to the airway in use, while allowing a functional seal of the airway.

Figure 14D:
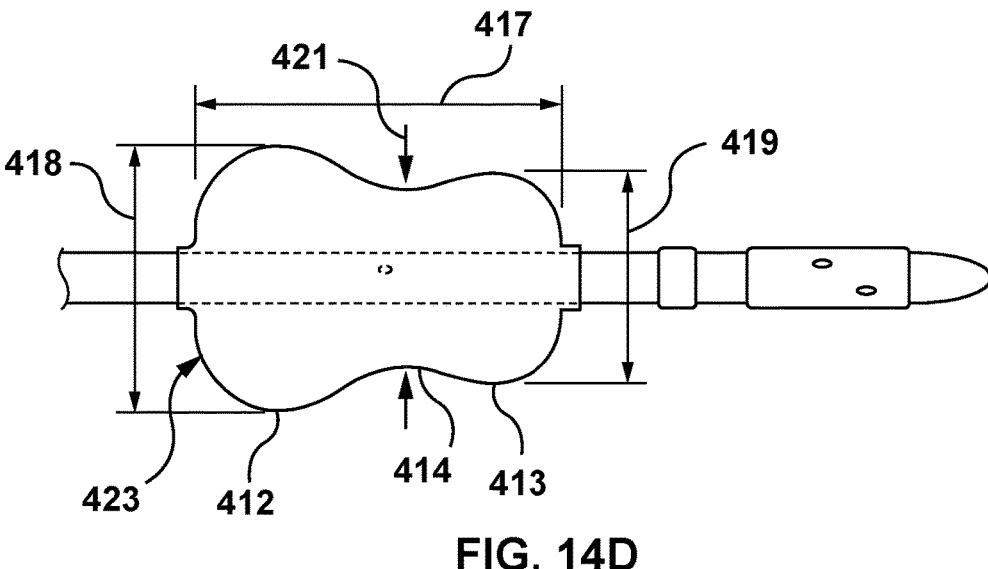

Another alternative embodiment of an occlusion balloon 423 as shown in FIG. 14D may have an elongated shape with a proximal section 412, a distal section 413 and a waist 414 therebetween. For example, in an inflated ex-vivo state, the proximal section 412 of the balloon 423 may have a width 418 in a range of 1 mm to 30 mm (e.g., about 12 mm); the distal section 413 may have a width 419 in a range of 1 mm to 20 mm (e.g., about 10 mm); and the waist 414 may have a width 421 that is less than the widths 418 and 419, for example in a range of 1 mm to 19 mm (e.g., about 8 mm). Optionally, the distal section width 419 may be smaller than the proximal section width 418. One way to create this shape of balloon is to make the balloon material slightly thicker in the waist region 414. This balloon configuration may occlude an airway and be especially beneficial if positioned near an opening of a target bronchus wherein the distal section 413 may be placed in the target bronchus while the proximal section 412 is placed to seal the opening of the target bronchus.

Alternatively, the occlusion balloon 231 may be a different form of occlusion structure such as a deployable valve, or a deployable stent with an occluding material such as PTFE.

FIG. 4A illustrates the ablation apparatus 220 shown in FIG. 3 introduced into a selected airway 151 comprising an elongated shaft 229, a space occluder (e.g., an obturator) 231 positioned on a distal region of the shaft to occlude the airway, at least one air removal port 235 in fluid communication with a lumen (not shown) that is connectable at the proximal region of the catheter to a suction device (e.g., vacuum pump) to remove air from the airway 151 distal to the obturator 231 to collapse the targeted portion, segment or lobe of the lung. In an example embodiment a device 220 has four air removal ports 235 each having a diameter of 0.017". Air may be removed from the targeted lung portion by applying negative pressure (e.g., with the suction device) to the lumen that is in communication with the air removal port 235, that pulls air from the lung portion through the lumen to a proximal region of the apparatus external to the patient. As shown the air removal port 235 is the same port through which a conductive fluid (e.g., hypertonic saline) may be delivered. Alternatively, air may be removed from the targeted portion of lung by applying suction to a different lumen such as guidewire lumen 236 or an additional lumen (not shown) having an exit port on the shaft 229 distal to the obturator 231. Alternative methods of at least partially collapsing a targeted portion of lung are described herein.

Figure 12:
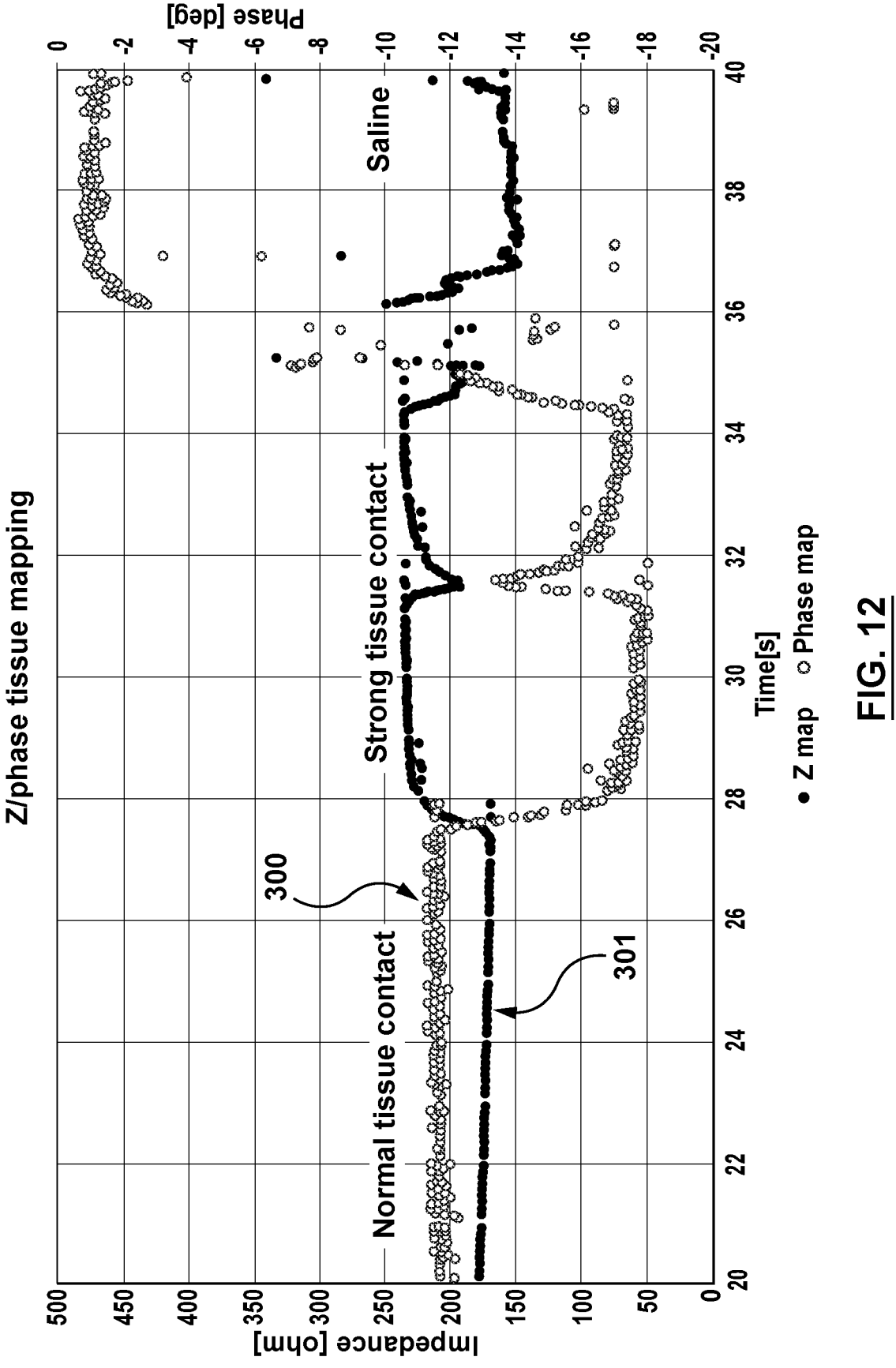
FIG. 12 is a graph of impedance and phase during periods before lung portion collapse, following lung portion collapse, and following injection of hypertonic saline during an experiment.

The device 220 shown in FIGS. 3 and 4A further comprises a distal electrode 234 positioned on the distal region 215 of the device 220 and connected to a conductor 238 (e.g., copper wire 32 AWG) that runs through the shaft 229 of the device to the proximal region where it is connectable to an energy delivery console for delivery of RF ablation energy. A sufficient electrical insulation should be provided to insulate and avoid dielectric stress between conductors and electrodes. During ablation energy delivery RF voltages of 300V at a frequency in a range of 300 kHz to 1 MHz may be applied. A minimum dielectric strength may be about 2000 V/mm. For example, electrical insulation may be provided by insulation on the conductors and the shaft material. Additionally, a dielectric material such as a UV cured adhesive may be injected into a lumen in the shaft 229 that carries conductors at least in the distal region of the device proximate the distal electrode 234 to increase dielectric strength between the distal electrode 234 and proximal electrode 237. The distal electrode 234 may be cylindrical in shape and have a diameter in a range of 0.5 mm to 2 mm (e.g., about 1.35 mm) and a length in a range of 3 mm to 20 mm (e.g., in a range of 3 mm to 10 mm, about 5 mm). An optional proximal electrode 237 is positioned on the shaft 229 distal to the obturator 231 (e.g., a distance 239 in a range of 1 mm to 8 mm, about 5 mm) and proximal to the distal electrode 234 (e.g., a distance 240 in a range of 5 to 15 mm, about 10 mm). The optional proximal electrode 237 may have a length in a range of 0.5 mm to 5 mm, preferably 1 mm+/−0.25 mm and an outer diameter in a range of 0.5 mm to 2 mm (e.g., about 1.35 mm). The total distance 245 between the distal electrode 234 and the obturator 231 may be in a range of 1 mm to 40 mm (e.g., in a range of 5 mm to 30 mm, in a range of 10 mm to 20 mm, about 16 mm+/−2 mm), which may allow the distal electrode 234 to heat adjacent tissue and conductive fluid without risking thermal damage to the obturator 231 or which may avoid a risk of the obturator negatively influencing the ability to create a sizable ablation zone 244 around the ablation electrode 234. The proximal electrode 237 is connected to a conductor 241 (e.g., 32 AWG copper conductor) running through the shaft 229 to the proximal region of the catheter where it is connectable to an energy delivery console. Optionally, the distal 234 and proximal 237 electrodes may be used together to complete an electrical circuit used to measure or monitor electrical impedance or phase of the tissue proximate to the two electrodes. The impedance or phase may be used to assess the state of bronchial air volume reduction during a step of air volume reduction in the lung portion or during ablation energy delivery, or to assess degree of infusion of conductive fluid into the targeted lung portion, or to assess degree of ablation of tissue proximate the electrodes. For example, in bench tests performed by the bipolar impedance measured between a distal electrode 234 and a proximal electrode 237 drops about 5 to 20% (e.g. from about 400Ω to about 350Ω). Correspondingly, the phase would increase from approximately a pre-collapse range of −20° to −60° down to a post-collapse range of −10° to −30°. FIG. 12 shows representative values of impedance 300 and phase 301 at 480 kHz under various tissue contact scenarios including "normal tissue contact", "strong tissue contact" following collapse of the targeted lung portion, and "saline" after hypertonic saline was injected into the targeted airway. Additionally, when filling up the space in a collapsed airway with hypertonic saline the electrical impedance shows a steady and consistent decrease during a first portion of an RF application. The consistent and stable behavior of electrical impedance may be used to indicate to a user that the targeted airway has collapsed providing greater tissue contact.

As shown in FIGS. 3 and 4A the ablation catheter has an ablation electrode 234 and distal to the ablation electrode is a short section of shaft with a guidewire port 236. Alternatively, an ablation catheter may be absent a guidewire lumen. Furthermore, an ablation catheter may be absent the short section of shaft distal to the ablation electrode 234 and the catheter may terminate in the ablation electrode, which may have a hemispherical distal tip.

Hypertonic saline (HTS) refers to any saline solution with a concentration of sodium chloride (NaCl) higher than physiologic (0.9%). Commonly used preparations include 2%, 3%, 5%, 7%, and 23% NaCl and are generally available in sterile bags or bottles through the hospital pharmacy. It is used in medical practice for its osmotic, rather than conductive qualities (e.g. to reduce edema). As discussed, other aqueous solutions can be used (e.g. calcium chloride, magnesium chloride, sodium hydroxide, etc.).

Conductive fluid (e.g., 3% to 30% hypertonic saline) may be delivered to the targeted lung portion through irrigation ports 235 in the electrode(s) 234 or additionally or alternatively through an infusion lumen (not shown) exiting the device 220 distal to the occlusion balloon 231 that may or may not exit through ports in an electrode. The infusion lumen runs from the irrigation ports (e.g., 235) through the shaft 229 to the proximal region of the device where it is connectable to a conductive fluid supply and optionally pump. Alternatively, the guidewire lumen 236 may be used to infuse the conductive fluid.

Alternatively, or additionally in combination with collapsing a targeted portion of lung, the previously aerated space may be infused with an electrically conductive fluid such as hypertonic. Use of hypertonic saline may enhance RF delivery based on the virtual electrode effect.

While the targeted lung portion is occluded with the obturator 231, optionally collapsed, and infused with conductive liquid, RF ablation energy may be delivered from an energy delivery console to the distal electrode 234. A temperature sensor 242 (e.g., T-Type thermocouple) may be positioned on or in the distal electrode 234 and be connected to thermocouple wire 243 running through the shaft 229 to the proximal region of the device 220 where it is connectable to an energy delivery console. The temperature sensor 242 may be used to monitor electrode 234 temperature during energy delivery in which it is used as a parameter to control energy delivery (e.g., temperature controlled power delivery to meet a set point temperature in a range of 45° C. to 115° C., preferably between 50° C. and 95° C., or constant power controlled power delivery with a maximum temperature in a range of 45° C. to 115° C., preferably between 50 to 95° C., depending on specific local conditions to avoid over heating).

As shown in FIG. 4A the extent of an ablation 244 is highly influenced by the infusion of conductive fluid to the targeted lung portion A return electrode to complete the electrical circuit may be a dispersive electrode positioned on the patient's skin wherein the RF energy conducts through tissue between the distal electrode 234 and the dispersive electrode. Optionally or alternatively, the proximal electrode 237 may also be used to delivery ablation energy or to complete the electrical circuit (e.g., bipolar mode).

As shown in FIG. 4A a bronchoscope 221 having a lens 224 and light 223 is positioned in a patient's airway and a catheter 220 configured for airway occlusion and tumor ablation is delivered through the bronchoscope's working channel 225 to a targeted portion of lung 226 (e.g., a lung portion, lobe, or segment). A guidewire 227 may comprise a navigation sensor 228, or the distal end of the ablation catheter may comprise a navigation sensor 246 (see FIG. 3) (e.g., virtual bronchoscopy, electromagnetic, 3D electromagnetic, ultrasound) which may be positioned at a targeted position using a 3D navigation system and the catheter 220 may be advanced over the guidewire via guidewire lumen 236. Optionally, the catheter 220 may be telescopic wherein the distance from the obturator 231 and distal electrode is adjustable and may comprise a first elongated shaft 229 with an occlusion balloon 231 mounted to the distal region of the shaft 229 that is inflated by injecting fluid (e.g., air, sterile water, saline) through a lumen in the first shaft in fluid communication with a balloon inflation port 232 located inside the balloon. The first shaft 229 comprises a lumen 233 through which a second shaft 230 comprising at least one ablation electrode 234 may be telescopically advanced. Alternatively, an ablation electrode may be positioned on the first shaft distal to the occlusion balloon with a fixed or adjustable distance between the balloon and electrode(s) as shown in FIG. 3. A telescopic or adjustable distance between the balloon and electrode may advantageously allow placement of the electrode next to the tumor and placement of the occluding balloon at a desired position, which may depend on the geometry of the airway, the size of targeted lung portion, or the size of tumor. Optionally, the second shaft 230 may be deflectable or rotatable with respect to the first shaft 229. The ablation electrode(s) 234 may optionally comprise at least one irrigation port 235 for irrigating the electrode.

Alternatively or additionally, a fiberoptic lens may be positioned on the elongated shaft 229 distal to the occlusion structure, which may be used to visualize the airway distal to the occlusion structure. This may facilitate for example confirmation of airway shrinking, position of the electrode(s), or injury to the airway while the occlusion structure is deployed.

Optionally, if the electrode is irrigated by injecting fluid through ports 235 the fluid may be retracted by applying suction to the guidewire lumen 236 to create a flow of fluid.

An expandable occlusion element such as the occlusion balloon 231 shown in FIG. 4A may allow the catheter to be used in a range of airway sizes by expanding the occlusion element until it occludes the airway. Alternatively, if a target tumor is located is a narrow airway an expandable occlusion element may be left unexpanded if it can be wedged into the narrow airway enough to occlude it. In an alternative embodiment of an ablation catheter as shown in FIG. 4C, the catheter 600 may omit an expandable occlusion element and the shaft 601 can be used to wedge into the airway to occlude it. Optionally, the ablation catheter 600 may have a tapered shaft section 254 that is part of the distal region of the catheter and proximal to the electrodes 237 and 234. The tapered shaft section 254 may help to seal the airway as it is advanced into the airway having a luminal diameter 603 that is less than or equal to the shaft diameter 602.

Figure 6A:
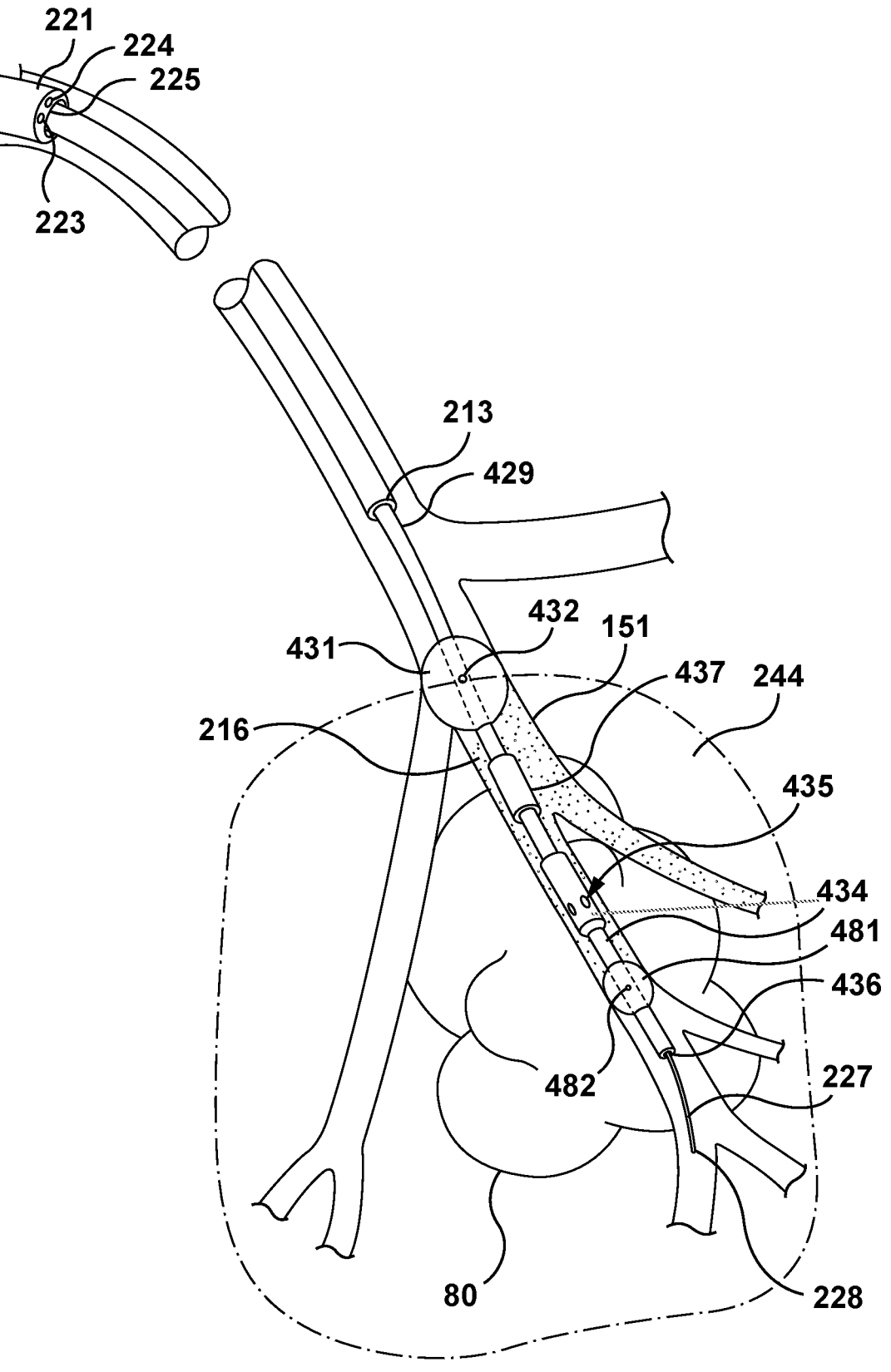
FIG. 6A is a schematic illustration of the device of FIG. 5A in situ.

Alternatively, as shown in FIGS. 5A and 6A, the device 420 can have two occlusion elements such as inflatable balloons or obturators 431, 481. One occlusion element is located proximal to the ablation electrodes, and the other is distal to the electrodes. The elongated shaft 429 comprises two lumens 422, 483 (e.g., a polyimide tube with an inner diameter of 0.015" running through a lumen in the shaft 429) with the corresponding ports 432, 482 positioned in the obturators 431, 481 for inflating and deflating the obturators. The obturator 431 or 481 may be a balloon (e.g., compliant balloon) sized to occlude the airway or a range of airway diameters (e.g., diameters in a range of 3 mm to 10 mm). The distance between the distal obturator and the proximal obturator is prefixed in this embodiment. For example, the distance between the balloons may be in a range of 20 mm to 40 mm. The obturators 431, 481 may be inflated by injecting fluid (e.g., gas such as air, or liquid such as water or saline, or contrast solution) through the lumens 422, 483 and into the corresponding obturators 431, 481. Optionally, fluid may be injected manually with a syringe connected to a proximal region of the device 420 and fluid pressure may be contained by closing lock stop valve. The obturators may be deflated for removal by opening the lock stop valve and pulling the inflation fluid from the balloon(s) using the syringe. Alternatively, a system for operating the device may comprise a pump to inject or remove fluid to inflate or deflate the balloons simultaneously or separately.

Alternatively, the occlusion balloon 431 or 481 may be a different form of occlusion structure such as a deployable valve, or a deployable stent with an occluding material such as PTFE.

FIG. 6A illustrates the ablation apparatus 420 shown in FIG. 5A introduced into a selected airway 151 comprising an elongated shaft 429, a proximal obturator 431 and a distal obturator 481 proximal and distal to the electrodes respectively (both of them are positioned on a distal region of the shaft to occlude the airway), an air removal port 435 in fluid communication with a lumen (not shown) that is connectable at the proximal region of the device to a suction device (e.g., vacuum pump) to remove air from the airway segment between the obturators 431, 481 to collapse the targeted portion, segment or lobe of the lung. Air may be removed from the targeted lung portion by applying negative pressure (e.g., with the suction device) to the lumen that is in communication with the air removal port 435, that pulls air from the lung portion through the lumen to a proximal region of the apparatus external to the patient. As shown the air removal port 435 is the same port through which a conductive fluid (e.g., hypertonic saline) may be delivered. Alternatively, air may be removed from the targeted portion of lung by applying suction to a different lumen such as guidewire lumen 436 or an additional lumen (not shown) having an exit port on the shaft 429 between the obturators 431, 481. Alternative methods of at least partially collapsing a targeted portion of lung are described herein.

Conductive fluid (e.g., 5 to 30% hypertonic saline) may be delivered to the targeted lung portion through irrigation ports 435 in the electrode 434 or additionally or alternatively through an infusion lumen (not shown) exiting the device 420 distal to the occlusion balloon 431 that may or may not exit through ports in an electrode. The infusion lumen runs from the irrigation ports (e.g., 435) through the shaft 429 to the proximal region of the device where it is connectable to a conductive fluid supply and optionally pump.

As shown in FIG. 6A a bronchoscope 221 having a lens 224 and light 223 is positioned in a patient's airway and a catheter 420 configured for airway occlusion and tumor ablation is delivered through the bronchoscope's working channel 225 to a targeted portion of lung 226 (e.g., a lung portion, lobe, or segment). A guidewire 227 may comprise a navigation sensor 228, or the distal end of the ablation catheter may comprise a navigation sensor 446 (in FIG. 5A) (e.g., virtual bronchoscopy, electromagnetic, 3D electromagnetic, ultrasound) which may be positioned at a targeted position using a 3D navigation system and the catheter 420 may be advanced over the guidewire via guidewire lumen 436.

Optionally, as shown in FIG. 5B, the catheter 520 may be telescopic wherein the distance from the proximal obturator 531 and distal electrode is adjustable (e.g., from a first distance in a range of 20 to 40 mm up to a second distance in a range of 30 mm to 70 mm) and may comprise a first elongated shaft 529 with a proximal occlusion balloon 531 mounted to the distal region of the shaft 529 that is inflated by injecting fluid (e.g., air, sterile water, saline) through a lumen 522 in the first shaft in fluid communication with the balloon inflation port 532 located inside the proximal balloon. The first shaft 529 comprises a lumen 533 through which a second shaft 230 comprising at least one ablation electrode 534 and the distal balloon 581 may together be telescopically advanced.

The second shaft 230 comprises a lumen 583 (e.g., a polyimide tube with an inner diameter of 0.015" running through a lumen in the second shaft 230) with the corresponding ports 582 positioned in the obturators 581 for inflating and deflating the obturators. The obturator 581 may be a balloon (e.g., compliant balloon) sized to occlude the airway or a range of airway diameters (e.g., diameters in a range of 3 mm to 10 mm).

Figure 6B:
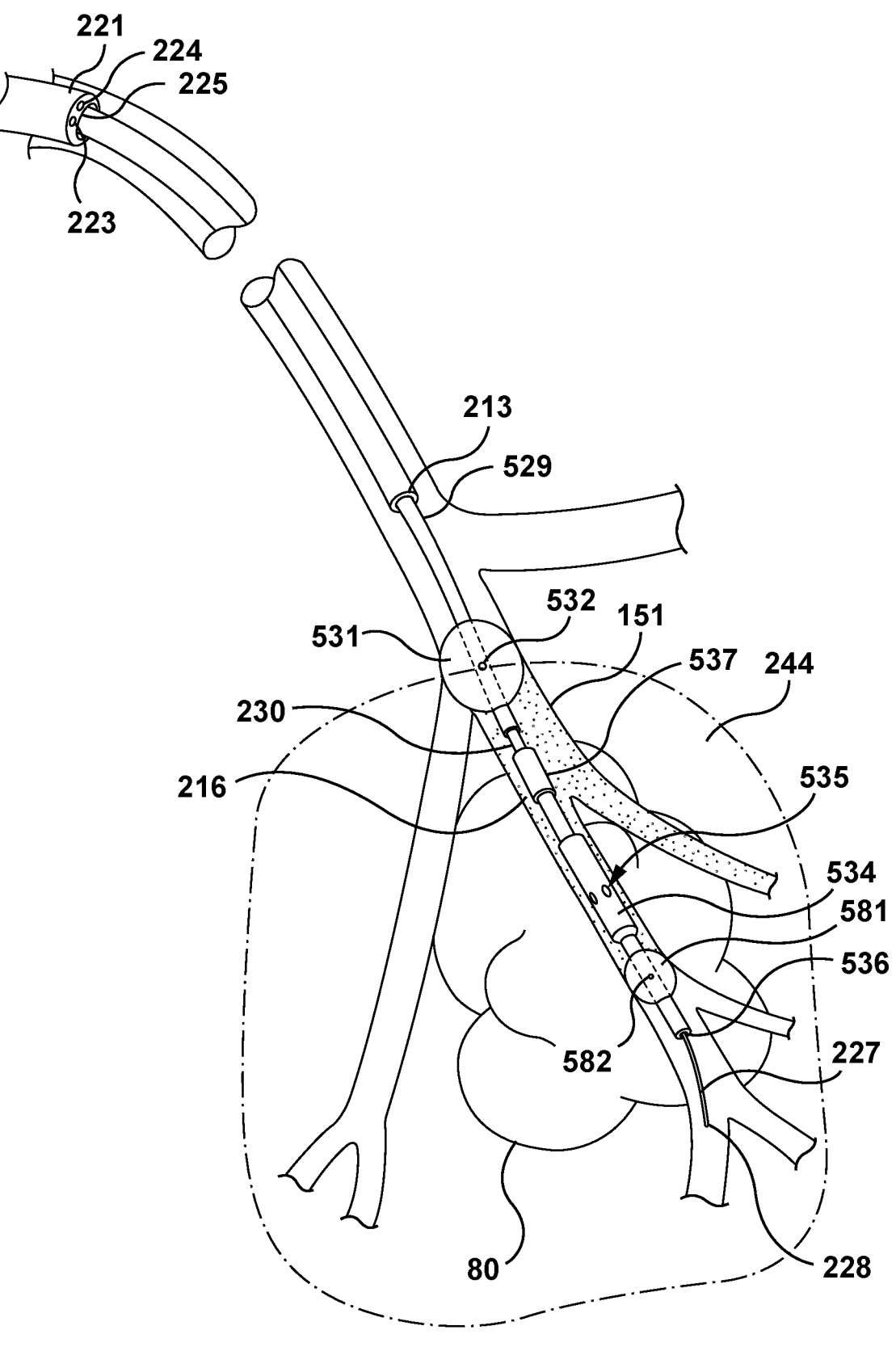
FIG. 6B is a schematic illustration of the device of FIG. 5B in situ.

FIG. 6B illustrates the ablation apparatus 520 shown in FIG. 5B introduced into a selected airway 151 comprising an elongated first shaft 529 and the second shaft 230, a proximal obturator 531 and a distal obturator 581 proximal and distal to the electrodes respectively, an air removal port 535 in fluid communication with a lumen (not shown) that is connectable at the proximal region of the device to a suction device (e.g., vacuum pump) to remove air from the airway segment between the obturators 531, 581 to collapse the targeted portion, segment or lobe of the lung. Air may be removed from the targeted lung portion by applying negative pressure (e.g., with the suction device) to the lumen that is in communication with the air removal port 535, that pulls air from the lung portion through the lumen to a proximal region of the apparatus external to the patient. As shown the air removal port 535 is the same port through which a conductive fluid (e.g., hypertonic saline) may be delivered. Alternatively, air may be removed from the targeted portion of lung by applying suction to a different lumen such as guidewire lumen 536 or an additional lumen (not shown) having an exit port on the second shaft 230 between the obturators 531, 581. Alternative methods of at least partially collapsing a targeted portion of lung are described herein.

Conductive fluid (e.g., 5 to 30% hypertonic saline) may be delivered to the targeted lung portion through irrigation ports 535 in the electrode 534 or additionally or alternatively through an infusion lumen (not shown) exiting the device 520 distal to the occlusion balloon 531 that may or may not exit through ports in an electrode. The infusion lumen runs from the irrigation ports (e.g., 535) through the second shaft 230 to the proximal region of the device where it is connectable to a conductive fluid supply and optionally pump.

A telescopic or adjustable distance between the proximal balloon and the electrode(s), or between the proximal balloon and the distal balloon, may advantageously allow placement of the electrode next to the tumor and placement of the occluding balloons at a desired position, which may depend on the geometry of the airway, the size of targeted lung portion, or the size of tumor. Especially, the adjustable distance between the proximal obturator and the distal obturator allows a more specific segment of an airway to be isolated, so any risk or unwanted influence related to the operations, such as air evacuation, fluid infusion or ablation, will be significantly reduced or minimized Optionally, the second shaft 230 may be deflectable or rotatable with respect to the first shaft 529. The ablation electrode(s) 534 may optionally comprise at least one irrigation port 535 for irrigating the electrode.

The dual obturator structure may provide some further advantages such as the following:

Reduced influence from collateral ventilation. Collateral ventilation is a common physiological function of a lung. During collateral ventilation, air is able to travel between lobes, bronchioles or alveolus through inter-bronchiolar passages in a lung. Although the collateral ventilation air flow is minor compared to normal respiration, it can still have effects on sufficient local air evacuation or fluid infusion. The dual obturator structure is able to provide a more sequestered space in the targeted airway. In this isolated airway segment, the influence from collateral ventilation may be minimized More focused therapy to the local area. In the isolated airway segment, air evacuation and conductive fluid infusion can be applied to this specific position, and the ablation energy can be more focused on this position. The obturators may also act as object blockers or energy sealants, which can reduce any air, fluid or energy diffusion effect and can save energy as well.

Reduce the risk of generating unwanted damage to pleural tissue. The dual obturator structure can provide additional fixing points to further stabilized the ablation catheter. Especially, the distal section of the ablation catheter, which comprises the ablation electrode, ablation needle or guide wire tip, is free to deform or tilt within the original strength limit of the catheter. Any accidental movement of the catheter distal section, for example, shaft 429, 529 elongation and distal tip migration due to uneven passive force during air evacuation or fluid infusion, is possible to generate unwanted damage (e.g. piercing, friction or granulation, tissue deformation) to the pleural tissue, effecting the ablation results and causing additional treatments or remedies. Furthermore, it may be desired to avoid delivering hypertonic saline or heat to pleurae or to lung parenchyma immediately next to the pleurae. A distal occlusion balloon may reduce the risk of injuring the pleurae via thermal energy or dehydration from hypertonic saline by holding the infused hypertonic saline a safe distance away from the pleurae. For example, a distal occlusion balloon may have a length of at least 10 mm, which is expected to be a safe distance from the pleurae. If the distal end of the device is inserted all the way to a distal end of an airway which may be within 10 mm of a pleura and a distal occlusion balloon is inflated, the infusion of hypertonic saline and delivery of heat may be expected to remain a safe distance from the pleura.

Using the above described ablation catheters, a method may be performed of ablating lung tumor cells by sequestering a target portion of lung proximate the tumor cells, delivering hypertonic saline (HTS) to the sequestered portion of lung, and applying heat to the sequestered portion of lung. The HTS may have a sodium (NaCl) concentration of at least 3% w/v (e.g., in a range of 3% to 30% w/v, in a range of 5% to 25% w/v)

The HTS may be heated in a target region of the lung to a range of 60 to 115° Celsius. The heat may be applied by delivering radiofrequency (RF) electrical current from an RF electrode on the catheter to the HTS liquid injected into a natural airway of the lung that is near the lung tumor. The target region of lung may be exposed to heat and HTS for a duration of in a range of 30 seconds to 30 minutes (e.g., a range of 1 to 30 minutes, a range of 1 to 15 minutes, a range of 2 to 10 minutes).

The application of RF energy into the liquid effectively uses the liquid as a virtual electrode to deliver energy to ablate tumor cells. The HTS solutions conducts the RF energy to the lung tissue which causes the tissue to heat. Also, some of the RF energy heats the liquid such that the heated liquid can ablate tumor cells.

The target portion of lung is sequestered by inflating a first occluding balloon in a natural airway, wherein the balloon is proximal to the target portion of lung. Further, a second (distal) occluding balloon in the airway distal to ablation electrode may also be used to occlude the airway. The one or both balloons occlude the natural airway form a portion of the airway in which the HTS solution is injected and suppress flow of the liquid outside of that portion of the airway.

Alternatively or additionally, a fiberoptic lens may be positioned on the first elongated shaft 529 distal to the proximal occlusion structure and another lens may be positioned on the second shaft 230 distal to the distal occlusion structure, which may be used to visualize the airway distal to the selected occlusion structure(s). This may also facilitate, for example, confirmation of airway shrinking, position of the electrode(s), or injury to the airway while the occlusion structure is deployed.

Alternatively or additionally, a lung portion may be collapsed by creating a limited, controlled pneumothorax by placing a needle in the pleural space (e.g., in a pleural recess), which can facilitate collapsing the targeted lung portion. Thoracentesis (a.k.a. pleural tap) is a known procedure to remove fluid or air from around the lungs in which a needle is inserted through the chest wall into the pleural space. This may be done to alter the pressure differential between the pleural space and lung portion allowing it to collapse more easily. Optionally, a dispersive return electrode may be inserted through the pleural tap and positioned on the lung to direct RF current preferentially toward the return electrode. Optionally, a pleural tap may be used to deliver cold fluid such as physiological saline or sterile water to thermally protect areas from ablation, in particular when the tumor is at the periphery of the lung and there is a risk of ablating visceral pleura or organs such as the heart, esophagus, nerves, diaphragm or other important non-target tissues.

Optionally, any occlusion balloon may have a micropatterned surface on the exterior surface where the balloon is intended to contact an airway wall. The micropatterned surface may be molded to the balloon material and may have a hydrophilic surface that increases surface water tension creating a higher retention force that improves the ability of the occlusion balloon to remain anchored in its intended location. The improved retention may also reduce the risk of fluid leaking past the balloon. The micropattern may have a plurality of pillars having height and width dimensions less than 1000 nanometers. For example, a micropattern may be molded to the membrane using techniques known in the art (e.g., U.S. Pat. No. 8,720,047 assigned to Hoowaki, LLC)

Embodiment #2 (Needle Electrode for Puncturing Tissue and Placement in a Tumor or Lung Parenchyma)

Figure 8:
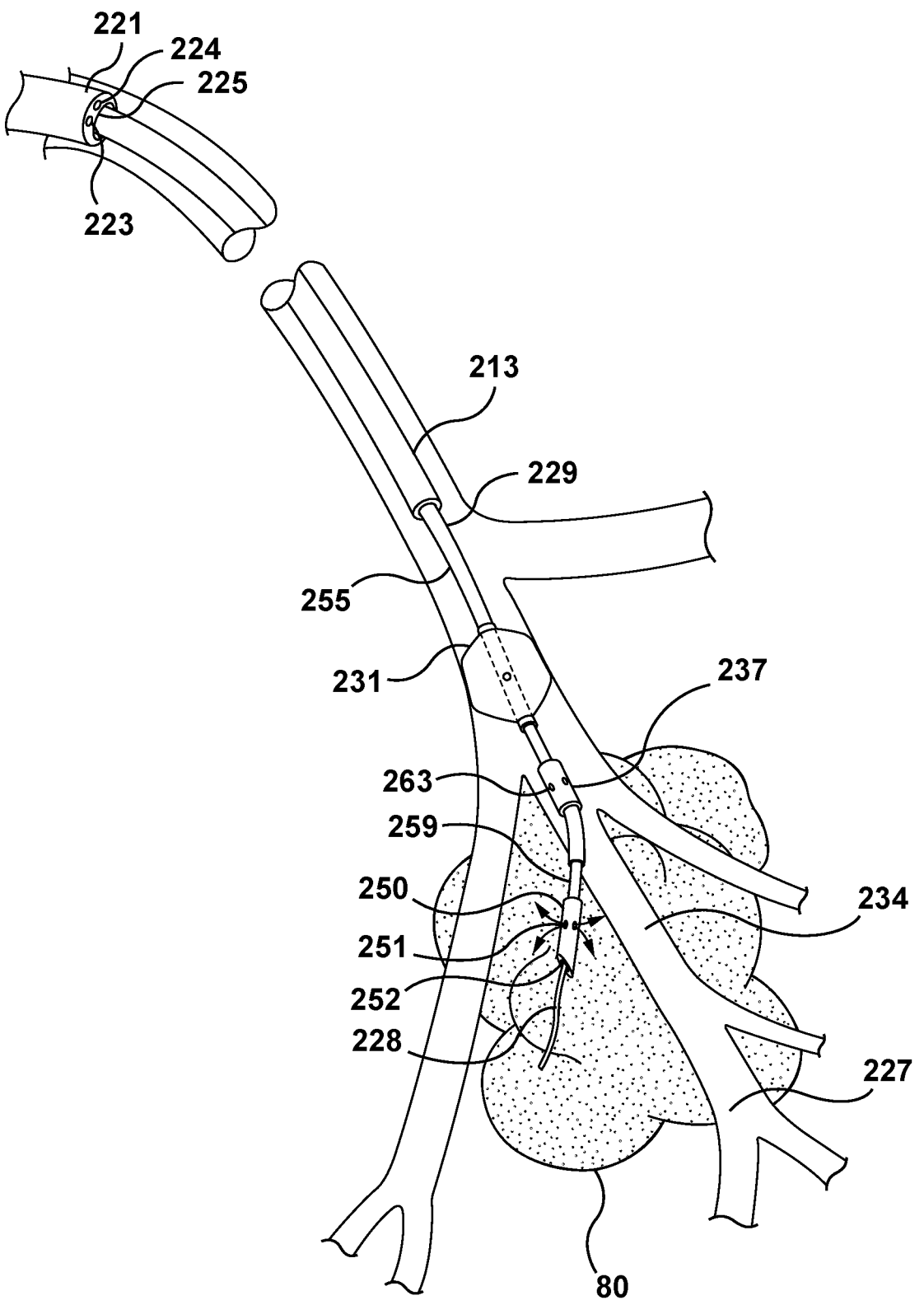
FIG. 8 is a schematic illustration of the device of FIG. 7 in situ.

Alternatively, as shown in FIGS. 7 and 8 the at least one RF electrode 234 of the embodiment shown in FIG. 3 or 4A may be at least one needle electrode 250 used to puncture through the airway wall or through a tumor to position the RF electrode 250 in the targeted tumor 80 or in lung parenchyma near the tumor. The needle electrode 250 may have irrigation ports 251 in fluid communication with an irrigation lumen passing through the shaft 229 to the proximal region of the catheter. The needle electrode 250 may have a length in a range of 3 to 20 mm (e.g., 5 to 15 mm, about 7 mm), and a diameter in a range of 0.5 mm to 2 mm (e.g., about 1.35 mm). Optionally, the needle electrode may have a guide wire lumen 252 (e.g., having an inner diameter of 0.015" to 0.030") allowing the device to be delivered over a guidewire 228. The tip 253 of the needle electrode 250 may be sharp so it can puncture through the airway wall or tumor, for example the tip 253 may be bevel cut as shown or other sharp profile such as pencil tip. In use, conductive fluid (e.g., 5 to 30% hypertonic saline) may be injected from the irrigation ports 251 into lung parenchyma or the tumor when the needle electrode 250 is positioned in the parenchyma or tumor as shown in FIG. 8.

Optionally, the device 255 may be delivered over a guidewire that is left in place in lung parenchyma or a tumor following a biopsy so the needle electrode 250 can easily be placed in the same location that the biopsy was taken.

Optionally, the distal region 256 of the device 255 having a needle electrode 250 may have a spring loaded mechanism with a spring 257 and an engagement lock 258 that holds the needle electrode 250 in a first spring loaded position and when the lock 258 is released by an actuator on the proximal region of the device 255 the spring 257 pushes a shaft 259 on which the needle electrode 250 is mounted thus extending a distance 260 from a spring loaded state (e.g., 5 to 10 mm) to a deployed state (e.g., an increase of 5 to 15 mm). The momentum provided by releasing the spring-loaded mechanism may facilitate puncture of the airway wall by the needle electrode 250. The engagement lock 258 may be a mechanical mechanism such as a pivoting lever that mates with an element firmly connected to the distal shaft 259. The pivoting lever may be connected to a pull wire 261 that runs through the device shaft 229 to the proximal region of the device where it may be connected to an actuator that may be used to apply tension to the pull wire to release the lock mechanism 258.

In an alternative embodiment of a lung cancer ablation catheter capable of puncturing through an airway wall may have an RF perforation electrode on its tip (e.g., 0.5 mm diameter, 1 mm length) and the outer diameter of the shaft may taper from the RF perforation electrode diameter to the diameter of a distal ablation electrode (e.g., about 1.5 mm). An RF perforation electrode may be connectable to an energy delivery console that has an RF perforation mode. RF perforation electrodes and energy delivery profiles are known for example in the field of cardiac procedures such as septum perforation.

Optionally, the distal region of device having needle electrodes may be deflectable which may facilitate directing the sharp tip toward an airway wall in order to puncture through the wall or into a tumor and place the needle electrode 250 in lung parenchyma near or in a lung tumor or within the tumor itself.

Optionally, the proximal electrode 237 may be used to deliver ablative RF energy in addition to, instead of, or in conjunction with the distal electrode 250. The proximal electrode 237 may optionally have irrigation ports 263 in fluid communication with an irrigation lumen (not shown) that passes through the shaft 229 to the proximal region of the device 255 where the lumen is connectable to a conductive fluid source or pump. The irrigation ports 263 and 251 on the proximal electrode 237 and distal electrode 250 may be connected to the same irrigation lumen or separate lumens for delivery of conductive fluid. In embodiments having irrigation ports 263 on a proximal electrode 237 as well as irrigation ports 251 on a distal needle electrode 250 as shown in FIG. 8 conductive fluid may be delivered from either ports 251 or 263, preferably from both, into the lung parenchyma or tumor and/or into airways distal the obturator 231. Preferably, RF energy may be delivered to the two electrodes 237 and 250 in dual-channel monopolar RF mode. For example, each channel may have a completed circuit with a dispersive electrode on the patient's skin or in the body and channels may float with respect to one another. Alternatively, an ablation energy console may delivery RF energy to the two electrodes 250 and 237 in bipolar mode.

Embodiment #3 (Ablation Electrode(s) on a Plurality of Shafts)

FIG. 9 shows two catheters 100 and 101 with energy delivery electrodes 102 and 103 as an example that can be introduced separately using a flexible bronchoscope 221 and positioned with the electrodes terminating in two separate airways on two sides of the targeted tumor 80. The apparatus may include an occlusion catheter 270 that may be delivered through a working channel 225 of a bronchoscope 221 or optionally through a delivery sheath 213. The occlusion catheter 270 may comprise an obturator 271 such as a compliant balloon mounted to the shaft of the occlusion catheter 270. An inflation lumen passes through the occlusion catheter shaft and exits a port 272 within the obturator to deploy or inflate the obturator 271. The shaft of the occlusion catheter 270 may comprise two or more ablation catheter lumens 273 and 274 that exit the shaft distal to the obturator 271. Alternative forms of occlusion elements may be envisioned as disclosed herein. The catheters 100 and 101 may be delivered through the lumens 273 and 274 to the airway distal of the obturator. Lumens 273 and 274 may each have a valve that seals around delivered catheters 100 and 101 to contain low pressure or conductive fluid in the target region of the lung portion. The catheters may be delivered over a guide wire 104 via guide wire lumens 106 and 107. The electrodes may be connected to electrical conductors that pass through the catheter shafts to a proximal region of the catheter for example terminating in an electrical connector, which may be electrically connected to an RF generator for example using a connector cable. Each catheter can incorporate more than one electrode that can be energized together or separately. Optionally, each catheter may have an impedance and phase monitoring electrode 275 and 276 for monitoring tissue impedance and phase between distal electrode 103 and impedance electrode 276 or distal electrode 102 and impedance electrode 275 to assess collapse of airways, infusion of conductive fluid, tissue properties, or degree of ablation of tissue. Conductive fluid 216 may be injected into the targeted lung portion that is occluded with obturator 271 through irrigation holes 277 or 278 in electrodes 102 and 103.

The electrodes of the catheters may be positioned at a desired location in an airway by delivering the catheters 100 and 101 over a guide wire 104 laid down for example using an ultrathin bronchoscope. Catheters 100 and 101 may comprise a guidewire lumen 106 and 107 and be adapted for over-the-wire (OTW) exchange. Currently available devices may be used to navigate to desired positions in the patient's airway. For example, electromagnetic navigation bronchoscopy is a medical procedure utilizing electromagnetic technology designed to localize and guide endoscopic tools or catheters through the bronchial pathways of the lung. Virtual Bronchoscopy (VB) is a three-dimensional, computer-generated technique that produces endobronchial images from spiral CT data. Using a virtual, three-dimensional bronchial map from a recently computed tomography (CT) chest scan and disposable catheter set, physicians can navigate to a desired location within the lung to biopsy lesions, take samples from lymph nodes, insert markers to guide radiotherapy or guide brachytherapy catheters. Such existing technology may be used to plan for a procedure, diagnose a tumor with a biopsy, or place a guidewire for positioning one or more treatment catheters. After a guide wire 104 is placed in an airway near the target ablation zone (e.g., within 0 to 10 mm from the target ablation zone or within the target ablation zone) the ultrathin bronchoscope can be withdrawn with the wire left in place and an electrode catheter may be exchanged over the wire. Alternatively, electromagnetic navigation bronchoscopy may be used with similar results. Optionally, the multiple catheters may alternatively have a dual balloon structure, which is similar to the devices shown in FIG. 5A or 5B.

Multiple catheters with electrodes, or balloon elements, can be placed in the described fashion by exchanging a bronchoscope for catheter over the wire. After the tumor is thus surrounded by energy delivery elements and the bronchoscope and guide wire are removed, the proximal ends of catheters can be connected to the RF generator outside of the body. The technology subject of the present disclosure can also be used to ablate lymph nodes, should biopsy results indicate lymph node metastases.

Radiopaque markers on the guide wire or catheter can be used to position the electrodes at the precise desired location. For example, the RF electrodes may be radiopaque. Any of the ablation catheters disclosed herein may comprise a retention or anchoring mechanism at a distal region of the catheter to ensure its energy delivery element(s) stay in a desired position and avoid accidental dislodgement in particular when the patient breathes or coughs. For example, a retention or anchoring mechanism may comprise a section of the catheter that adopts a predefined non-linear shape (not shown), an inflatable balloon, spring loaded or wire activated splines, a stent, or deployable barbs positioned on the distal region of the catheter. Size and design of the electrode catheter can be made compatible with a working channel of regular or ultra thin bronchoscopes. Multiple electric connections for energy delivery and signal transmission (temperature and impedance) are envisioned. The ablation catheters may comprise a substance delivery lumen, which may be used to deliver substances into the airway such as drugs, contrast media to visualize the anatomy using fluoroscopy, and substances that induce lung collapse. Optionally, the guide wire lumen may function as the substance delivery lumen when the guide wire is removed, which may allow the catheter's diameter to be minimized. The ablation catheters may comprise an irrigation delivery lumen used to infuse irrigation fluid into the airway surrounding the electrodes to prevent charring and impedance rise and enable bigger lesion creation. The irrigation delivery lumen may be the same lumen as the substance delivery lumen or guide wire lumen.

Figure 9:
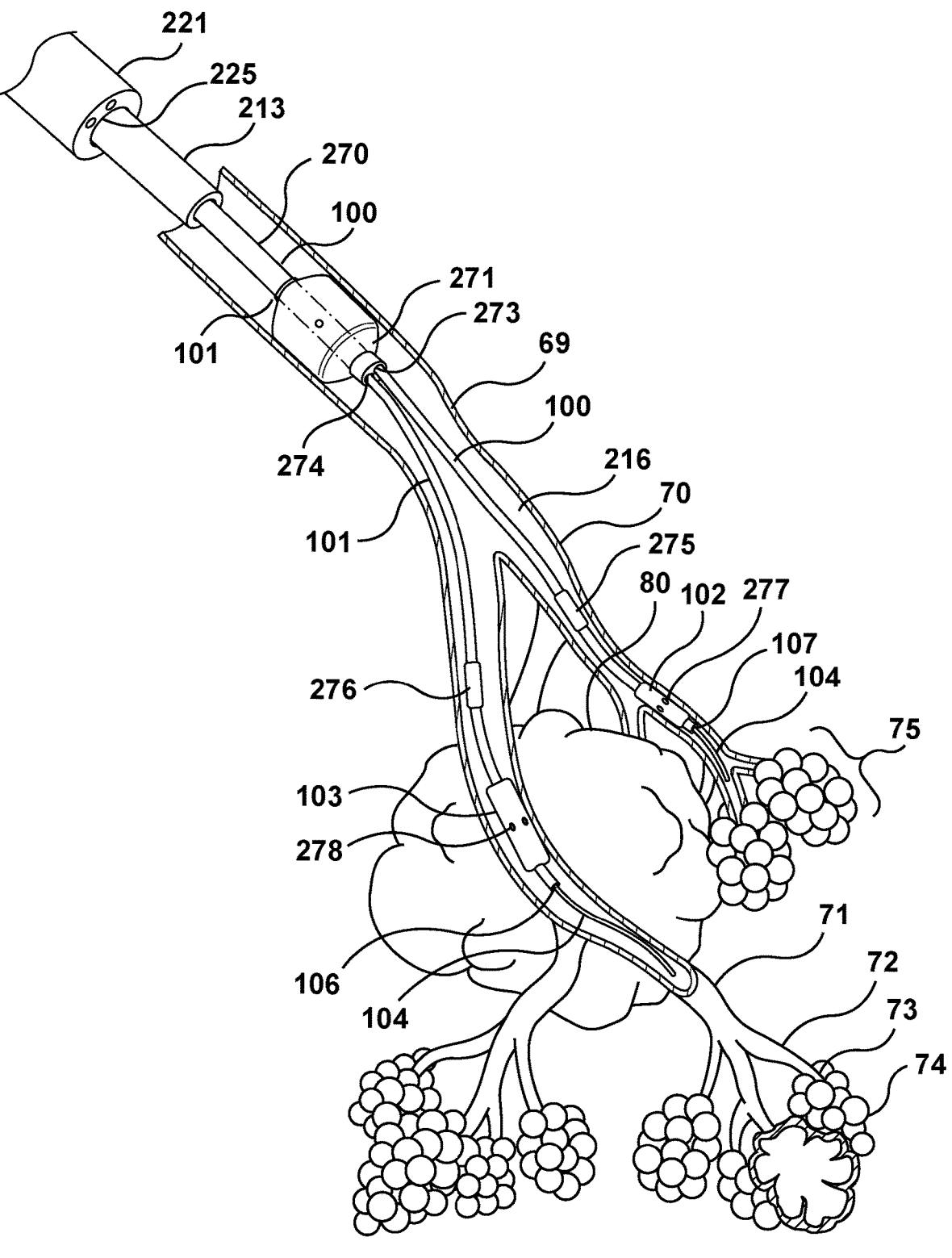
FIG. 9 is a schematic illustration of multiple catheters positioned in a patient's airways to place energy delivery electrodes at different locations associated with a targeted tumor.
Figure 10A:
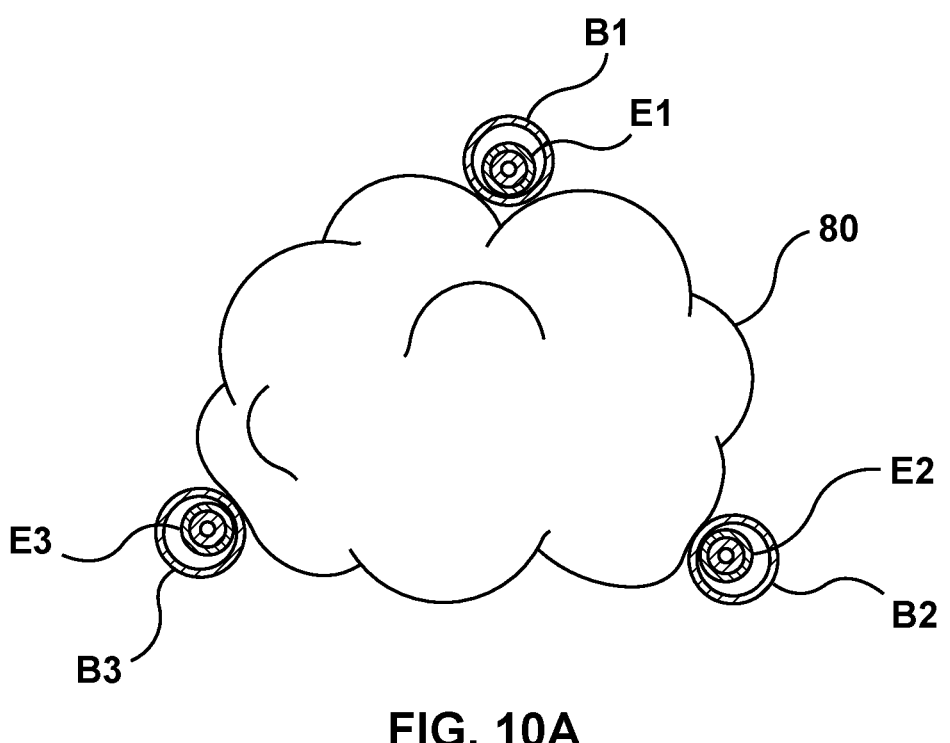
FIG. 10A is a schematic illustration of a cross section of FIG. 9.
Figure 10B:
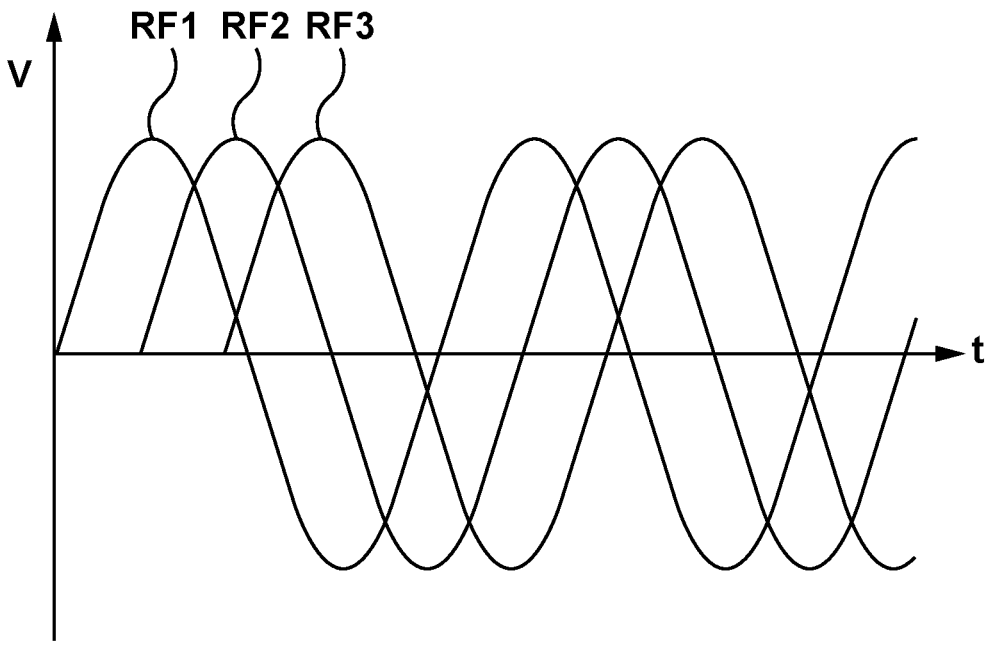
FIG. 10B is a plot of a multiphasic waveform.
Figure 10C:
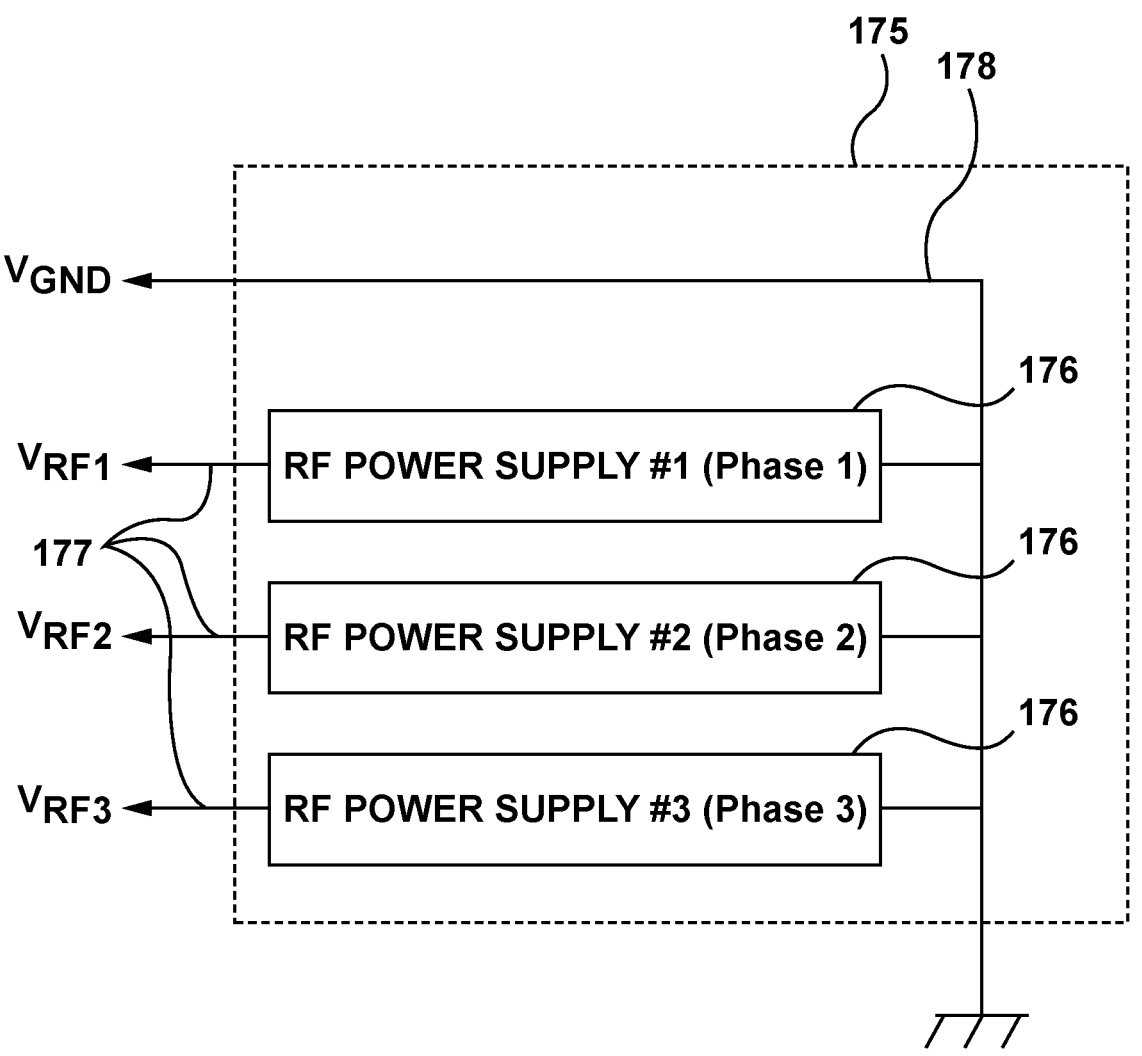
FIG. 10C is a schematic of a multiphasic RF system.
Figure 10D:
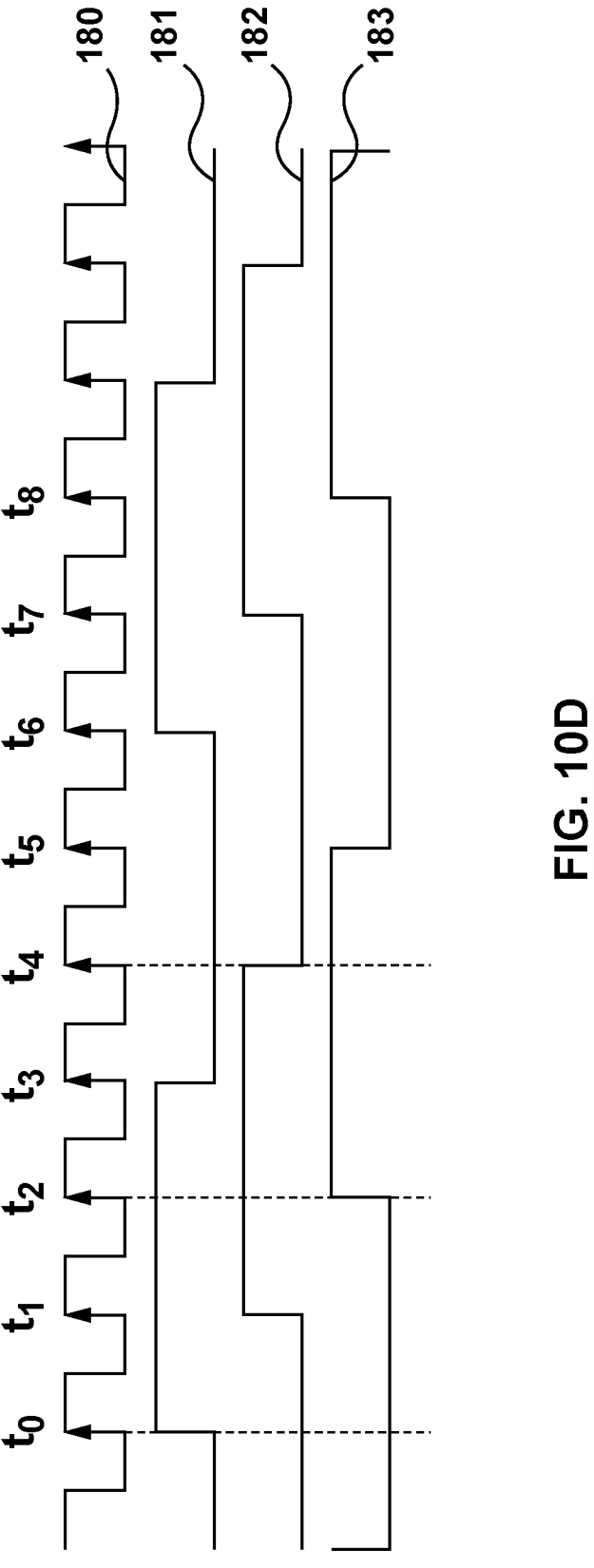
FIG. 10D is a plot of a digital clock divided to generate a multiphasic RF configuration.

As shown in FIG. 10A three RF electrodes labelled E1, E2 and E3 are positioned in three separate airways labeled B1, B2 and B3. For example, the three electrodes may be delivered on separate catheters, such as the catheter embodiment shown in FIG. 9. Multiphasic RF ablation waveforms may be used to set a rotating ablating electrical field, which delivers ablating energy to the tumor in a more localized modality. FIG. 10B illustrates a multiphasic RF waveform that may be used to ablate a targeted tumor encompassed by multiple RF electrodes, wherein RF1 is an RF signal delivered to electrode E1, RF2 is delivered to electrode E2, and RF3 is delivered to electrode E3. In this example, waveforms RF1, RF2 and RF3 are 120° phase shifted apart. Application of such phased-shifted waveforms creates a rotating multipolar ablation field, which enhances the coverage of the tumor space and has the potential of providing more uniform lesions. In principle, phased RF ablation works similarly to bipolar ablation, except that electrical currents flow from or to a multitude of electrodes in a sequence dictated by phase differences. Each electrode is driven by an RF source having a different phase. The RF voltage resulting between each pair of electrodes (e.g., E1-E2, E2-E3 and E3-E1) drives RF current to flow in more uniform heating patterns in the tumor space. Power levels range between 1 to 200 W, with durations between 30 seconds to 30 minutes. Temperature sensors may be employed with an intent to control local temperature values around a user-defined target. Temperature of such targets may vary in a range of 60 to 115° C., preferably in a range of 50 to 80° C. RF generators capable of delivering phased ablation energy may have additional RF output stages. FIG. 10C shows an example of a multiphasic RF energy supply 175 where each output 177 has an independently controlled phase. The phase of RF signals at each output may be controlled by separate RF power supplies 176, or alternatively a central microcontroller, via software, or by hardware, for example by dividing a digital clock of a higher frequency, as shown in FIG. 10D. As shown in FIG. 10D a digital clock may comprise a base frequency 180 having a period (e.g., from t0 to t1) that is one sixth the period of frequencies 181, 182, and 183, which are delivered to the ablation electrodes and offset by one base period. Optionally, each electrode E1, E2, and E3 (and respective RF output voltages VRF1, VRF2 and VRF3) may complete an electrical circuit with a dispersive ground pad connected to ground voltage VGND at a terminal 178 of the RF energy supply 175. An alternative embodiment may comprise greater than three electrodes and waveforms or less than three (e.g., two electrodes and waveforms).

An example of bipolar or multipolar RF ablation parameters that an RF console delivers to multiple electrodes, or to multiple balloons, or to combinations of balloon and electrode energy elements, may comprise power in a range of 1 to 200 W for a duration of 30 seconds to 30 minutes. Tissue impedance may be expected to be in a range of 30 to 1000 ohms and the system may terminate or reduce power delivery if a high impedance (e.g., above 1000 ohms) is detected to avoid tissue char or uncontrolled ablation due to overheating, poor electrode contact with an airway wall. After desiccated tissue is rehydrated naturally or by irrigation, energy delivery can automatically resume. Impedance monitoring may also be used during energy delivery to determine if tissue temperature has raised sufficiently for an effective tumor ablation and instigate completion of energy delivery. The parameters may be used in a multiphasic RF ablation waveform or monophasic waveform.

Optionally, an ablation energy console may delivery ablation energy to multiple RF electrodes (e.g., on a single ablation device or on separate ablation devices) in multichannel monopolar mode and independent waveforms (e.g., VRF1, VRF2, etc. shown in FIG. 10C) may be in-phase.

System

Figure 11:
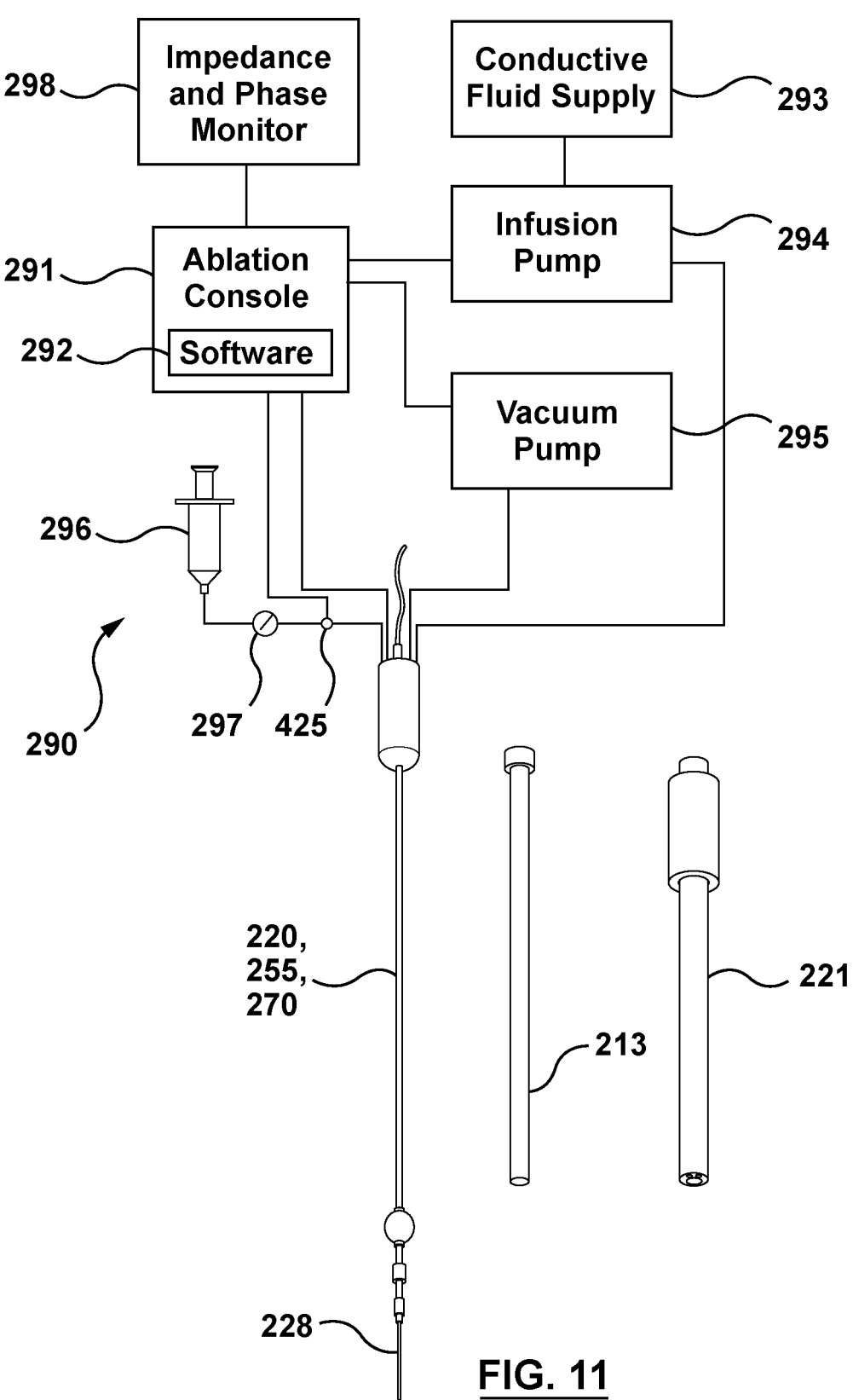
FIG. 11 is a schematic illustration of a system for operating endobronchial lung tumor ablation devices.

Devices for Endobronchial lung tumor ablation such as those disclosed herein (e.g., device 220, 255, or 270) may be part of a system 290 as shown in FIG. 11 further comprising an computerized ablation energy (e.g., RF) console 291 comprising a programmable controller with software 292, a conductive fluid supply 293 and pump 294, a vacuum pump 295, an obturator inflator 296 (e.g., insulflator, syringe with valve 297, motorized pump, motorized valve to pressurized fluid) and associated connector cables and tubes to connect the proximal region of the device to the console, pump, or vacuum pump.

Optionally, the system 290 may include more than one ablation device for example multiple ablation devices 100 and 101 deliverable through an occlusion catheter 270 as shown in FIG. 9, or multiple ablation devices such as 220 or 255. The system 290 may also include a guidewire 227, a delivery sheath 213, a dispersive grounding pad, or a bronchoscope 221. The ablation console 291 may further comprise an impedance and phase monitoring circuit and software 298 that is connectable to electrodes on ablation device (220, 255, 270), measures impedance and phase and displays their values to user. Optionally, an impedance and phase monitoring circuit and software 298 may be in a separate component, which may be connected to the ablation console to input measured impedance or phase to control algorithms of the Ablation console software 292.

A system may include an ablation console 291, a pump 294, controller software 292, and optionally impedance and phase monitoring circuit and software 298, or any combination thereof. Furthermore, the ablation console 291, a pump 294, controller software 292, and optionally impedance and phase monitoring circuit and software 298 may be provided separately.

The software 292 may include an algorithm that controls the vacuum pump 295 to remove air from the targeted lung portion. The vacuum pump may have a pressure sensor that indicates the difference in pressure between atmosphere and the targeted lung portion. The vacuum pump may apply a maximum negative pressure difference in a range of 1 to 5 atm and the algorithm may input the pressure difference and shut off the vacuum pump when the pressure difference reaches the maximum negative pressure difference, at which time the vacuum pump may be signalled to seal air flow from the lung portion to maintain the pressure in the lung, for example by closing a valve. In embodiments wherein the conductive fluid is infused through the same lumen through which air is removed from the lung, the system may have an automatically controlled switching valve that switches fluid communication from the vacuum pump to infusion pump, for example once the algorithm detects sufficient lung portion collapse either via pressure sensor signal or tissue impedance and phase associated with the distal and proximal electrodes on the device (e.g., 220, 255, or 270). For example, the software 292 may control the ablation console 291 to deliver electrical waveforms (e.g., low power high frequency current over a range of frequency) to the distal and proximal electrode to monitor tissue impedance or phase during operation of the vacuum pump 295 and control the vacuum pump to stop when an impedance drop signifies lung collapse. The software 292 may control the pump 294 to pump conductive fluid from the fluid supply 293 to the device and into the targeted lung portion and optionally may deliver electrical waveforms to concurrently monitor impedance or phase to assess infusion. Optionally, infusion may continue (e.g., at a rate of about 5 mL/min) during delivery of ablation energy from the console 291. The software 292 may further control ablation energy delivery profiles including safety monitoring of temperature and impedance.

Alternatively, negative pressure may be manually applied to remove air from the targeted lung portion by drawing air through the catheter (e.g. through irrigation ports 235 and irrigation lumen) with a manual suction tool. The manual suction tool may be a syringe and may further have two check valves that allow air to be pulled from the catheter when the syringe is drawn and ejected to atmosphere when the syringe is depressed. A pressure sensor may be positioned in the irrigation lumen. In use, a physician may position the ablation catheter in a patient's lung, deploy the obturator, then manually apply suction to the manual suction tool while monitoring bipolar impedance measured by delivering low electrical current and measuring tissue impedance between the proximal and distal electrodes, and optionally pressure measured by the pressure sensor. A 5% to 20% drop in impedance may indicate the airway has sufficiently collapsed to proceed. Following the application of suction and identification of sufficient collapse via impedance or pressure drop a user may hold the suction tool in a static setting while monitoring impedance or pressure. A stable impedance or pressure may indicate that the targeted lung portion remains sufficiently collapsed. A rise in the impedance or pressure during this stage may indicate that the obturator is not sufficiently occluding the airway and the user may remedy by repositioning, examining, or reinflating the obturator.

If suction is applied manually a user may initiate an algorithm (e.g., by pressing an actuator on the ablatio console) when they are satisfied the targeted lung portion is sufficiently collapsed. If suction is applied automatically by an algorithm of the software 292 the algorithm may send a user message indicating the impedance or pressure drop during the suction stage is sufficient to proceed to ablation and the user may active the ablation stage (e.g., by pressing an actuator on the ablatio console) allowing the algorithm to continue.

An algorithm of the software 292 may direct the flow rate of infused conductive fluid by controlling the speed of the pump. During an ablation stage the algorithm of the software 292 may enter a priming stage that instructs the pump 294 to deliver conductive fluid from the conductive fluid source 293 without delivering ablative RF energy to prime the infusion lumen with conductive fluid and ensure at least a small amount of conductive fluid is in the airway of the targeted lung portion before ablative RF energy begins to be delivered. For example, the priming stage may include infusion of conductive fluid at a rate of 5 mL/min for 5 seconds or until measured impedance drops another 10% to 20% up to a maximum duration (e.g., 15 seconds). A drop in impedance of at least 10% may indicate that the irrigation is working properly. If impedance does not drop during this priming stage the algorithm may send a user error message indicating a possible problem with irrigation, the fluid pump, or the conductive fluid supply. If an impedance drop (e.g. of at value in a range of 10% to 20%) is measured during the priming stage the algorithm may continue to an ablation RF delivery stage.

In one embodiment, during the ablation RF delivery stage the rate of irrigation of conductive fluid may begin at 0 mL/min as ablative RF begins to be delivered. This may help to minimize the amount of conductive fluid delivered. During delivery of ablative RF, temperature, monitored by a temperature sensor 242, 442, 542, 262 associated with the ablation electrode 234, 434, 534, 250 may be input into the control algorithm and when the temperature increases to a predefined upper threshold temperature (e.g., 95° C.) irrigation flow may be turned on (e.g., at a rate of 5 mL/min) while continuing to deliver RF energy at a consistent power. The irrigation is expected cool the ablation electrode keeping it below the upper temperature threshold. If the measured temperature decreases to a predefined lower threshold (e.g., 85° C.) then irrigation flow may be instructed to stop or decrease, while maintaining constant RF power, allowing temperature to rise. The algorithm may continue to adjust flowrate to keep the temperature within the upper and lower thresholds until a preset ablation duration is reached or other termination trigger occurs. Other termination triggers may include the user manually terminating the ablation by depressing the ablation RF power actuator or an automatic shutoff error triggered by the algorithm. Automatic shutoff errors may be caused by an inability to maintain temperature within the upper and lower thresholds, failure of a component of the system (e.g., insufficient conductive fluid supply, pump malfunction, valve malfunction).

Ablation duration may be in a range of 30 seconds to 30 minutes and optionally may be chosen by a physician based on desired ablation size. For example, with animal and bench models, the authors have empirically demonstrated that using 5% HTS with an ablation electrode 234 that is 5 mm long and 1.5 mm diameter a 5 minute ablation generates a spherical ablation approximately 1.5-2 cm in diameter; at least 7 minutes results in a 2-2.5 cm diameter ablation; at least 10 minutes results in a 2.5-3 cm ablation; at least 15 minutes results in a 3 cm, or larger, diameter ablation. Depending on the size of the tumor and location relative to the target airway a physician may choose the appropriate ablation duration to encompass the tumor and input the duration to the algorithm using a user interface on the console 291. The algorithm may display on the user interface the chosen duration and estimated ablation diameter according to the input duration. Alternatively, a physician may input a desired ablation dimension (e.g., diameter) to the algorithm and the duration may be calculated and displayed. A physician may create a treatment plan depending on the size of the targeted tumor and location of the tumor. The treatment plan may include desired ablation size and placement in the airway relative to the tumor and optionally may include multiple ablations from different target positions in the lung to ablate the tumor from multiple directions if a single ablation is not estimated to completely encompass the tumor.

Optionally, following the termination of ablative RF delivery (e.g., ablation duration has completed or a premature ablation termination is triggered), suction may be activated by the algorithm to remove the conductive fluid that was infused.

Alternatively, the software 292 may control rate of delivery of conductive fluid (e.g., via pump speed) during delivery of ablation energy based on electrode temperature feedback from a temperature sensor (e.g., 242, 262) to obtain a temperature set point. For example, a constant power may be delivered and a constant infusion flow rate may be delivered and as a temperature set point is approached power, flow rate or a combination of both may be titrated to achieve the temperature set point. If actual electrode temperature is below the set point, infusion rate may be decreased and/or power may be increased. If actual electrode temperature is above the set point, infusion rate may be increased and/or power may be decreased.

Optionally, the obturator inflation pressure may be monitored by a pressure sensor 425 positioned in the obturator inflation lumen between the obturator inflator 296 or valve 297 and the obturator 231, 431, 481, 531, 581. Obturator inflation pressure may be input and monitored by the software algorithm 292 and optionally used by the algorithm for example to display the pressure on a user interface, as a requirement to begin vacuum suction (e.g., balloon inflation pressure may need to be above a predefined threshold such as 2 ATM), or as detection of a failure mode (e.g., sudden drop in balloon inflation pressure may indicate rupture of the obturator which may trigger termination of RF delivery).

A conductive fluid such as hypertonic saline may have a boiling temperature higher than 100° C., which may allow greater ablation energy to be deposited into the conductive fluid as well as a higher fluid temperature to facilitate ablation of target tissue. This may be particularly valuable when delivering thermal and electrical energy through cartilaginous airway walls to ablate a tumor, since the airway walls have a relatively low thermal and electrical conductivity and tumor ablation requires a large ablation. For example, a conductive fluid such as 20% hypertonic saline may have a boiling temperature in a range of about 105° C. to 110° C.

It may be advantageous to generate steam in an occluded target region of a lung by raising the temperature of the conductive fluid that is injected in the region close to its boiling point. Generating steam and trapping it in the target region of the lung with the occluding device (e.g., balloon) may increase the vapor pressure of the conductive fluid and, thereby, further raise its boiling point, which may allow greater ablation energy to be delivered. Exposing the airway cartilaginous wall to temperatures around 100° C. for an extended period of time, for example 2 to 10 minutes, provides the advantage of softening its consistency and of allowing conductive fluid to better infiltrate and advance towards the targeted lung tissue. Furthermore, when lung parenchyma is heated it shrinks and airways connected to the parenchyma are pulled closer together. Steam produced in a targeted lung region may pass to the associated parenchyma and shrink it prior to or during delivery of ablation energy, which may improve effectiveness of tumor ablation. An energy delivery console may comprise an energy delivery control algorithm that allows temperature set point that is within a close range about the boiling point of the conductive fluid at the pressure of the fluid in the target region. Optionally, an algorithm may have a steam-producing phase that delivers energy with a temperature set point suitable to generate steam (e.g., if 20% hypertonic saline is the conductive fluid, a temperature set point for a steam-producing phase may be in a range of 100° C. to 110° C., preferably around 105° C.). The ablation of targeted lung tissue may be performed at such increased temperature setpoint and last for a duration of 1 to 10 minutes. Alternatively, the steam-producing phase may have a predefined duration (e.g., up to 2 minutes) or be controlled by monitoring impedance between electrodes in which spikes of high impedance may indicate steam production. Yet alternatively, phases of steam production may be alternated with ablation phases of decreased temperature set points. For example, energy delivery in the first 2 minutes may be performed with a 105° C. set point, in the subsequent 2 minutes with a 85° C. set point, in the subsequent 2 minutes with a 105° C. set point and so on until the ablation duration (e.g., a total duration in a range of 8 to 15 minutes or about 10 minutes) expires or the therapeutic goal is achieved (e.g. moving average impedance increases over a targeted threshold). Optionally, a pressure sensor on the distal region of the device may be used to input a pressure signal to the controller and a rise in pressure can indicate adequate steam production. Optionally, a steam-producing phase may involve heating the conductive fluid by delivering ablation energy from the ablation elements or alternatively by delivering thermal energy from a direct heat resistive coil positioned on the device distal to the occluding device. A direct heat resistive coil may be an electrically resistive metal with an electrical insulation (e.g., polyimide, Parylene) coiled around the device shaft, which heats the conductive fluid by thermal conduction only. A steam-producing phase may be followed by a tumor ablation phase that may have a temperature set point that is lower than the set point of the steam-producing phase, as presented above.

When a conductive fluid is injected to the target region, a control algorithm may use a target set temperature in a range of 85° C. to 115° C., preferably 90° C. to 105° C., to remain below the boiling point of the conductive fluid. Alternatively, it may be desired to generate steam in the occluded target region in which case a set temperature may be in a range of 105° C. to 115° C., provided that sufficient safety mechanisms are designed into the system, such as fast RF energy shut-offs triggered by rapidly rising impedance, temperature or sudden changes in the electrical phase (i.e., the phase between the ablating current and ablating voltage).

Figure 15:
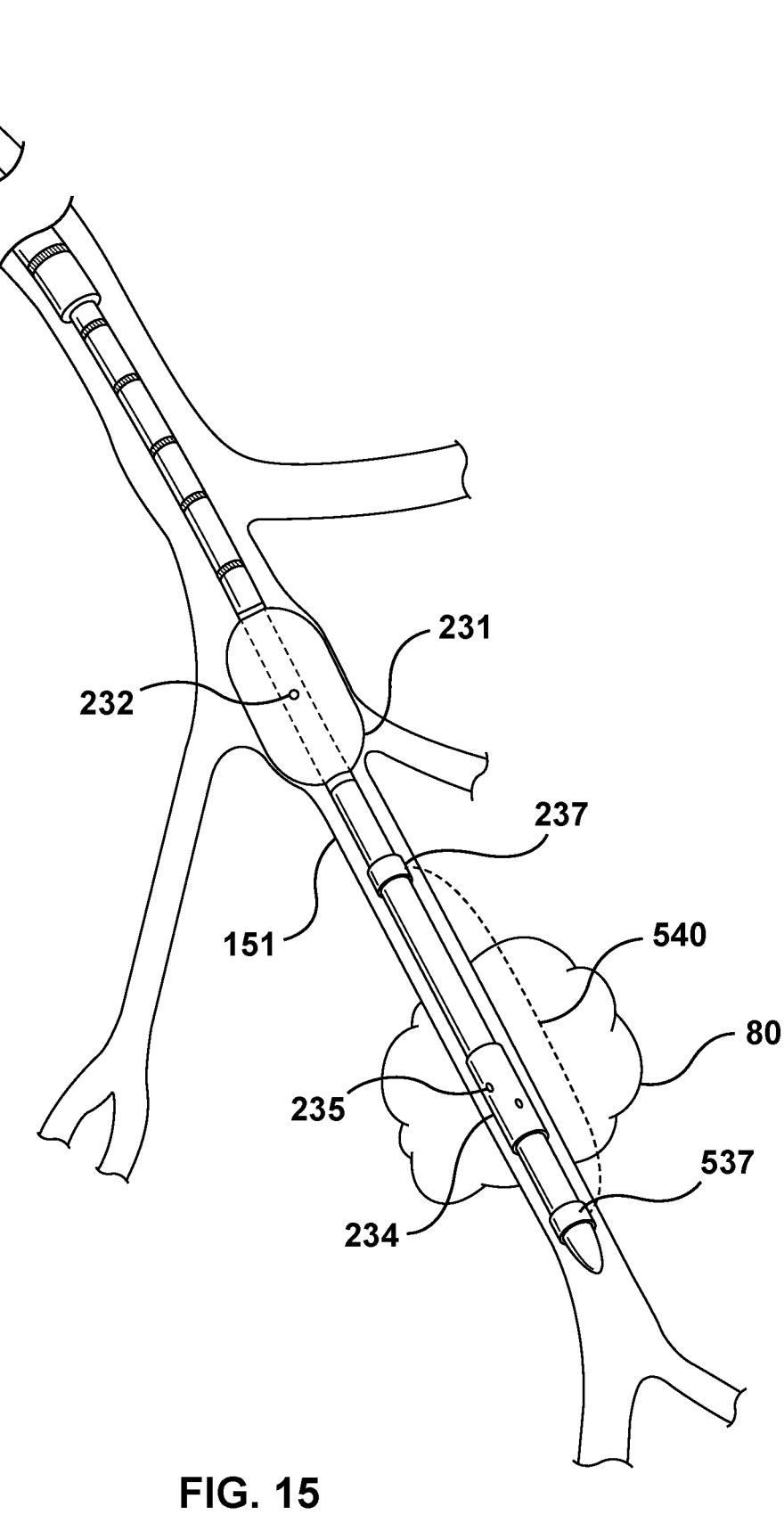
FIG. 15 is a schematic illustration an ablation catheter having an ablation electrode between two impedance monitoring electrodes in situ.

As discussed herein, electrical impedance and phase may be measured between the proximal and distal electrodes or between either of these and a dispersive electrode (e.g., grounding pad positioned on the skin). Impedance spectroscopy may be calculated by a software algorithm in the ablation console 291 to characterize the tissue near the impedance monitoring electrode(s) through which electrical current is delivered. The tissue may be characterized to identify cancerous tissue compared to ablated cancerous tissue compared to normal tissue. Optionally or alternatively, as shown in FIG. 15 an ablation catheter may have a third electrode 537 positioned distal to the ablation electrode 234 in addition to a proximal electrode 237. Other components of the device may be similar to the embodiment shown in FIG. 3 and callout numbers other than the third electrode 537 remain the same as in FIG. 3. In FIG. 15 the third electrode 537 may be positioned on a first side (e.g., distal side) of the targeted tumor 80 while the proximal electrode 237 is positioned on a second side (e.g., proximal side) of the tumor 80, which may position the ablation electrode 234 between the two impedance monitoring electrodes 237 and 537, for example within the tumor 80. In this configure electrical current passed between the electrodes 237 and 537 for monitoring impedance and phase may pass directly through the tumor 80 as represented by dashed line 540.

Embodiment of a System Control Algorithm

The system may use various means of irrigating the ablation element. Peristaltic pumps, infusion pumps, inflators/deflators may be used. Without limiting the scope of the invention, in the case of peristaltic pumps, irrigation flow rates may be controlled indirectly, by controlling the rotational speed of the pump head. The pump is calibrated so to produce a coefficient to convert its rotational speed to an irrigation volume. For example, rotational speeds in the range of 20-100 rpm may be used to generate flow rates in the range of 2-10 ml/min. In this example the conversion coefficient to convert from rotational speed to irrigation volume would be 0.1 mL/min/rpm.

Instead of flow rates, the controller may control the volume of a bolus of hypertonic solution (or of any of the other aqueous solutions discussed above). For example, a bolus of volume of 10 ml is equivalent to an irrigation rate of 2 ml/min activated for 5 min. Bolus volumes up to 60 ml may be used.

The following is a description of an embodiment of a pump control algorithm that may be part of the software 292 stored in the ablation console 291 for controlling the pump 294 for delivering conductive fluid from the conductive fluid supply 293 to the catheter 220, 255, 270 (FIG. 11). This algorithm may function to operate the pump during the priming stage and ablation stage to maintain temperature within a target range. The said temperature may be measured by a temperature sensor in the ablation electrode 234 and may be representative of the tissue temperature. The said temperature may also represent the electrode temperature or the temperature of the conductive fluid contacting the ablation electrode. Unlike proportional-integral-derivative (PID) type of controls, which are well known in the art, this invention controls the pump flow with the triple objective of maintaining the said temperature within a range known to be therapeutically effective, of avoiding sudden impedance and temperature rises and of optimizing the amount of hypertonic infused into patient's lungs. For example, a PID controller would typically decide to control the flow within a substantially constant, or tight, range if the temperature reached levels within the therapeutic range. Instead, the controller according to the current invention controls the flow between in low and high flow values even if said temperature has already reached its targeted range. Therefore, the controller according to the current disclosure introduces flow variability into the system on purpose, with the objective of minimizing the overall amount of infused hypertonic saline within an effective operational range. Those of skill in the art may decide to use ramped flow rates, rather than fixed low-high flow rates. Rather than increasing the flow, for example, from a low value to a high value, a gradual increase may be employed. Similarly, various predictive algorithms may be employed to control flow rates. If the system senses a rapidly increasing temperature, the flow rate could be adjusted higher in anticipation of the temperature rise, so avoid overheating conditions. Similarly, if the system senses a rapidly dropping temperature, it could reduce the flow to lower rates, so to avoid large temperature fluctuation. Modified PID algorithms can also be used by using a nonlinear flow adjustment in response to the error value (i.e. difference between actual and set flow rates). Same control concepts may be used if the controlled parameter is a hypertonic saline bolus volume.

The Pump Control Algorithm runs every time a new Impedance or Temperature Data input is received from the ablation console. Impedance inputs may arrive at intervals of 40 milliseconds. Temperature Data inputs may arrive at intervals of 10 milliseconds. The algorithm is illustrated in the flow chart shown in FIG. 16A and in finer details in FIGS. 16B, 16C, and 16D. The output of the pump control algorithm is a commanded flow rate. Additionally, the algorithm may make decisions related to managing overheating or high-impedance situations. In such situations, power may be temporarily adjusted down so to bring temperature and impedance back in their normal ranges. Alternatively, the algorithm may decide to terminate delivery of energy if overheat or high-impedance conditions persist for predetermined durations of time. If it is different from the previous commanded flow rate, a new flow rate request is sent to the pump. It is important to note that the algorithm aspect of this disclosure does not shut down RF delivery as soon as overtemperature or overimpedance conditions occur. Rather, the algorithm attempts to correct such conditions by optimally modulating the flow of hypertonic saline.

In box 610, the algorithm calculates whether the High Flow Rate and Overheat Flow Rate settings need to be adjusted.

After calculating the settings adjustments, the algorithm runs the main pump control state machine, box 611. The state machine selects one of three flow rates to be sent to the pump: Low Flow Rate, High Flow Rate, and Overheat/Overimpedance Flow Rate. Additionally, pre- and post-cool flow rates may be used for the purpose of enhancing the airwayelectrode electrical contact and of cooling off the airway after ablation, respectively. However, the output of the state machine is a numeric value, in mL/min, not an enumeration. When the state machine selects a flow rate, it outputs the current setting corresponding to the flow rate. For example, if the state machine selects the Overheat/Over-impedance Flow Rate and the current setting for Overheat/Over-impedance Flow Rate is 6 mL/min, the state machine outputs 6 mL/min. For simplicity, the description herein uses identical flow rates for overheat and over-impedance conditions. Without departing from the spirit of this disclosure, different overheat and over-impedance flow rate values may be used. This will be called the state machine (SM) commanded flow rate.

If temperature or impedance exceed respective Overheat or Over-impedance thresholds, the controller may command the pump to increase flow rates to Overheat or to Over-impedance Flow Rate values. By doing so, the system attempts to prevent overheating of tissue or boiling of hypertonic saline. Once flow is increased to these higher levels, the controller may decide to maintain it to such levels for a period of time, even if the overheat or over-impedance conditions have cleared. By doing so, the controller attempts to reduce chances of recurring overheat or over-impedance conditions.

Figure 16A:
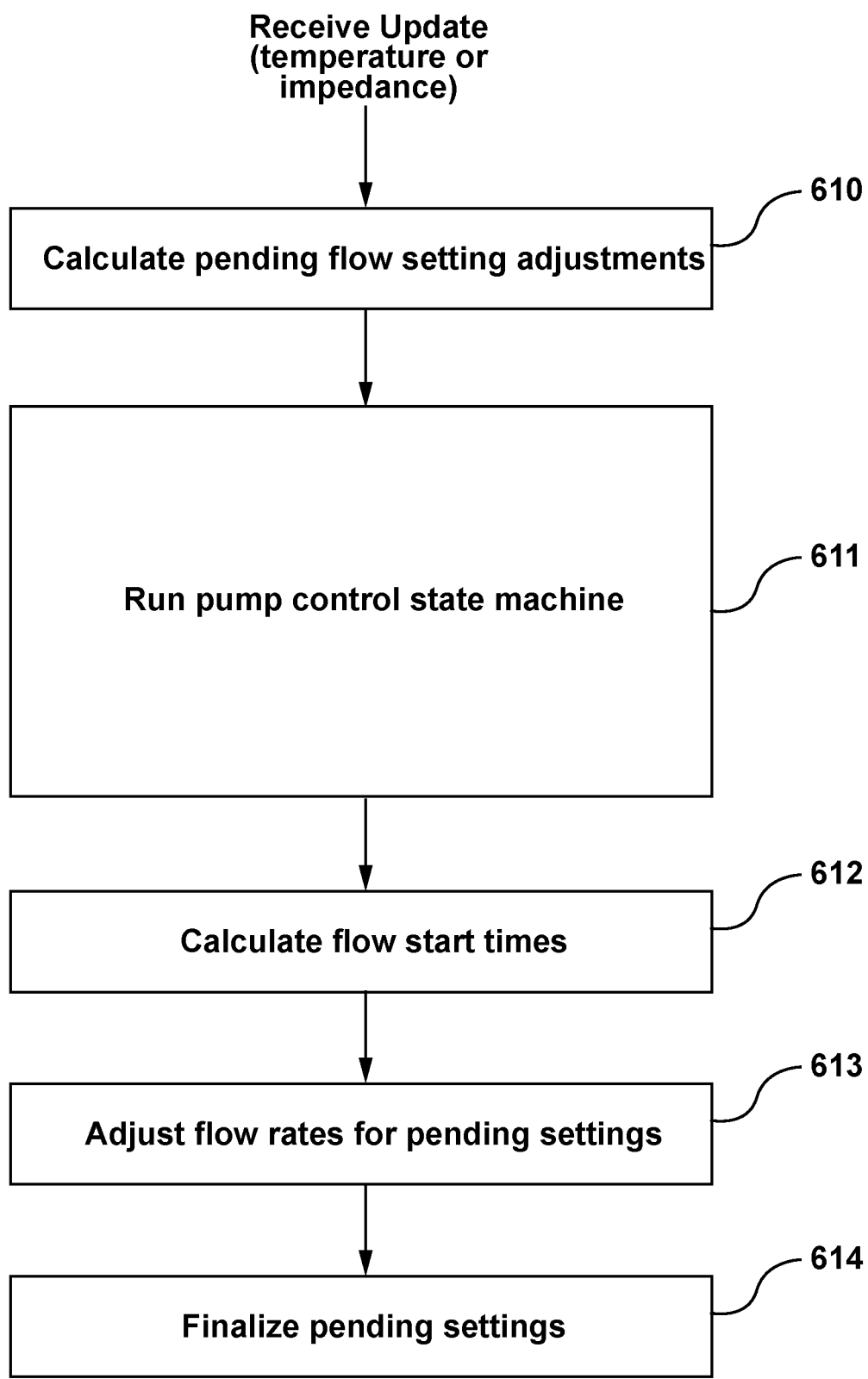
FIGS. 16A, 16B, 16C, 16D, and 16E are flowcharts representing an embodiment of a pump control algorithm.
Figure 16B:
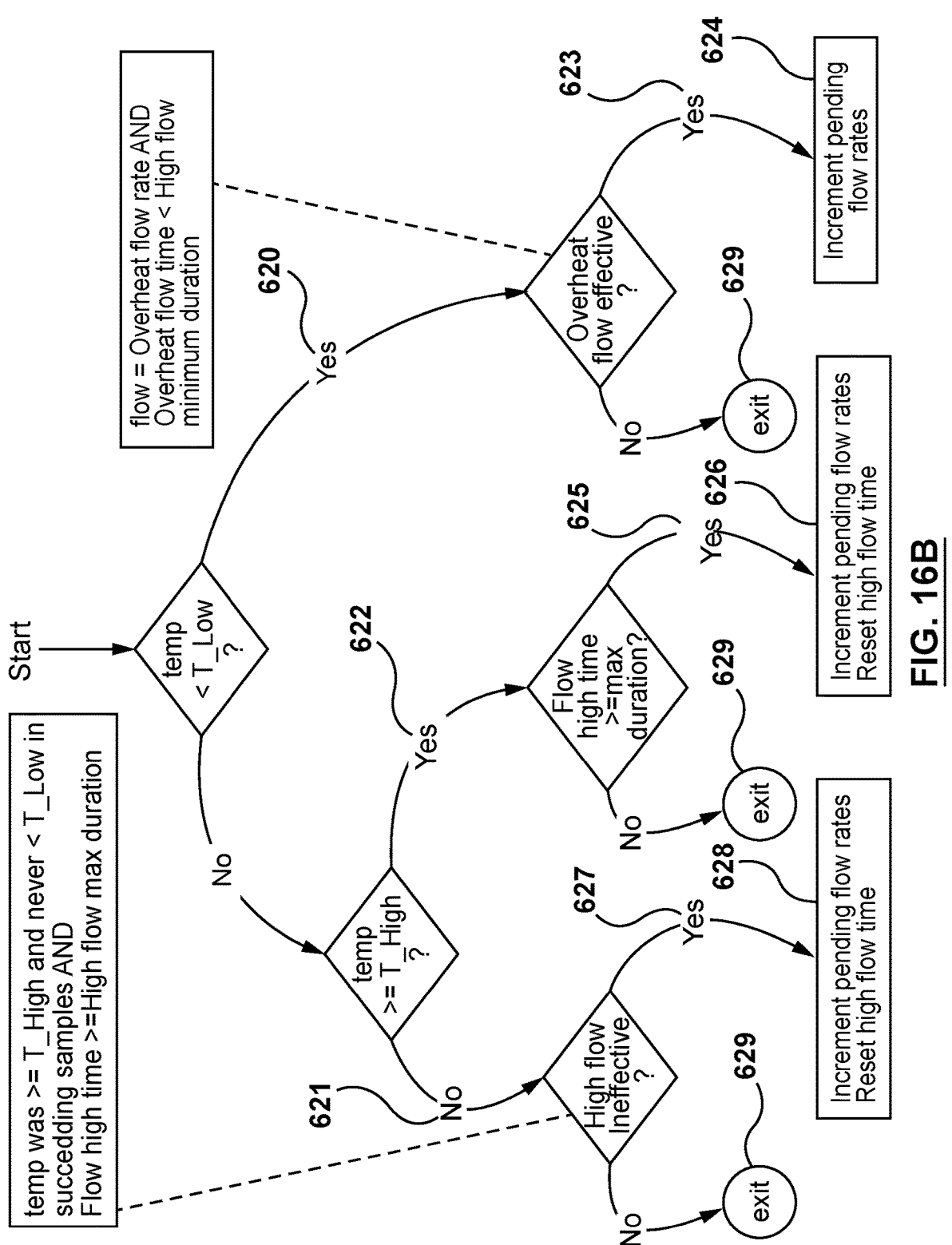

For the purpose of example, if the Calculate Settings Adjustment Section determined that the flow rate settings needed to be changed, then the commanded flow rate is adjusted to match the new settings, box 613. For example, suppose that at the start of the algorithm, High Flow Rate=2 mL/min and Overheat Flow Rate=6 mL/min. Then suppose the Calculate Settings Adjustment Section calculated pending settings of: High Flow Rate=4 mL/min and Overheat Flow Rate=8 mL/min. If the state-machine (SM) commanded flow rate is 2 mL/min (current value of High Flow Rate), then the commanded flow rate is adjusted here to 4 mL/min (new value of High Flow Rate). On the other hand, if the SM commanded flow rate is equal to the Low Flow Rate, it will not be modified here because the Low Flow Rate setting is not dynamically changed. The output of this section will be called the commanded flow rate. This is what is sent to control the pump. In general, when the temperature exceeds a T_High threshold, flow is controlled to High Flow by elements 611, 612, 613 and 614 of the state machine. Conversely, when the temperature drops below a T_Low threshold, flow is controlled to Low Flow by the same elements in FIG. 16A. The High Flow and Low Flow levels can be adjusted automatically by the controller/state machine, or manually be the user. For example, if the controller determines that a High Flow level, after a period of time (which can be manually or automatically programmed), was ineffective in reducing the said temperature to levels below T_Low then the controller can automatically increase High Flow to higher rates so that the cooling becomes more effective. Conversely, when the cooling is very effective, the controller may decide to reduce High Flow to lower levels, to minimize the amount of infused hypertonic saline. These details are illustrated in FIG. 16B. The same concepts apply to controlling Low Flow and Overheat/Over-impedance Flow. The Overheat and Over-impedance state machines are described in FIGS. 16D and 16E, respectively.

Then the pending settings changes (if any) are broadcasted to the rest of the system, box 614. The new settings will be immediately reflected in the High Flow Rate and Overheat Flow Rate spin boxes in the UI.

A more detailed view of the step of calculating pending flow settings adjustments 610 and 611 (FIG. 16A) is shown in FIG. 16B. The settings adjustment algorithm is split into three parts, depending on whether measured temperature is <T_Low 620, between T_Low and T_High 621, or >=T_High 622. As an example, if temperature<T_Low because the system has previously reached an overheat condition but the Overheat flow was effective in returning temperature to below T_Low, 623, then the state machine decides to increment the flow settings, 624. The rationale is: if the High flow rate had been higher, it may have been possible to avoid going into the overheat temperature range. If temperature>=T_High but Flow high time>=Flow high max duration 625, then the state machine decides the current Flow high rate is ineffective in returning temperature to T_Low, 625. As a consequence, the flow settings are incremented, 626. If temperature<T_High, but it does not decrease to below T_Low within a sufficiently long time (i.e. stays between T_Low and T_High for too long), the state machine decides that the current High flow was ineffective, 627. As a result, the flow settings are incremented, 628. Otherwise the flow rate settings are not incremented 629. As an example, the following settings can be used: T_Low=85° C., T_High=95° C., Flow_Low=0 mL/min, Flow_High=4 mL/min, Flow_high_time=5 s. Other values can be used with equal efficacy for example, T_Low may be in a range of 60° C. to 95° C.; T_High may be in a range of 75° C. to 105° C.; Flow_Low may be in a range of 0 to 5 mL/min; Flow_High may be in a range of 2 to 16 mL/min; Flow_high_time may be in a range of 1 to 30 seconds. Same concepts, but in reverse, can be applied to decrement flow rates when the current flow rate is very effective. By doing so, the overall amount of infused hypertonic saline is optimized. Other threshold values can be employed by those of skill in the art without departing from the spirit of this invention.

Figure 16C:
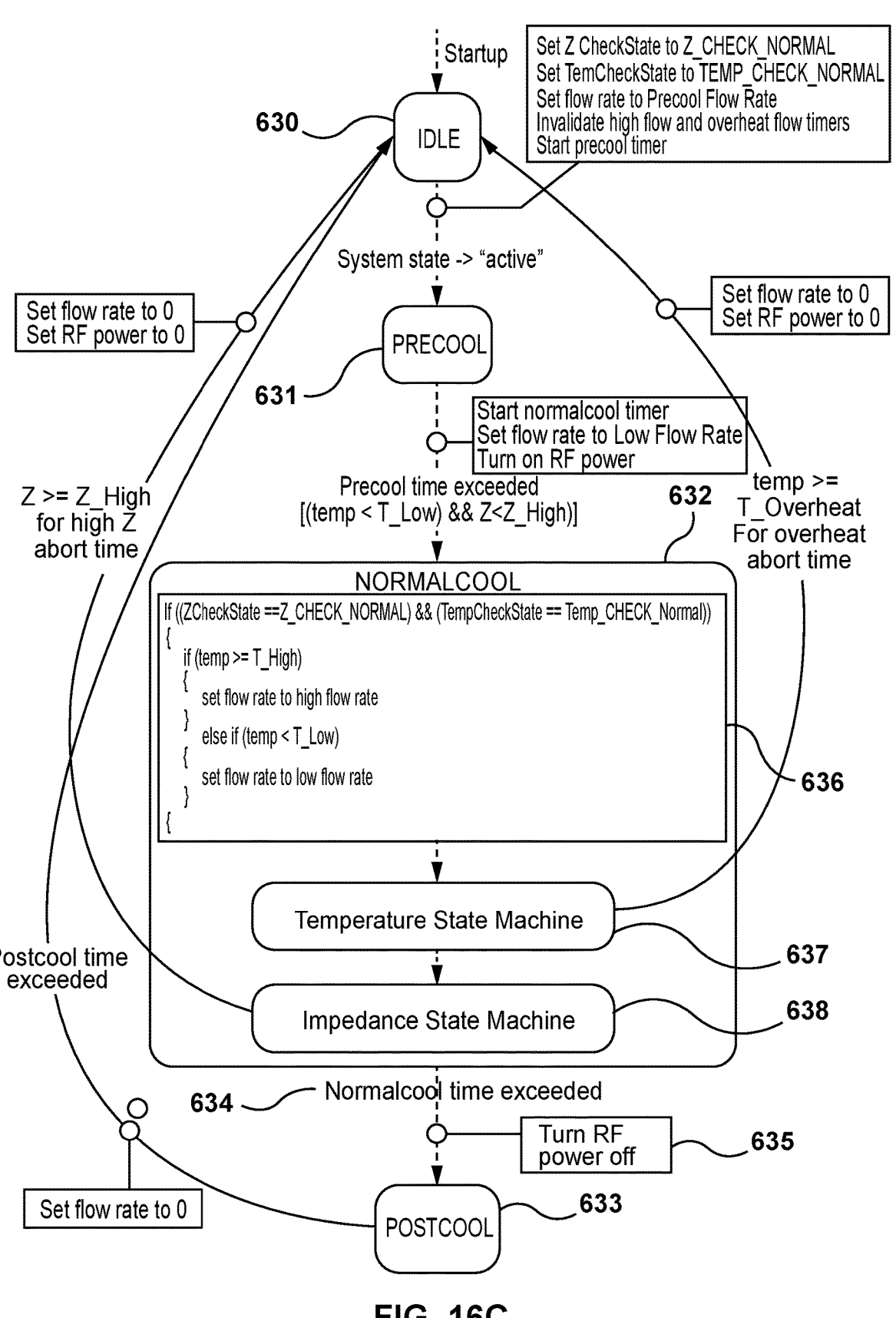

The overall state machine of the system is illustrated in more detail in FIG. 16C. The four states in the state machine include: IDLE 630, PRECOOL 631, NORMALCOOL 632, and POSTCOOL 633. The solid arrows represent transitions between states. The conditions that cause the transitions are shown as text written directly on the arrows. For example, the transition "Normalcool time exceeded" 634 indicates that when the NORMALCOOL state duration has exceeded the normalcool time setting, the state machine transitions to the POSTCOOL state 633. The boxes attached to the transitions with small circles represent actions performed when the state machine undergoes a transition. For example, the transition action box 635 containing the text "Turn RF power off" indicates that when the state machine transitions from NORMALCOOL 632 to POSTCOOL 633 the RF power is turned off.

Figure 16D:
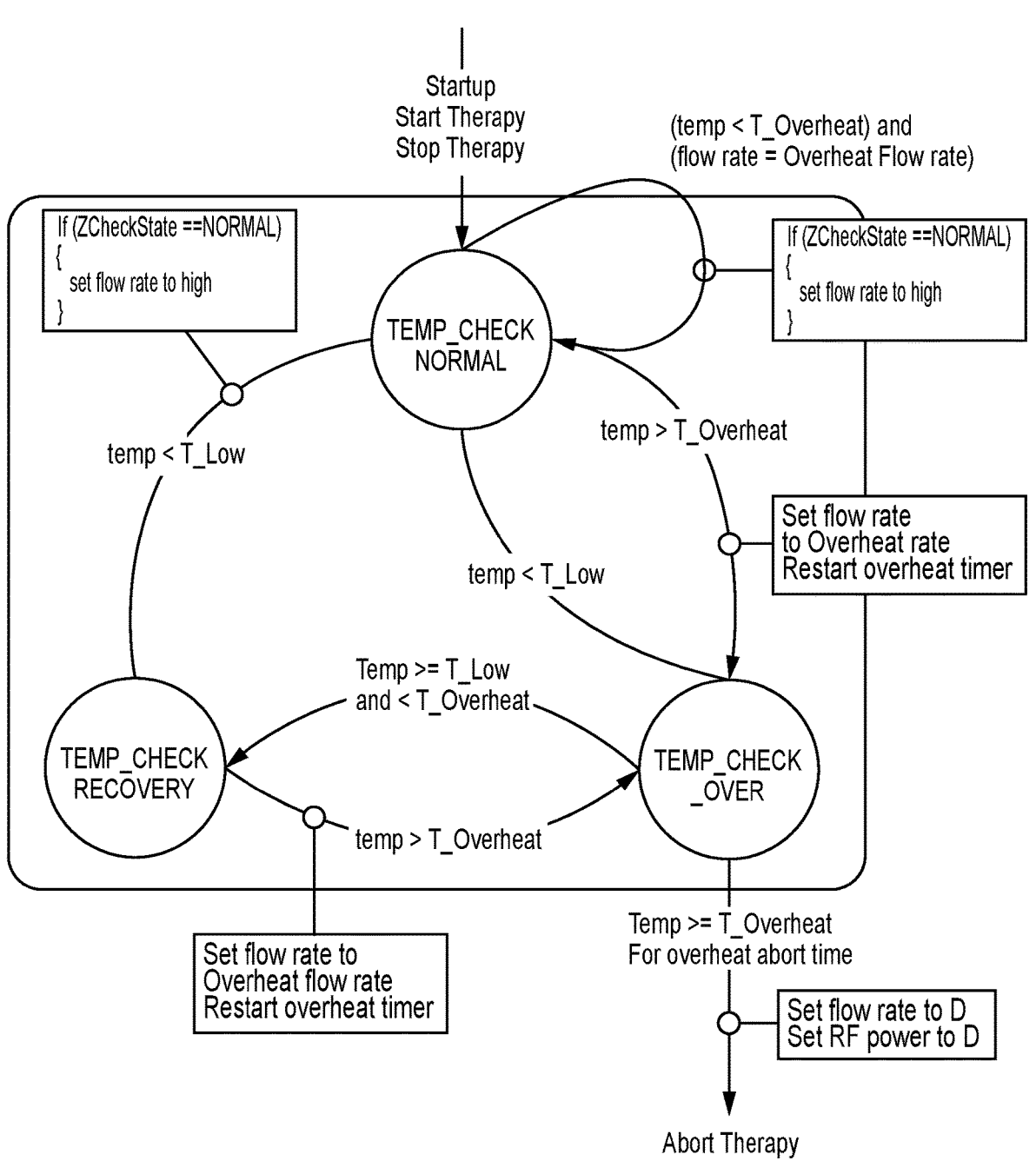
Figure 16E:
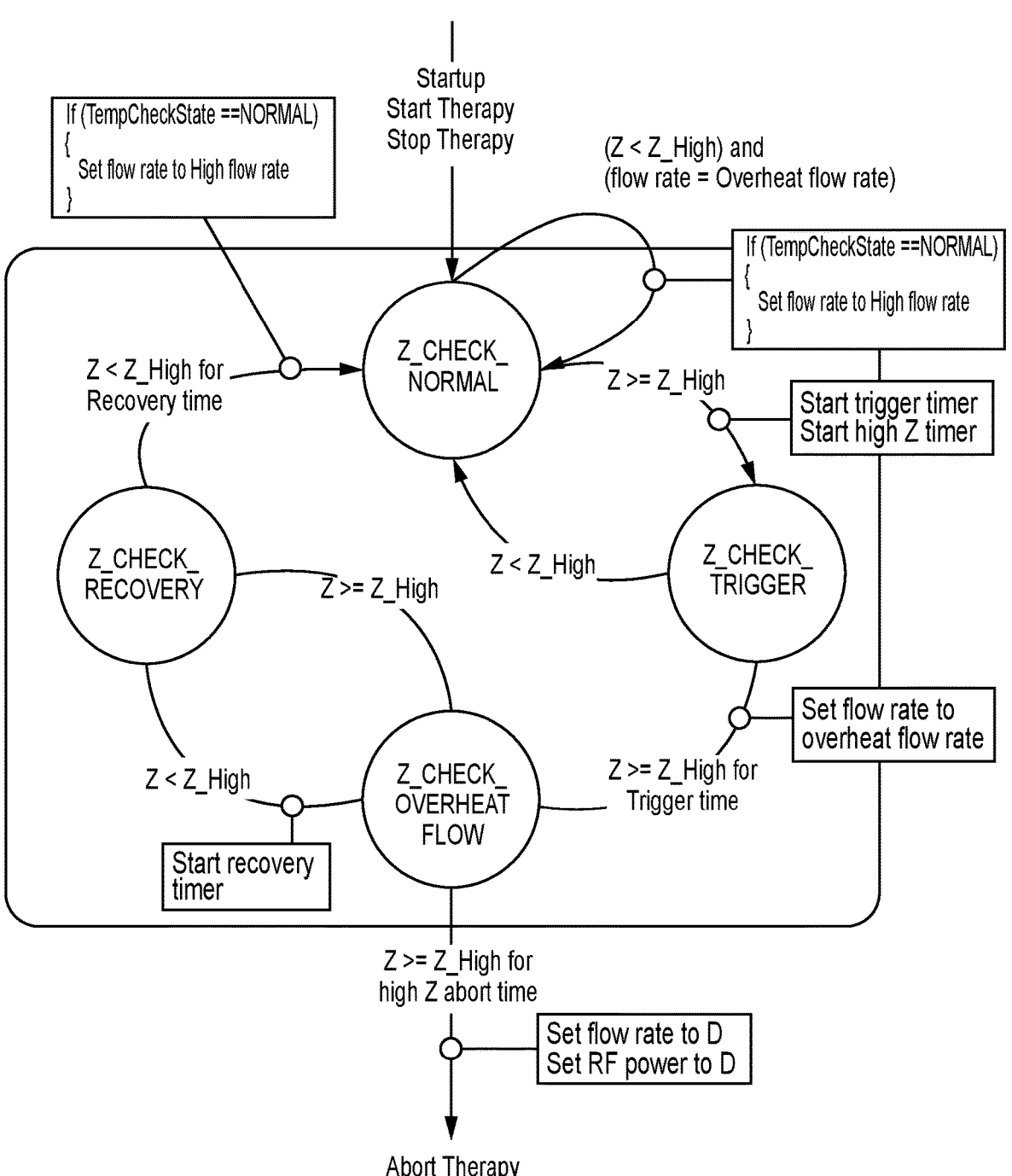

The NORMALCOOL state 632 is the most complex state in the state machine. Its details are shown in FIGS. 16A and 16B. In this state, the system is delivering RF energy to the catheter. Every time the NORMALCOOL state is run, it also checks for Overheat 637 (FIG. 16D) and for Over-impedance 638 (FIG. 16E) conditions. During a simple temperature control sub-operation 636 if temperature is too high, flow rate is increased; if too low, flow rate is decreased. However, if the sub-state machine 636 determines that temperature or impedance have reached Overheat or Over-impedance conditions, it calls on sub-state machines 637 and 638, respectively. If a Temperature State Machine sub-operation 637 is called upon, the state machine performs more elaborate calculations and is responsible for commanding overheat flow rate if temperature exceeds T_Overheat. For example, T_Overheat may be set to 105° C. and Overheat_Flow may equal 12 mL/min, but other values can be considered as well. For example, T_Overheat may be in a range of 85 to 115° C.; Overheat_Flow may be in a range of 4 to 14 mL/min. Since this state machine runs after the simple temperature control 636, it can override its results. It also can abort therapy if temperature exceeds T_overheat for too long. More details of this temperature state machine are shown in FIG. 16D. Similarly, if 636 detected an Overimpedance condition and called on the Impedance State Machine sub-operation 638, the state machine alters the pump flow rate based on measured monopolar impedance. Its objective is to increase flow rates so to keep the impedance<Z_high. For example, Z_high can be set to 600Ω and Over_impedance_Flow=12 mL/min, but other values can be equally used. For example, Z_high may as effectively be within a range of 300-1500Ω. The parameter Over_impedance_Flow may as effectively be in the range of 6-20 ml/min. Since this statement executes after the temperature state machine 637, it may override the temperature state machine's results to increase flow rate. However, it will not override with a lower flow rate. More details of this impedance state machine are shown in FIG. 16E.

Figure 17A:
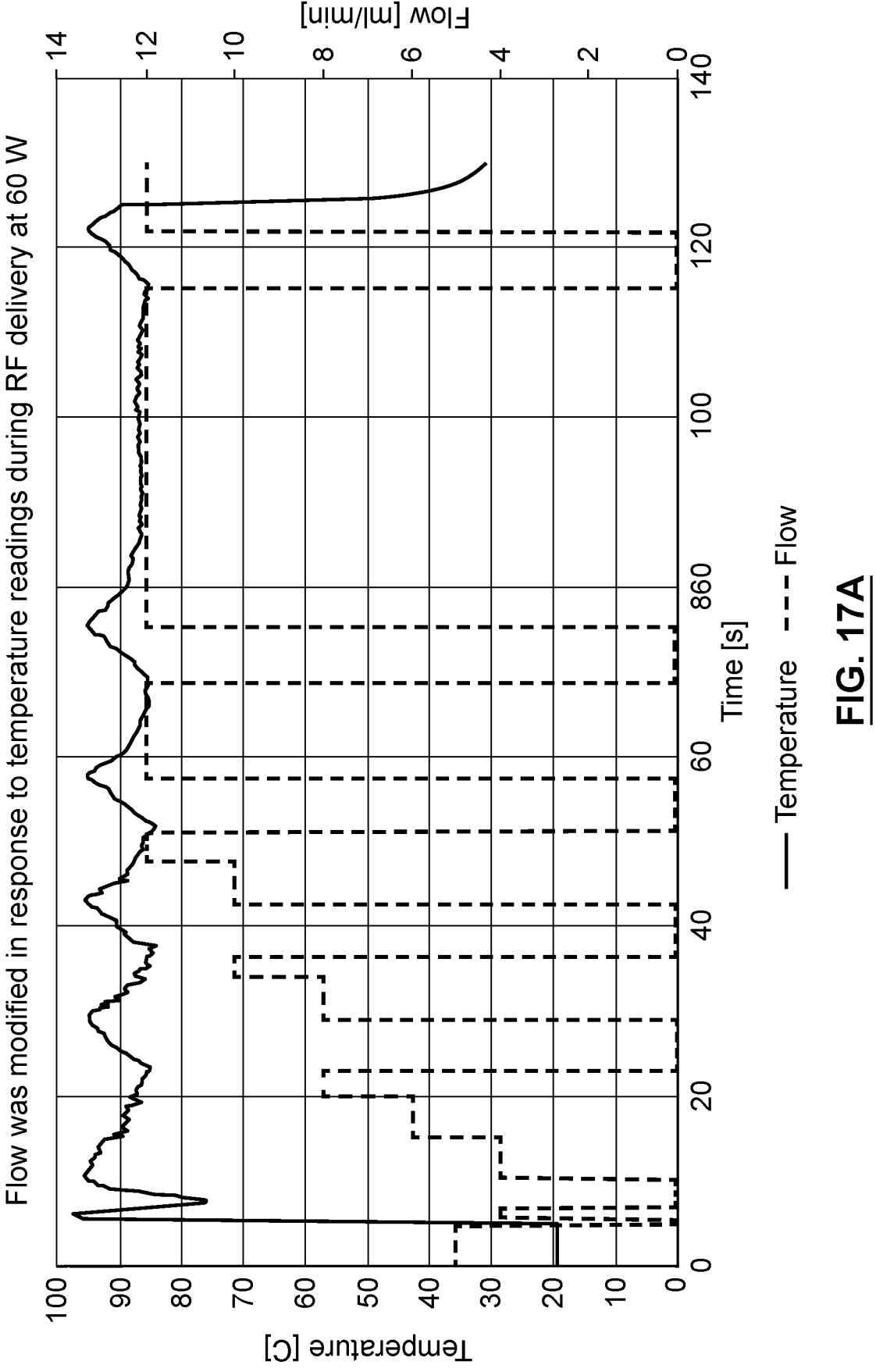
FIG. 17A is a plot of temperature and flow vs time during delivery of 60 W RF illustrating a resulting behavior of the pump control algorithm described by FIGS. 16A to 16E.
Figure 17B:
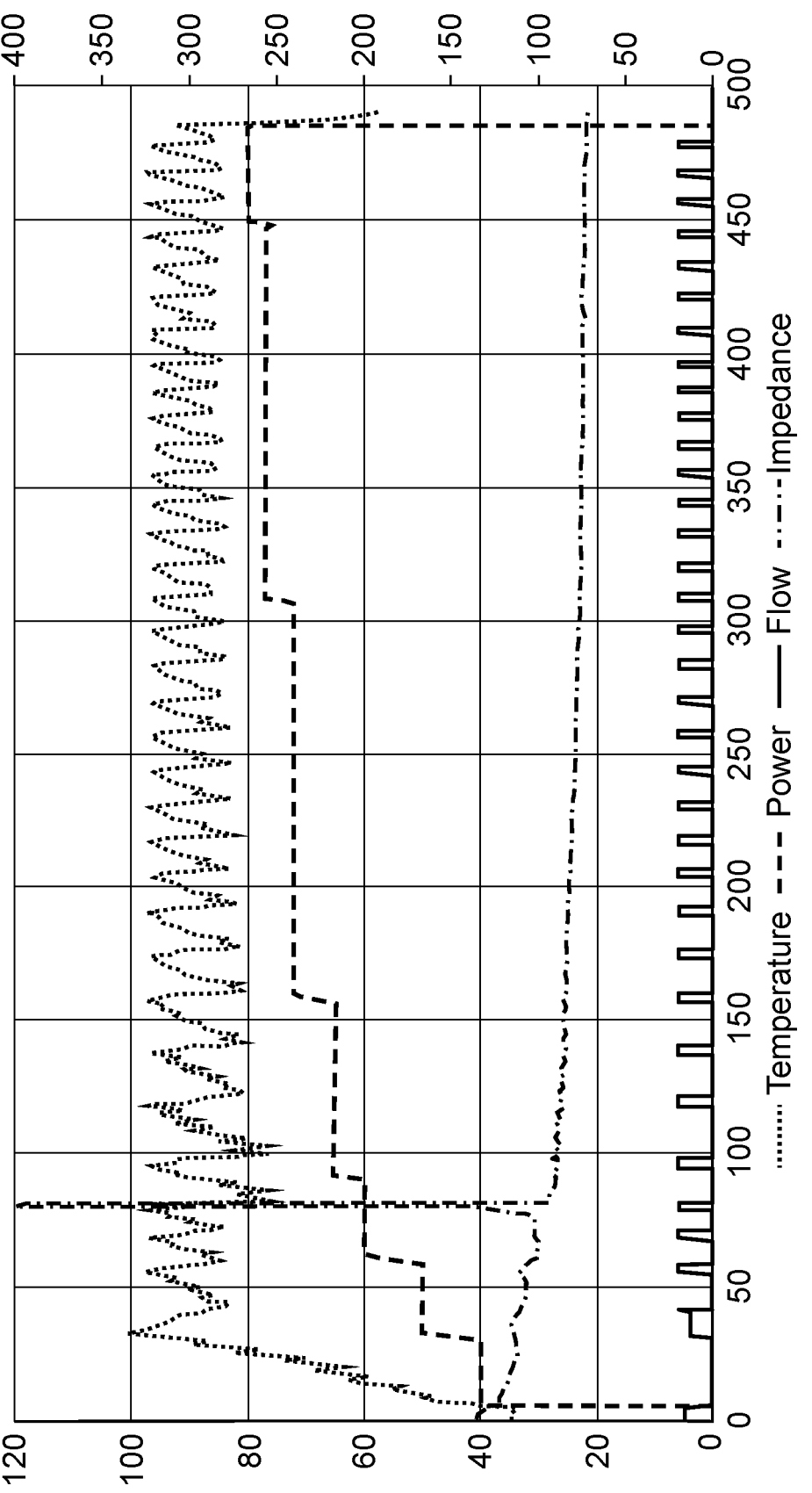
FIG. 17B is a plot of temperature, power and flow vs time during delivery of ramped power.

FIG. 17A illustrates the results of an implementation of the state diagrams presented in FIGS. 16A to 16E, where temperature 505 and flow rate 506 are plotted against time. RF ablation energy is initiated at 5s at a constant power of 60 W for 2 minutes. Prior to this between 0 s and 5 s during Precool stage the pump turns on at a flow rate of 5 mL/min, which primes the system and delivers a small amount of hypertonic saline through the ablation electrode and into the airway. At 5 seconds NormalCool state was entered, RF began to be delivered (i.e., power was increased from 0 to 60 W), flow rate was 0, and the normalcool timer was started. The temperature increased quickly and reached the upper threshold (T_High) of 95° C. The controller set the flow to 4 ml/min. Initially, 4 ml/min was effective, as the temperature dropped below T_Low of 85° C. As a consequence, flow was set back to Low Flow of 0 ml/min, in this particular example. The temperature then started to increase again and exceeded T_High. As a result, flow was again set to High Flow of 4 ml/min. However, given that this time around 4 mL/min was ineffective in reducing the temperature to below T_low of 85° C. after a period of time, Flow High Time (set to 5 s in this example), which was >=max duration, the controller incremented High Flow to 6 mL/min and reset high flow time. Yet again, after Flow_High_Time of 5 s, High Flow (which was set to 6 mL/min) was still ineffective in reducing the temperature to less than T_Low, the controller increased High Flow to 8 ml/min. This new High Flow value of 8 mL/min was effective in reducing the temperature. As such, after the temperature dropped below T_Low of 85° C. the controller set the flow to Low Flow (0 mL/min in this example). Reviewing the above in more detail, the flow of conductive fluid causes the temperature to fall below the lower threshold (T_Low) of 85° C. seen at approximately 8 s. Referring to FIG. 16B in this situation the temperature is <=T_Low 620, so the flow rate becomes 0. The flow rate remains at 0 mL/min as temperature increases but is below T_High. At approximately 10 s temperature reaches the upper threshold (T_High) triggering the flow to become the overheat flow rate of 4 mL/min for a duration of 5 s (high flow minimum duration). After 5 s the temperature is not <=T_Low AND not >=T_High 621 AND the current high flow of 4 mL/min is ineffective to bring the temperature below T_Low 627 therefore flow rates are incremented 628 to 6 mL/min and the high flow time is reset to 0 s. This new flow of 6 mL/min is applied for 5 s and again temperature is not <T_Low AND not >=T_High 627 so the flow rate is incremented again this time to 8 mL/min. Before the high flow time of 5 s is reached the temperature reaches the lower threshold (T_Low) so flow drops to 0 mL/min and stays at this rate until temperature rises and reaches the upper threshold seen at approximately 28 s. The current flow rate of 8 mL/min is triggered and run for 5 s. Again, since the temperature has not fallen below T_low with 8 mL/min the flow rate is incremented to 10 mL/min. Before the 5 s expires temperature reaches T_Low so the flow drops to 0 mL/min. At approximately 43 s temperature reaches T_High so the current flow rate of 10 mL/min is triggered for another 5 s at which time the flow is incremented to 12 mL/min because 10 mL/min was ineffective to bring temperature to T_Low. At approximately 51 s temperature reaches T_Low so flow becomes 0. With 0 mL/min flow the temperature rises again reaching T_High at about 57 s triggering the now current flow of 12 mL/min after 5 s the flow is determined to be effective so remains at 12 mL/min until temperature reaches T_Low at about 70 s. Flow drops to 0 mL/min and when temperature reaches T_High at about 76 s the now current flow of 12 mL/min is triggered. This flow manages to effectively reduce temperature and keep it between T_High and T_Low until about 115 s where temperature reaches T_Low and flow is set to 0. In this example, although the Flow_High_Time of 5 s was exceeded, flow was not increased further because 12 ml/min was programmed to be the maximum allowed High Flow level. Other maximum levels could be used by those of skill in the art. At about 122 s temperature reaches again T_High so flow is set to 12 mL/min. At 125 s the NormalCool timer finishes and RF power is turned off and flow is set to 0 as the PostCool stage is entered. FIG. 17B shows the system behavior when power was ramped up gradually. Rather than applying a power step (e.g. 0 to 60 W), in FIG. 17B power was gradually increased from 40 W to a steady value of approximately 75 W. In such a control scenario, power could be maintained at 40 W for the first 30 s, then increased to 50 W for the next 30 s and so on until the target maximum power level is reached. The advantage of such power control algorithm stems from that is reduces the probability of tissue popping or tissue cavities. Both tissue popping and cavities represent a potential safety concern as they could lead to pneumothoraces.

2<sup>nd</sup> Embodiment of a System Control Algorithm

Figure 20:
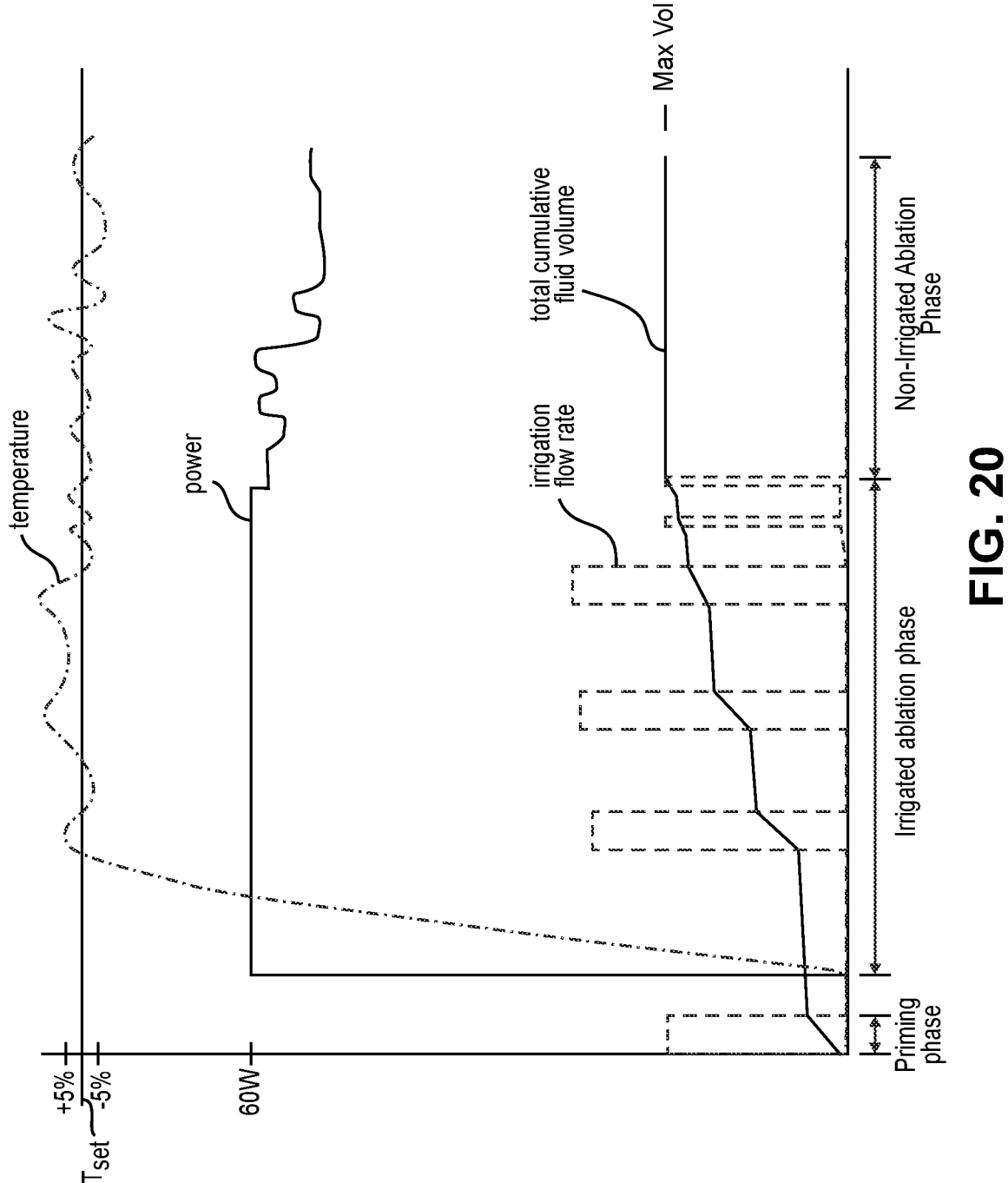
FIG. 20 is a plot of temperature, RF power, irrigation flow rate, and total cumulative volume of irrigated fluid vs. time for a control algorithm.

A description of second system control algorithm follows, wherein a controller is used to adjust the flowrate of conductive fluid, an RF power control algorithm adjusts RF power, and the total amount of conductive fluid delivered or a condition representative of a total amount of conductive fluid delivered is monitored, for example to avoid delivering too much conductive fluid. An example plot of an ablation procedure using this control algorithm is shown in FIG. 20. The second system control algorithm may be part of the software 292 stored in the ablation console 291 for controlling the pump 294 for delivering conductive fluid from the conductive fluid supply 293 to the catheter 220, 255, 270 and for delivering ablation energy from the ablation console 291 to the ablation catheter 220, 255, 270 (FIG. 11), in particular to an ablation electrode 234, 250, 434, 534 on an ablation catheter. This algorithm may function to operate the pump during the priming stage and ablation stage to maintain temperature within a target range and to deliver conductive fluid within a desired total volume, for example below a desired maximum volume, or within a total volume that results in a set of conditions. The said temperature may be measured by a temperature sensor in the ablation electrode 234, 250, 434, 534 and may be representative of the tissue temperature. The said temperature may also represent the electrode temperature or the temperature of the conductive fluid contacting the ablation electrode.

Although delivery of conductive fluid (e.g., hypertonic saline) during delivery of RF energy is advantageous for achieving ablation of a lung tumor, too much conductive fluid delivered to the target lung region may have deleterious effects, for example too much conductive fluid may create an ablation that is larger than intended or may fill the target lung region and leak from the region, which may result in irritation or injury to non-target tissue. Thus, it is an objective of this second system control algorithm to deliver sufficient conductive fluid (e.g., hypertonic saline) to ablate a target lung tumor, while avoiding delivery of too much conductive fluid that may increase safety risks.

The procedure may involve a lung volume reduction phase, a priming phase in which conductive fluid is delivered prior to delivery of RF ablation energy to fill the fluid delivery conduit and wet the ablation electrode, an irrigated ablation phase in which conductive fluid is delivered and ablative RF energy is delivered concomitantly, and a non-irrigated ablation phase in which conductive fluid exists in the target region of the lung but is no longer added and ablative RF energy is delivered. The lung reduction phase in which suction is applied to an occluded target region of a lung containing a target tumor is may be as is described in more detail herein and may involve various occlusion elements, impedance sensors, vacuum pumps or control algorithms. Throughout the procedure, including all phases, the cumulative total volume of conductive fluid may be calculated (e.g., based on flow rates or pump speeds and times) and optionally displayed on the console's user interface. A user may reset the total calculated volume when a patient begins a procedure. A maximum total conductive fluid volume may be predefined, for example in a range of 10 mL to 20 mL. Alternatively, maximum total conductive fluid volume may be a user defined parameter set before the start of the procedure and may optionally be adjusted during the procedure, for example according to a physician's judgment, which may be based on target region volume, visual indications as seen through a bronchoscope, or patient response. Alternatively, maximum total conductive fluid volume may be calculated as a function of parameters such as desired ablation volume, target lung region volume, proximity to pleura or other tissue, proximity to the center of the tumor, patient size, and optionally be user adjustable during the procedure.

Following the lung volume reduction phase and the priming phase a user may actuate a start button to initiate the irrigated ablation phase. In this phase ablative RF power is delivered and conductive fluid is irrigated through the ablation electrode. Inputs to the control algorithm during this phase may include target ablation electrode temperature, measured ablation electrode temperature, monopolar impedance, monopolar phase, bipolar phase, and bipolar impedance. The algorithm may receive time or duration data from a timing circuit. The algorithm may output a set RF ablation power amplitude profile, an irrigation pump speed or on/off setting, and a total cumulative volume of conductive fluid (e.g., HTS). RF Power may be set to a constant amplitude, for example in a range of 50 W to 80 W (e.g., in a range of 55 W to 75 W, 55 W to 65 W, 60 W) and remain at this amplitude during the remainder of the irrigated ablation phase. Optionally, RF Power may be titrated in response to certain events, for example a quick rise in impedance caused by patient movement or desiccation of tissue adjacent the electrode, may result in a drop or pause in RF power until the impedance regains stability. Optionally, RF Power may be initially ramped from OW up to the constant amplitude for example over a period of up to 30 s (e.g., up to 25 s, up to 20 s, up to 10 s). During this phase the conductive fluid may be delivered with a bolus or flow rate determined by the control algorithm in order to adjust the measured electrode temperature to match the target set temperature. For example, the control algorithm may use a PID controller, or a variant of a PID controller, to control flow of the conductive fluid to irrigate the target region and to maintain the measured temperature at or near the target temperature. The target temperature may be in a range of 80° C. to 100° C. (e.g., in a range of 85° C. to 95° C., about 90° C.). Optionally, if the measured temperature is within a close range of the set temperature (e.g., within 4° C. of the set temperature, within 5% of the set temperature) then irrigation may be set to 0 mL/min or to a very low flow rate (e.g., less than 1 mL/min, less than 0.5 mL/min), which may further contribute to minimizing the total volume of fluid delivered. For example, if the measured temperature is above 95° C. and the set temperature is 90° C. irrigation may be turned on to lower the measured temperature and when measured temperature reaches 94° C. irrigation may be turned off. The control algorithm may continue in the irrigated ablation phase until the total cumulative delivered volume of fluid reaches, or optionally approaches, the predefined maximum volume, wherein the non-irrigated ablation phase is entered. Optionally, if the total cumulative volume is approaching the maximum volume, for example within 2 mL of the maximum volume, the RF power amplitude may be decreased, for example dropped by an amount in a range of 5 W to 20 W.

During the non-irrigated ablation phase, conductive fluid exists in the target lung region from the previous irrigated ablation phase, irrigation is stopped to avoid delivering too much fluid, and the control algorithm titrates RF power to bring measured temperature toward set temperature, for example using a PID controller or a variant of a PID controller. Set temperature may remain the same as in the previous irrigated ablation phase (e.g., 90° C.) or may be changed. Optionally, the RF power may be changed in small increments (e.g., 5 W increments).

Alternative to or in addition to comparing a measured cumulative fluid volume to a predefined maximum volume to define if the algorithm is in the irrigated ablation phase or non-irrigated ablation phase, the algorithm may use other inputs or conditions. For example, conditions that indicate the irrigated fluid may be leaking or in danger of leaking from the occluded lung space may trigger the algorithm to enter the non-irrigated phase. These triggers may also identify device failure such as a ruptured occlusion balloon. A fluid leak condition may be determined using sensors on the ablation catheter. For example, a temperature sensor proximal to the occlusion element may show an increase if hot fluid leaks and contacts the sensor. Optionally, an acceptable increase in temperature proximal to the occlusion element, for example due to thermal conduction along the catheter shaft may not trigger a change but a sudden temperature change (e.g., an increase of at least 5° C. in 1 s) may trigger a change to non-irrigated ablation, or to pause all irrigation and RF delivery until a user instructs the algorithm to continue. Impedance measured from a sensor proximal the occlusion element may indicate a leak if decreased. Bipolar impedance distal to the balloon may assess fluid volume. Pressure measured in the occluded space compared to ambient pressure or pressure proximal the occlusion element may rise as fluid is delivered and a maximum set pressure difference may trigger the algorithm to stop or pause irrigation and enter non-irrigated ablation phase. A user may input through the user interface a signal that manually interrupts the irrigated ablation phase and enters the non-irrigated ablation phase, for example if the user notices the patient coughing or sees a fluid leak via the bronchoscope.

Optionally, if a non-irrigated ablation phase is entered due to a sensed condition but the predefined total maximum volume has not been reached, the algorithm may re-enter an irrigated ablation phase if the sensed condition is relieved.

Optionally, if the total volume of fluid reaches or approaches the maximum total volume the fluid may be allowed to leak, for example by manually or automatically opening a valve, out of the occluded lung space through a lumen in the ablation catheter, optionally through a guidewire lumen. The volume of saline leaked may be measured (e.g., by weighing it or measuring with a flow meter) and subtracted from the cumulative total volume and the irrigated ablation phase may continue as long as the maximum fluid volume is not reached.

The system may use various means of irrigating the ablation element. Peristaltic pumps, infusion pumps, inflators/deflators may be used. Without limiting the scope of the invention, in the case of peristaltic pumps, irrigation flow rates may be controlled indirectly, by controlling the rotational speed of the pump head. The pump is calibrated so to produce a coefficient to convert its rotational speed to an irrigation volume. For example, rotational speeds in the range of 20-100 rpm may be used to generate flow rates in the range of 2-10 ml/min. In this example the conversion coefficient to convert from rotational speed to irrigation volume would be 0.1 mL/min/rpm.

Instead of flow rates, the controller may control the volume of a bolus of hypertonic solution (or of any of the other aqueous solutions discussed above). For example, a bolus of 10 ml is equivalent to an irrigation rate of 2 ml/min activated for 5 min. Bolus volumes up to 60 ml may be used.

Optionally, during the irrigated ablation phase, the conductive fluid may be chosen by the control algorithm from a plurality of sources having different properties, for example a hypertonic saline and a normal saline as described herein to mitigate edema.

Those of skill in the art may decide to use ramped flow rates, rather than fixed low-high flow rates. Rather than increasing the flow, for example, from a low value to a high value, a gradual increase may be employed. Similarly, various predictive algorithms may be employed to control flow rates. If the system senses a rapidly increasing temperature, the flow rate could be adjusted higher in anticipation of the temperature rise, so avoid overheating conditions. Similarly, if the system senses a rapidly dropping temperature, it could reduce the flow to lower rates, so to avoid large temperature fluctuation. Modified PID algorithms can also be used by using a nonlinear flow adjustment in response to the error value (i.e. difference between actual and set flow rates). Same control concepts may be used if the controlled parameter is a hypertonic saline bolus volume.

The Pump Control Algorithm runs every time a new Impedance or Temperature Data input is received from the ablation console. Impedance inputs may arrive at intervals of 40 milliseconds. Temperature Data inputs may arrive at intervals of 10 milliseconds. The output of the pump control algorithm is a commanded flow rate. Additionally, the algorithm may make decisions related to managing overheating or high-impedance situations. In such situations, power may be temporarily adjusted down so to bring temperature and impedance back in their normal ranges. Alternatively, the algorithm may decide to terminate delivery of energy if overheat or high-impedance conditions persist for predetermined durations of time. If it is different from the previous commanded flow rate, a new flow rate request is sent to the pump.

The system(s), catheter(s) and apparatus described above and/or claimed may use at least one controller. This controller may comprise a digital processor (CPU) with memory (or memories), an analogical type circuit, or a combination of one or more digital processing units with one or more analogical processing circuits. In the present description and in the claims, it is indicated that the controller is "configured" or "programmed" to execute certain steps. This may be achieved in practice by any means which allow configuring or programming the controller. For instance, in case of a controller comprising one or more CPUs, one or more programs are stored in an appropriate memory. The program or programs containing instructions which, when executed by the controller, cause the controller to execute the steps described and/or claimed in connection with the controller. Alternatively, if the controller is of an analog type, then the circuitry of the controller is designed to include circuitry configured, in use, to process electric signals, such as to then execute the controller steps herein disclosed and/or claimed.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention is:

1. A method to treat target region of lung tissue, the method comprising:

advancing a catheter endobronchially into an airway of the lung to position a distal region of the catheter at or in proximity of the target region of the lung tissue, controlling a flow regulator to control a flow of a conductive fluid through a conductive fluid outlet at the distal region of the catheter and into the target region;

applying ablation energy to an ablation electrode mounted to the distal region of the catheter to heat the conductive fluid to ablate the target region;

maintaining a temperature in the target region or at the distal region of the catheter within a first temperature range by controlling the flow regulator to adjust the flow or a bolus of the conductive fluid delivered to the conductive fluid outlet to the target region;

determining an amount of the conductive fluid delivered through the conductive fluid output;

in response to the amount of the conductive fluid reaching a threshold volume, ceasing or minimizing the flow or bolus of the conductive fluid to the conductive fluid output; and during the cessation or minimization of the flow or bolus of the conductive fluid to the conductive fluid output, maintaining the temperature in the target region or at the distal region of the catheter within a second temperature range by adjusting the ablation energy delivered to the ablation electrode.

2. The method of claim 1, wherein the first and/or second temperature range is in a range of 80° C. to 100° C.

3. The method of claim 1, wherein the step of controlling the flow regulator includes: stopping or reducing the flow of the conductive fluid to the conductive fluid outlet while the temperature in the target region is below a predefined temperature within the first temperature range.

4. The method of claim 1, wherein the threshold volume is in a range of 10 mL to 20 mL.

5. The method of claim 1, wherein the ablation energy is delivered to the ablation electrode at a substantially constant power level until the amount of the conductive fluid reaches the threshold volume.

6. The method of claim 1, wherein the ablation energy delivered to the ablation electrode is maintained in a range of 50 W to 80 W at least until the amount of the conductive fluid reaches the threshold volume.

7. The method of claim 6, wherein the ablation energy delivered to the ablation electrode is reduced by between 5 W to 20 W in connection with the cessation or the minimization of the flow of the conductive fluid.

8. The method of claim 1, wherein, after the amount of the conductive fluid reaches the threshold volume and during the step of the cessation or the minimization of the flow of the conductive fluid, the ablation energy delivered to the ablation electrode is reduced below a power level delivered to the ablation electrode while the conductive fluid is delivered to the target region and before the amount of the conductive fluid reaches the threshold level.

9. The method of claim 1, wherein the conductive fluid is hypertonic saline with a sodium chloride concentration of 5% to 30% by weight/volume.

10. The method of claim 1, wherein the advancement of the catheter includes advancing the catheter from a working channel of a bronchoscope inserted into the airway.

11. A system for treatment of a target region of lung tissue, the system comprising:

a catheter configured to advance endobronchially into an airway of the lung to position a distal region of the catheter at or in proximity of the target region of the lung tissue, a flow regulator configured to be interposed between a conductive fluid source and a conductive fluid outlet at the distal region of the catheter, wherein the flow regulator is configured to control delivery of conductive fluid from the fluid source and through the conductive fluid outlet to the target region;

an ablation electrode mounted to the distal region of the catheter;

a controller configured to:

control the delivery of power from the ablation energy source to the ablation electrode;

control the flow regulator to control a flow rate or a bolus quantity of the conductive fluid from the fluid source and delivered through the conductive fluid outlet to the target region;

wherein the controller is further configured to execute a procedure comprising:

an irrigated ablation phase in which the controller commands the flow regulator to deliver the conductive fluid to the conductive fluid outlet and concomitantly commands delivery of RF ablation energy from the ablation energy source to the ablation electrode, and a non-irrigated ablation phase in which the controller commands the flow regulator to substantially stop delivery of conductive fluid to the conductive fluid outlet and concomitantly commands a reduction in the RF ablation energy delivered from the ablation energy source to the ablation electrode.

12. The system of claim 11, wherein the controller is configured to command execution of the non-irrigated ablation phase after execution of the irrigated ablation phase.

13. The system of claim 11, wherein the procedure further comprises a priming phase, executed before the irrigated ablation phase, in which the controller commands the flow regulator to deliver conductive fluid prior to commanding delivery of RF ablation energy from the ablation energy source to the ablation electrode.

14. The system of claim 11, wherein the controller is further configured to:

maintain a temperature in the target region or at the distal region of the catheter within a first temperature range by controlling the flow regulator to adjust the flow or bolus of the conductive fluid delivered to the conductive fluid outlet.

15. The system of claim 14, wherein the controller is configured to maintain the temperature in the target region or at the distal region of the catheter within the first temperature range by controlling the flow regulator to adjust the flow or bolus of the conductive fluid delivered to the conductive fluid outlet, during said irrigated ablation phase.

16. The system of claim 11, wherein the controller, at least during the irrigated ablation phase, is further configured to:

determine an amount of the conductive fluid delivered through the conductive fluid output, and in response to the amount of the conductive fluid reaching a threshold volume, ceasing or minimizing the flow or bolus of the conductive fluid to the conductive fluid output.

17. The system of claim 16, wherein the controller is further configured to execute, during the non-irrigation ablation phase the further step of maintaining a temperature in the target region or at the distal region of the catheter within a second temperature range by adjusting the RF ablation energy delivered to ablation electrode.

18. The system of claim 11, wherein the step of controlling the flow regulator includes during the irrigated ablation phase: stopping or minimizing the flow of the conductive fluid to the conductive fluid outlet while the temperature in the target region is below a predefined temperature.

19. The system of claim 11, wherein the threshold volume is in a range of 10 mL to 20 mL.

20. The system of claim 11, wherein the controller, during the irrigated ablation phase, sets the RF ablation energy delivered to the ablation electrode at a substantially constant power level.

21. The system of claim 11, wherein the RF ablation energy delivered to the ablation electrode during the non-irrigated ablation phase is in a range of 5 W to 20 W below the RF ablation energy delivered during the irrigated ablation phase.

22. The system of claim 11, wherein, during the non-irrigated ablation phase, the controller reduces the RF ablation energy delivered to the ablation electrode below a power level delivered to the ablation electrode during the irrigated ablation phase.

23. The system of claim 11, wherein the conductive fluid is hypertonic saline with a sodium chloride concentration in a range of 5% to 30% by weight volume.

24. The system of claim 11, wherein the controller is further configured to:

receive values detected by a sensor positioned in the lung tissue and outside of the target region, wherein the sensor that detects values of a control parameter representative of a physical property which is at least one of: temperature (T), pressure (P), electric impedance (Z), and electric conductivity (C) of lung tissue outside of the target region of lung tissue; and during the irrigated ablation phase, reduce or cease delivery of the flow of the conductive fluid to the conductive fluid output depending on the received values detected by the sensor.

25. The system of claim 24, wherein the delivery of the flow of the conductive fluid to the conductive fluid output is reduced or ceased in response to a determination by the controller that the received values indicate the conductive fluid leading into the lung tissue is outside of the target region.

26. A method to ablate a target region of lung tissue comprising:

advancing a catheter endobronchially into an airway of the lung to position a distal region of the catheter at or proximate to the target region, controlling a flow of a conductive fluid through the catheter, a conductive fluid outlet in the distal region and into the target region during an irrigated ablation phase;

applying RF energy at a first power level to an ablation electrode mounted to the distal region of the catheter during the irrigated ablation phase;

initiating a non-irrigated ablation phase in response to the conductive fluid flowing through the conductive fluid outlet reaching a threshold amount during the irrigated ablation phase, and during the non-irrigated ablation phase, reducing the RF energy applied to the ablation electrode to a second power level below the first power level and ceasing or minimizing the flow of the conductive fluid through the conductive fluid outlet.

27. The method of claim 26, the advancement of the catheter includes advancing the catheter from a working channel of a bronchoscope inserted into the airway.

28. The method of claim 26, wherein the conductive fluid is hypertonic saline with a sodium chloride concentration of 5% to 30% by weight/volume.

* * * * *